(12) United States Patent
Holden

(10) Patent No.: US 12,626,820 B2
(45) Date of Patent: May 12, 2026

(54) MODERATED COMMUNICATION SYSTEM FOR INFERTILITY TREATMENT

(71) Applicant: John Patrick Holden, Rockford, IL (US)

(72) Inventor: John Patrick Holden, Rockford, IL (US)

(73) Assignee: John Patrick Holden, Rockford, IL (US)

( * ) Notice: Subject to any disclaimer, the term of this patent is extended or adjusted under 35 U.S.C. 154(b) by 90 days.

(21) Appl. No.: 18/223,006

(22) Filed: Jul. 17, 2023

(65) Prior Publication Data

US 2024/0029885 A1     Jan. 25, 2024

Related U.S. Application Data

(63) Continuation-in-part of application No. PCT/US2023/027883, filed on Jul. 17, 2023.

(60) Provisional application No. 63/389,918, filed on Jul. 17, 2022.

(51) Int. Cl.
| | |
|---|---|
| *G16H 50/20* | (2018.01) |
| *G16H 10/20* | (2018.01) |
| *G16H 10/60* | (2018.01) |
| *G16H 40/67* | (2018.01) |
| *G16H 70/20* | (2018.01) |

(52) U.S. Cl.
CPC ............. *G16H 50/20* (2018.01); *G16H 40/67* (2018.01); *G16H 70/20* (2018.01); *G16H 10/20* (2018.01); *G16H 10/60* (2018.01)

(58) Field of Classification Search
CPC ........ G16H 50/20; G16H 40/67; G16H 70/20; G16H 10/60; G16H 10/20; G16B 20/00; G16B 40/00; G06T 7/0012; G01N 33/483
See application file for complete search history.

(56) References Cited

U.S. PATENT DOCUMENTS

| | | | | |
|---|---|---|---|---|
| 11,049,603 | B1 * | 6/2021 | Neumann | .............. G16H 50/20 |
| 2012/0016206 | A1 * | 1/2012 | Ramarajan | ............. G16H 70/20 |
| | | | | 600/300 |
| 2015/0088541 | A1 * | 3/2015 | Yao | ........................ G06Q 10/10 |
| | | | | 705/2 |
| 2016/0357917 | A1 * | 12/2016 | Yao | ...................... A61B 17/425 |

(Continued)

FOREIGN PATENT DOCUMENTS

WO       2006037236 A1     4/2006

OTHER PUBLICATIONS

Maity, N. G., Das, S., "Machine learning for improved diagnosis and prognosis in healthcare," 2017 IEEE Aerospace Conference, Big Sky, MT, USA, 2017, pp. 1-9, doi: 10.1109/AERO.2017. 7943950. (Year: 2017).*

(Continued)

*Primary Examiner* — Devin C Hein
*Assistant Examiner* — Vincent C Ilagan
(74) *Attorney, Agent, or Firm* — Potomac Law Group, PLLC; Marc Kaufman

(57)     ABSTRACT

The systems and methods of the invention provide several improvements directed at fertility treatment. These improvements include an expert/AI system configured to guide a caregiver, e.g., a physician, through the process of providing fertility treatment. They also include a communication system between the caregiver and a patient, which is moderated by the expert/AI system.

25 Claims, 27 Drawing Sheets

(56) References Cited

U.S. PATENT DOCUMENTS

| | | | |
|---|---|---|---|
| 2017/0196458 A1* | 7/2017 | Ternes | A61B 7/023 |
| 2019/0148007 A1* | 5/2019 | Griffin | G16H 10/60 |
| | | | 705/3 |
| 2019/0252043 A1* | 8/2019 | Elashoff | G16B 20/00 |
| 2019/0392924 A1* | 12/2019 | Bettencourt-Silva | |
| | | | G16H 50/70 |
| 2020/0279635 A1* | 9/2020 | Letterie | G16H 20/10 |
| 2022/0198657 A1* | 6/2022 | Hall | G06T 7/136 |
| 2022/0361823 A1* | 11/2022 | Goldner | A61B 5/14514 |

OTHER PUBLICATIONS

Davidson, L., Boland, M.R., "Enabling pregnant women and their physicians to make informed medication decisions using artificial intelligence." J Pharmacokinet Pharmacodyn 47, 305-318. (Year: 2020).*

Guvenir, H.A., Misirli, G., Dilbaz, S., et al., "Estimating the chance of success in IVF treatment using a ranking algorithm," Med Biol Eng Comput 53, 911-920 (Year: 2015).*

International Search Report and Written Opinion dated Oct. 20, 2023 regarding International Application No. PCT/US2023/027883; 10 pp.

* cited by examiner

Receive Clinical Data
210

Receive Selection
220

Communicate
Selection 230

Communicate
Content 240

Receive Outcome
250

Reinforce 260

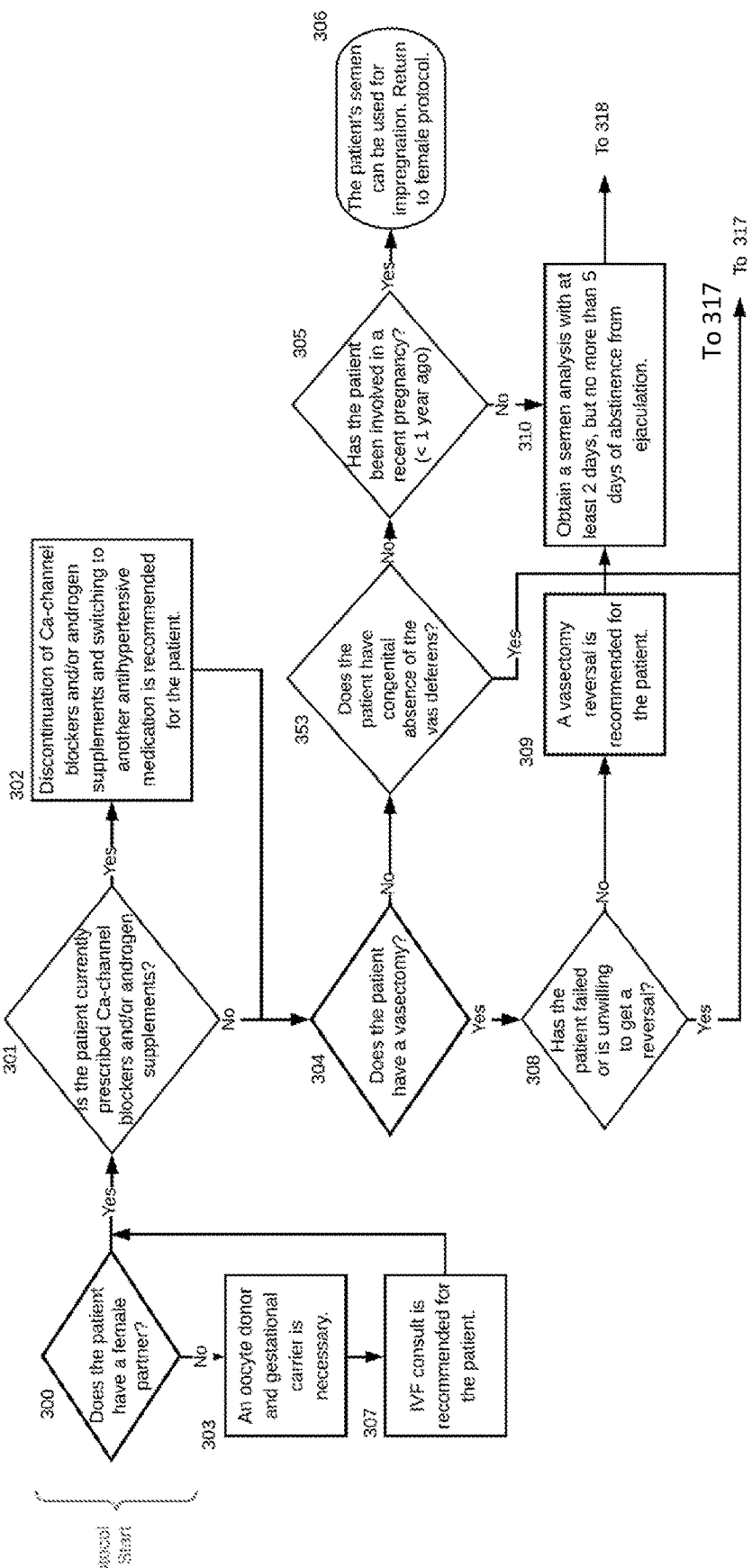
FIG. 3 Part A

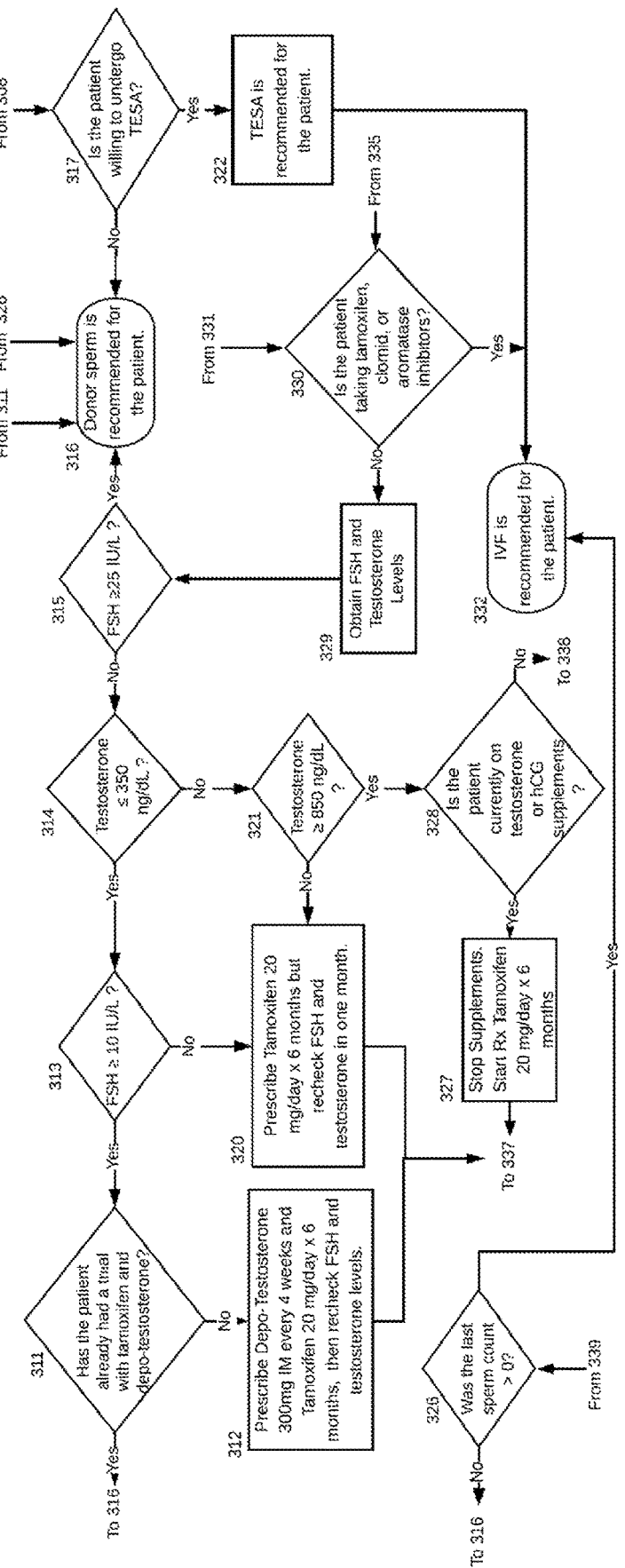
FIG. 3 Part B

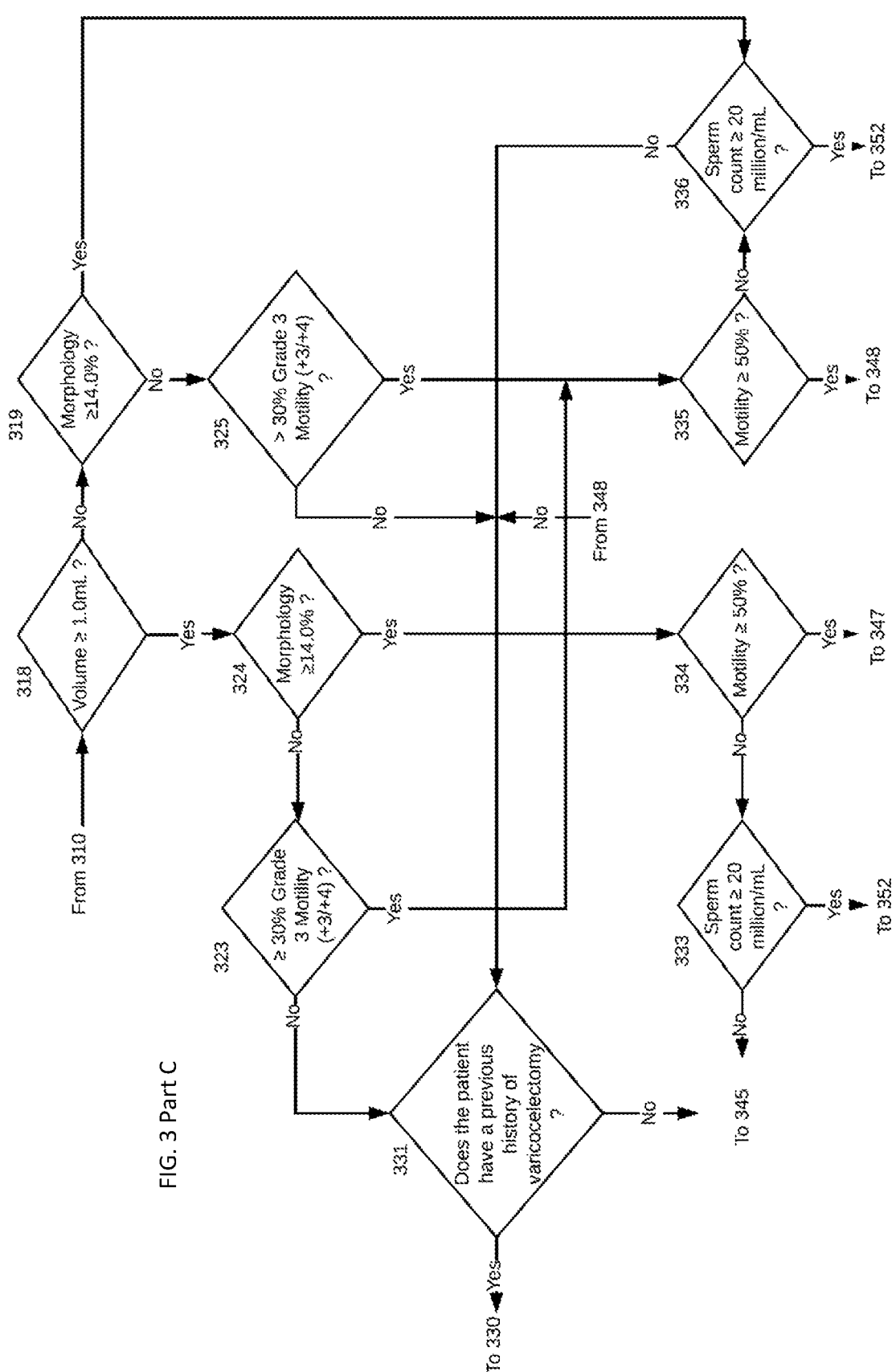
FIG. 3 Part C

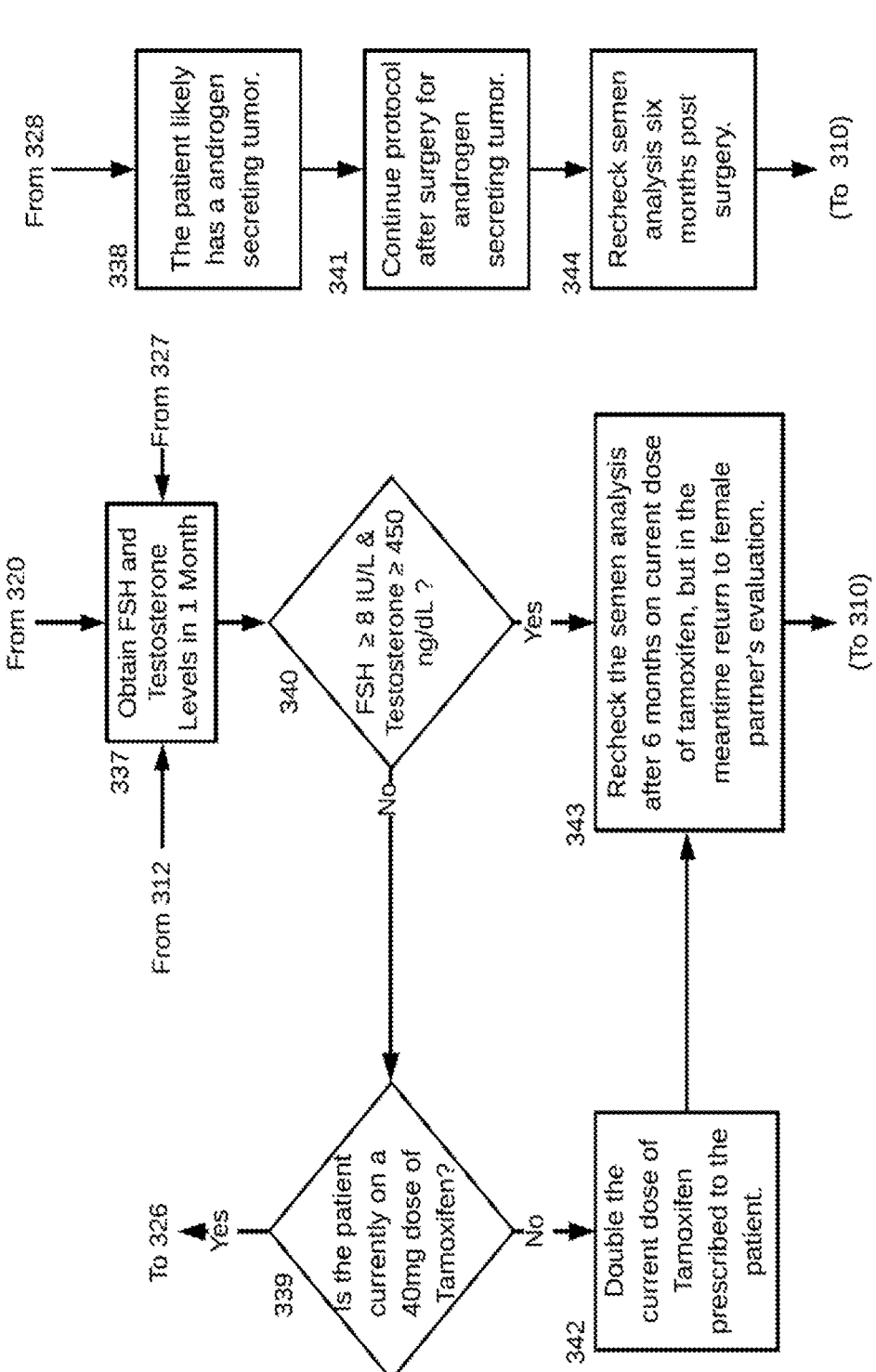
FIG. 3 Part D

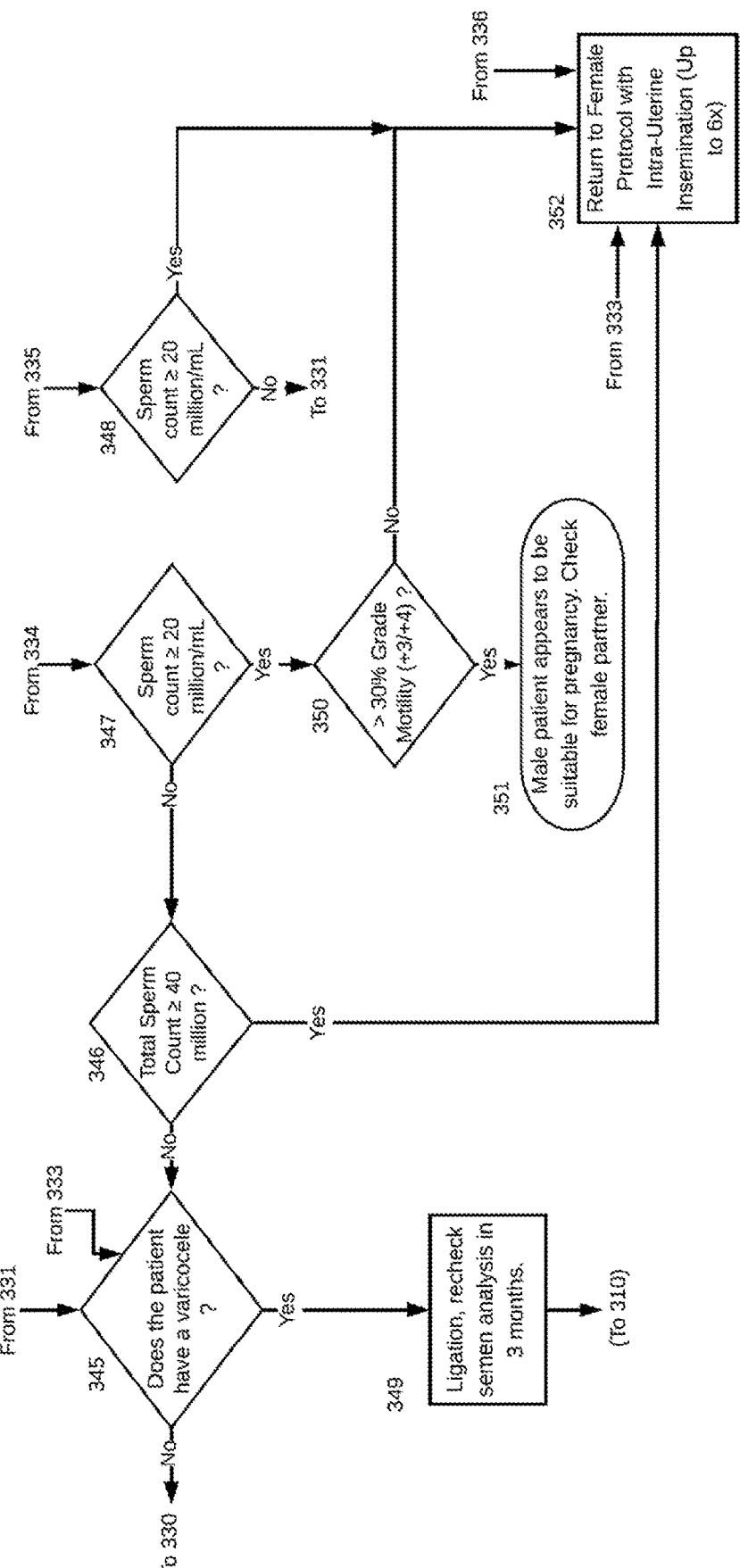
FIG. 3 Part E

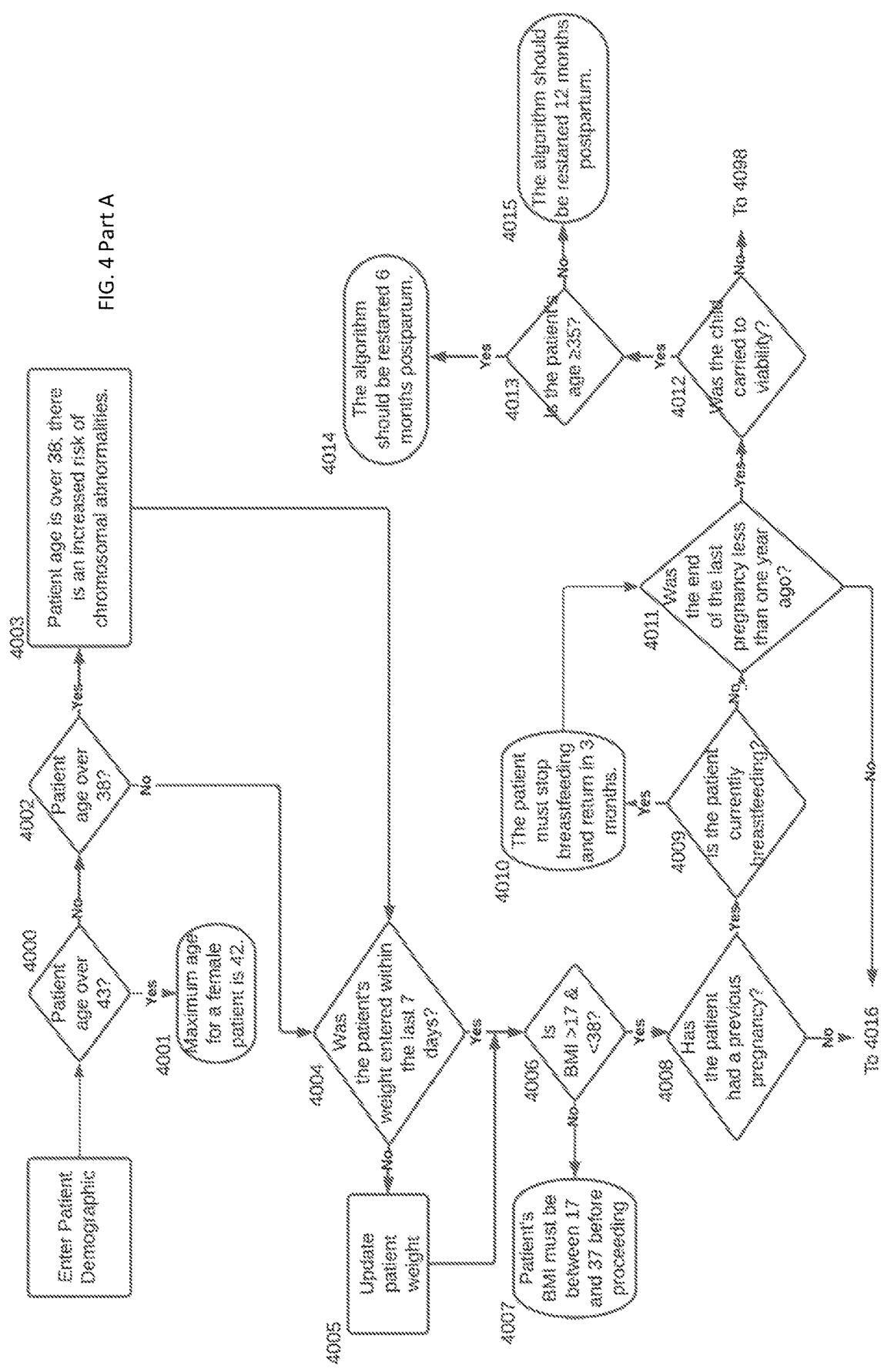
FIG. 4 Part A

FIG. 4 Part B
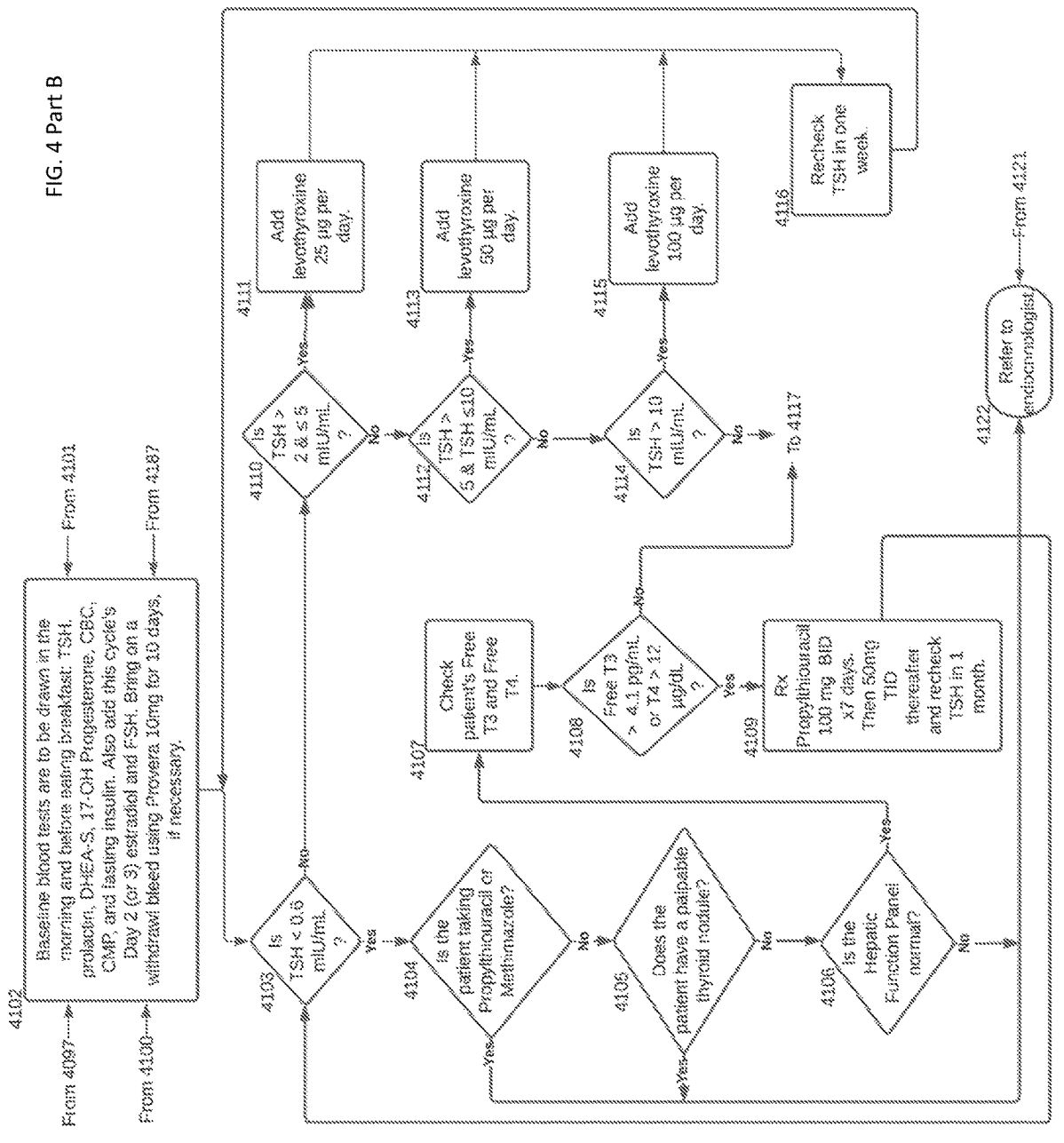

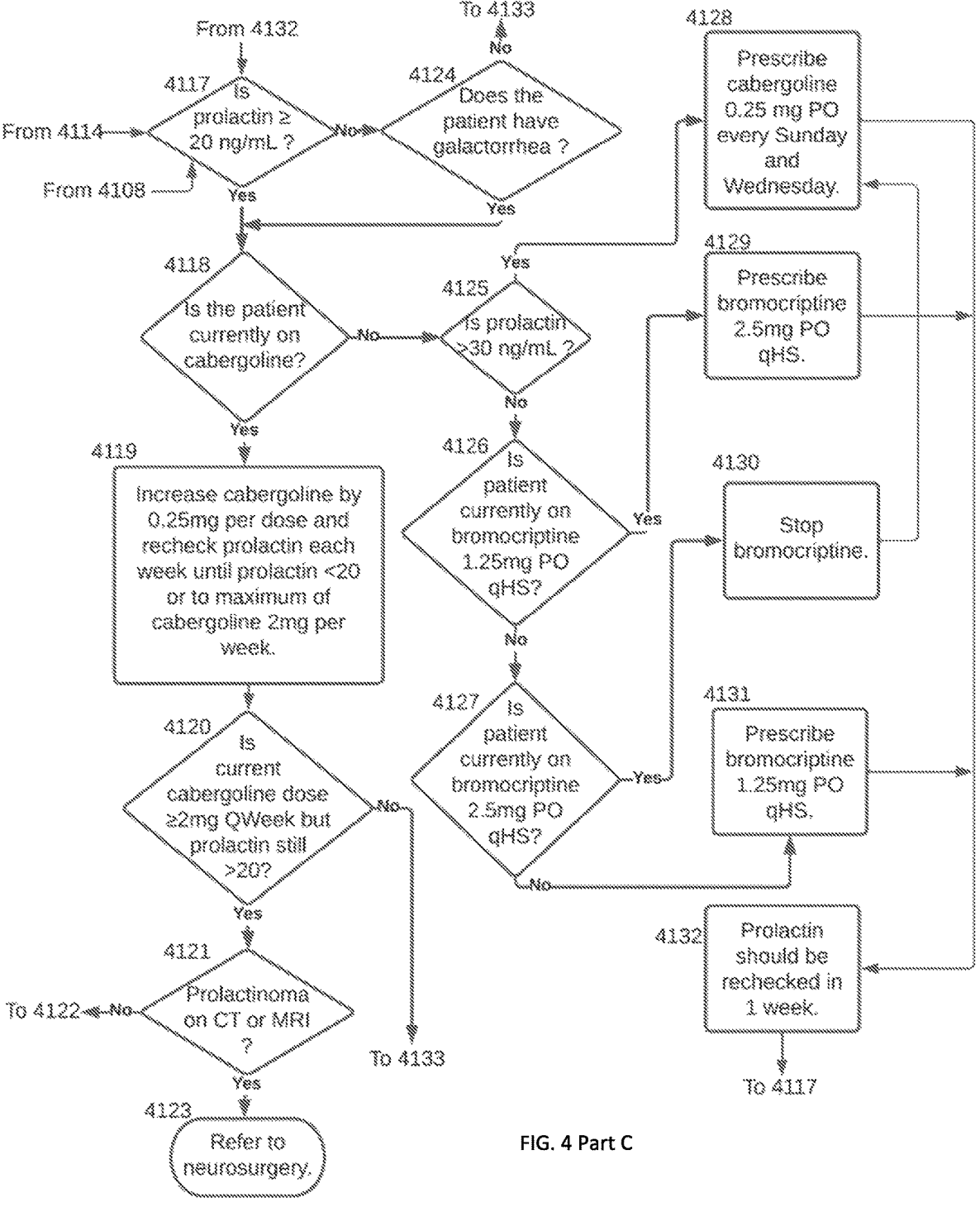
FIG. 4 Part C

FIG. 4 Part D
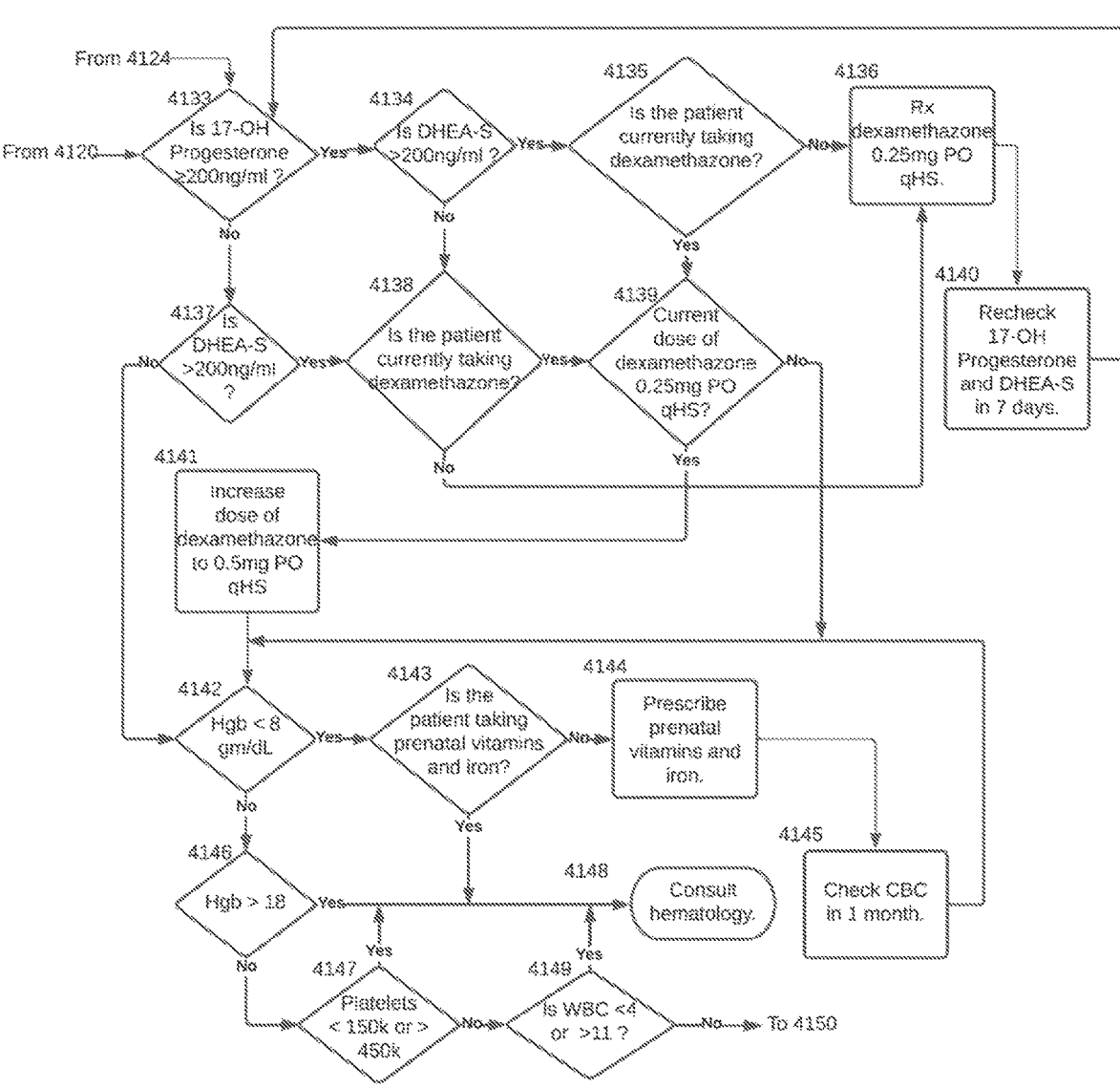

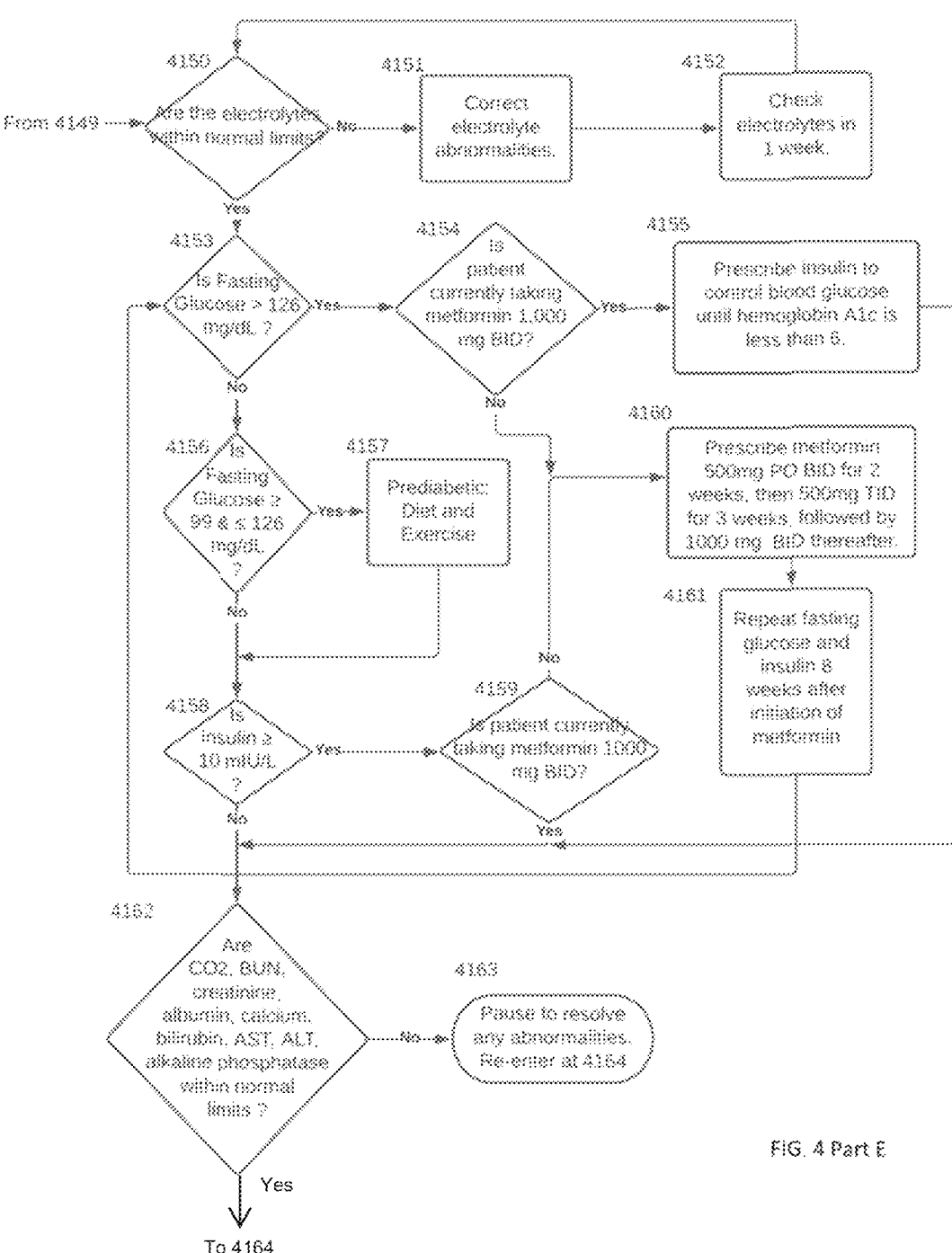
FIG. 4 Part E

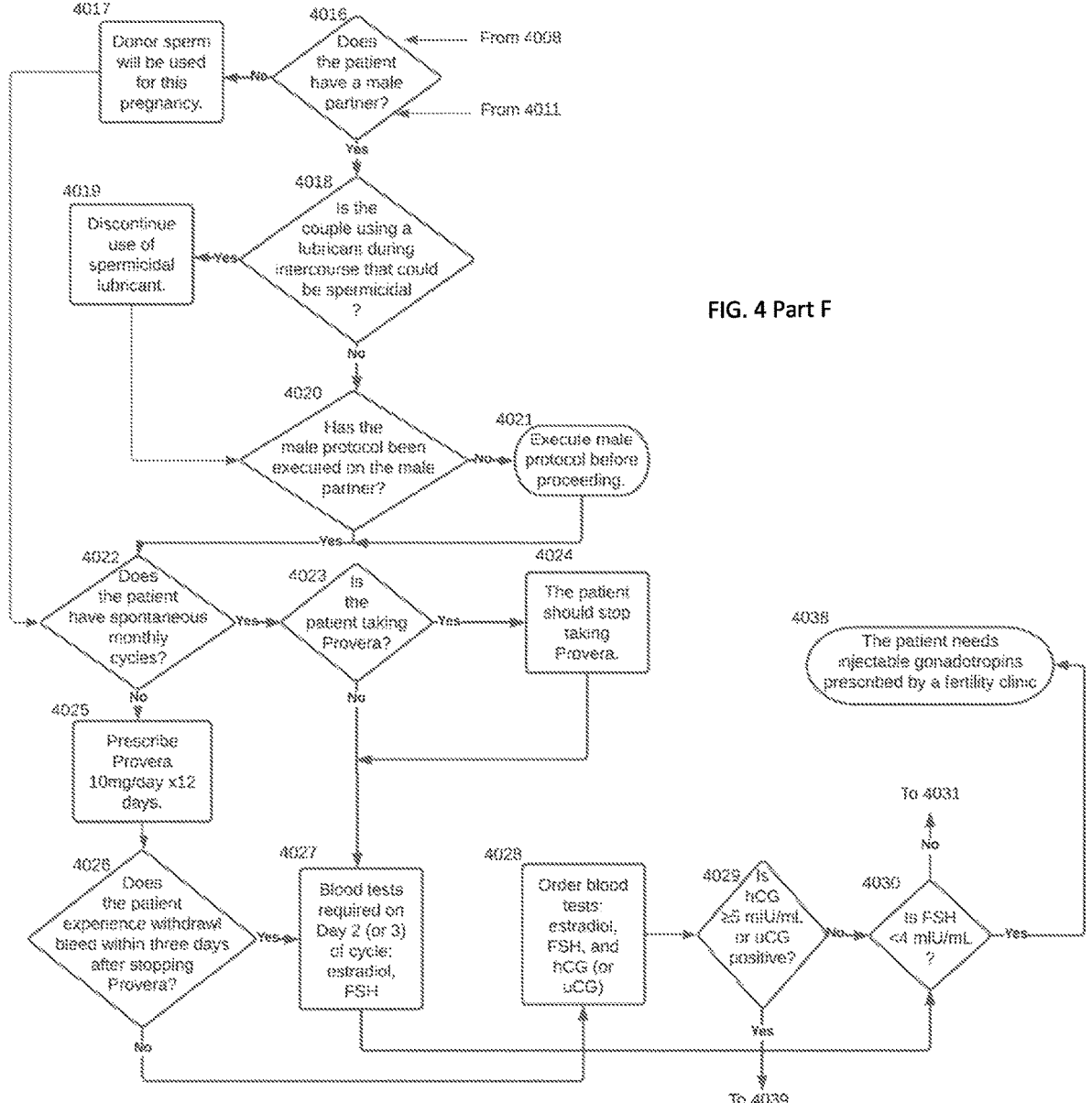
FIG. 4 Part F

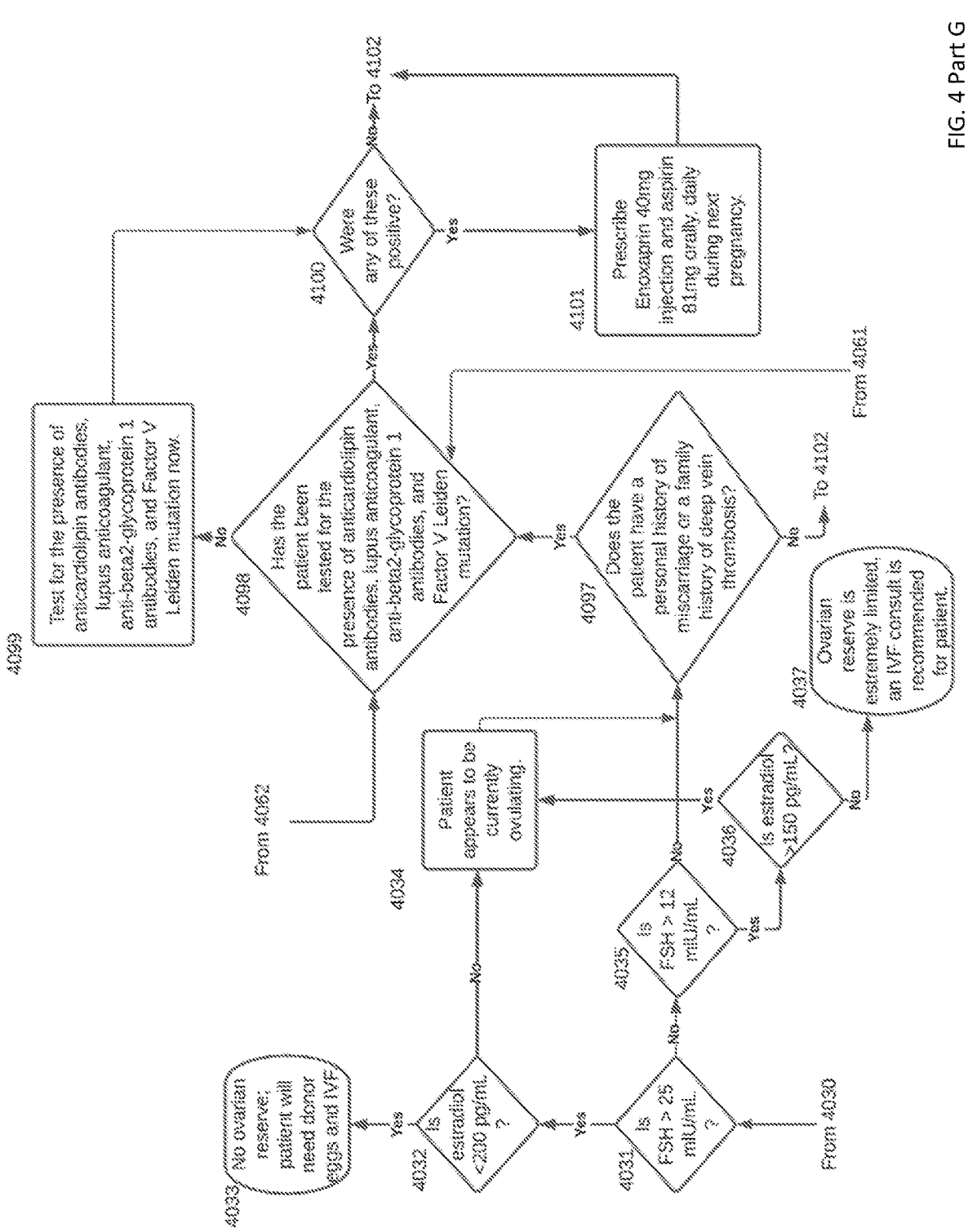
FIG. 4 Part G

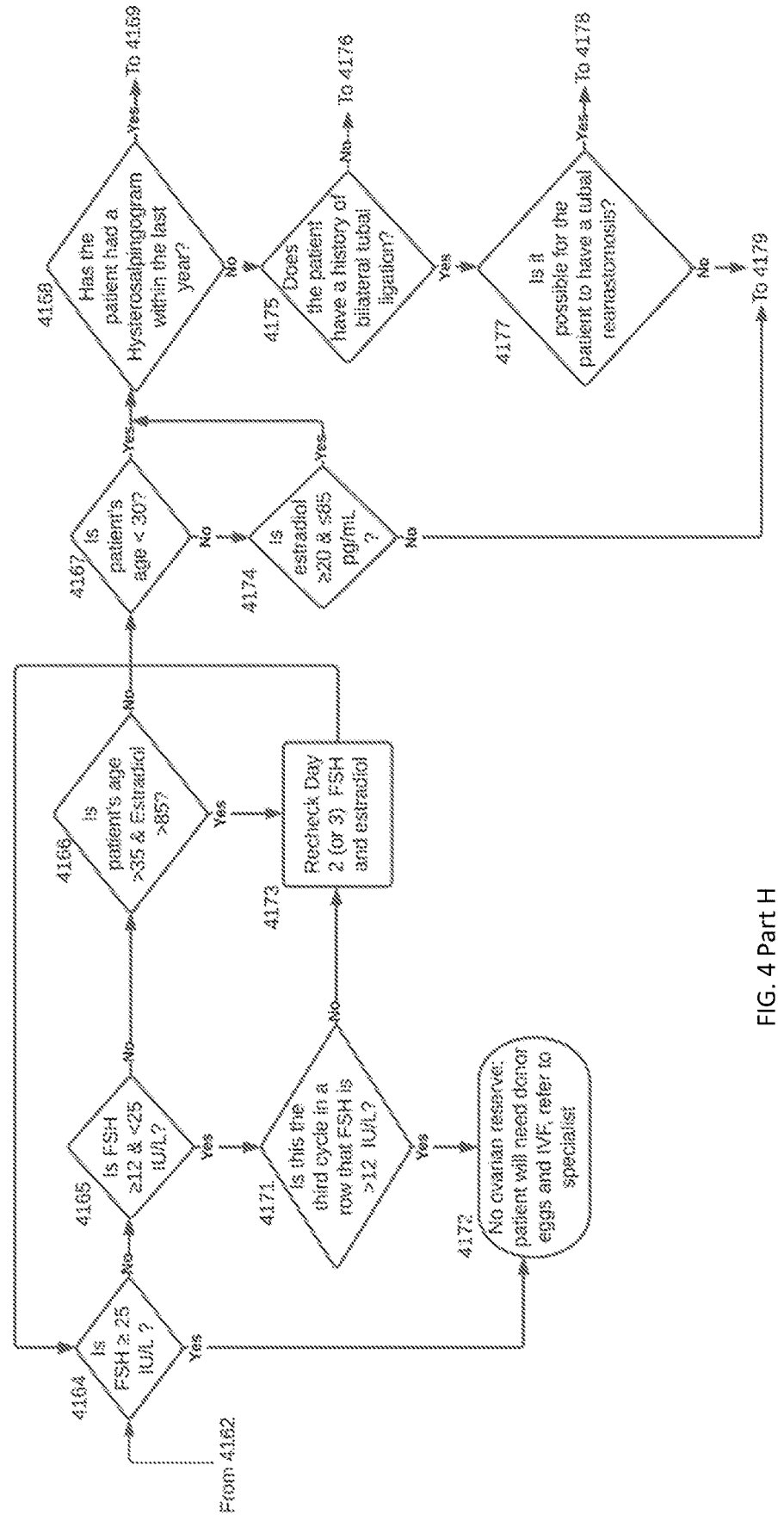
FIG. 4 Part H

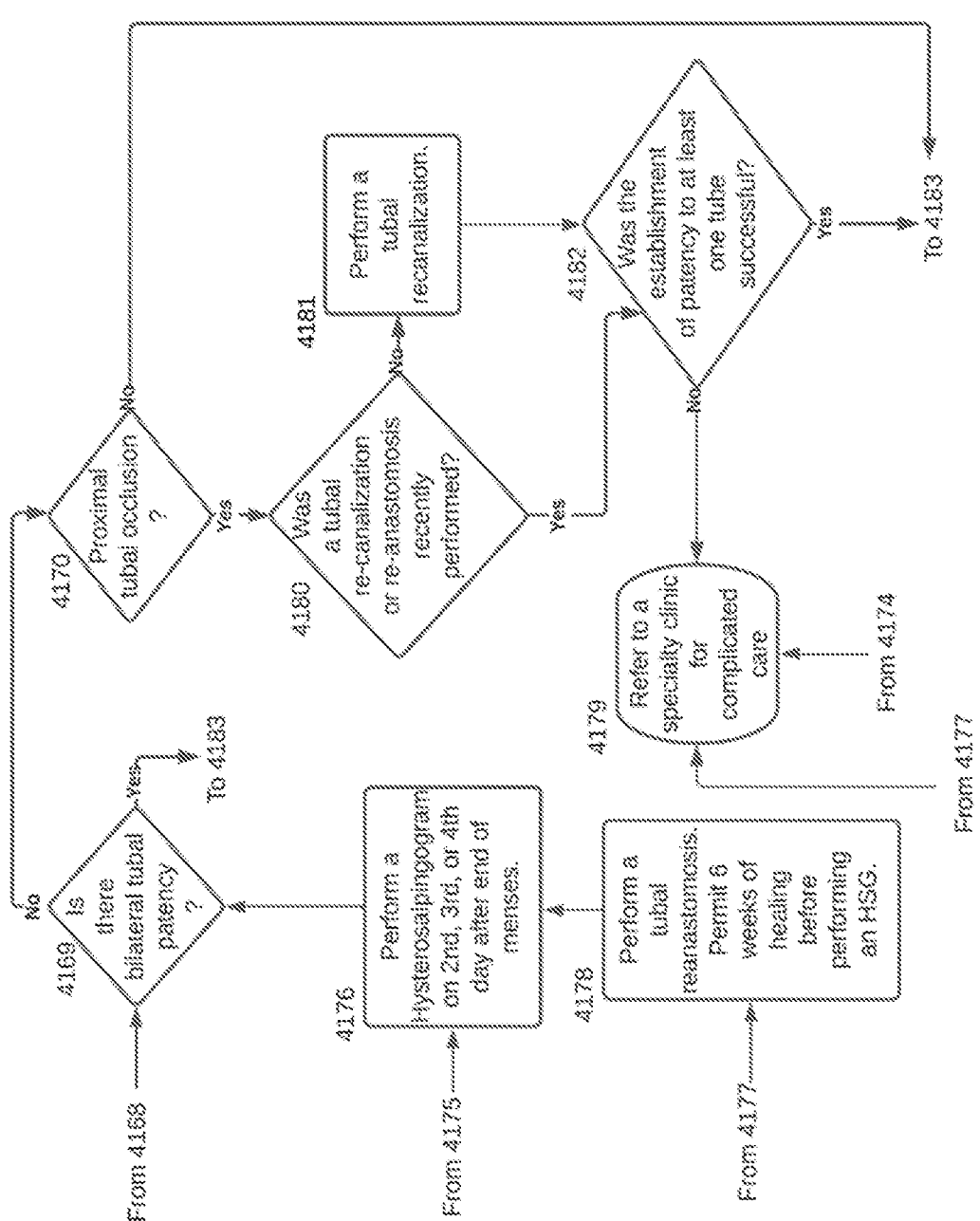
FIG. 4 Part I

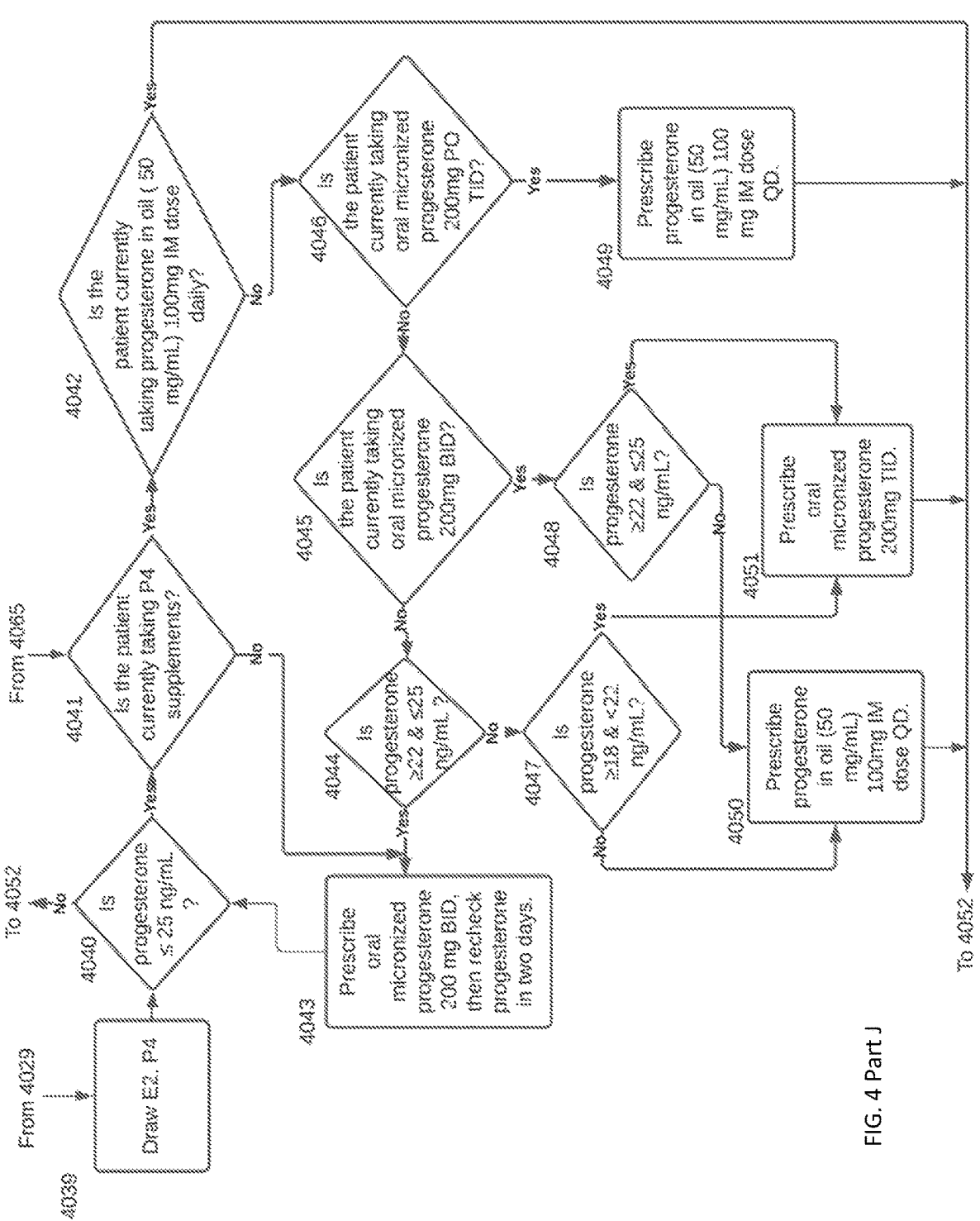
FIG. 4 Part J

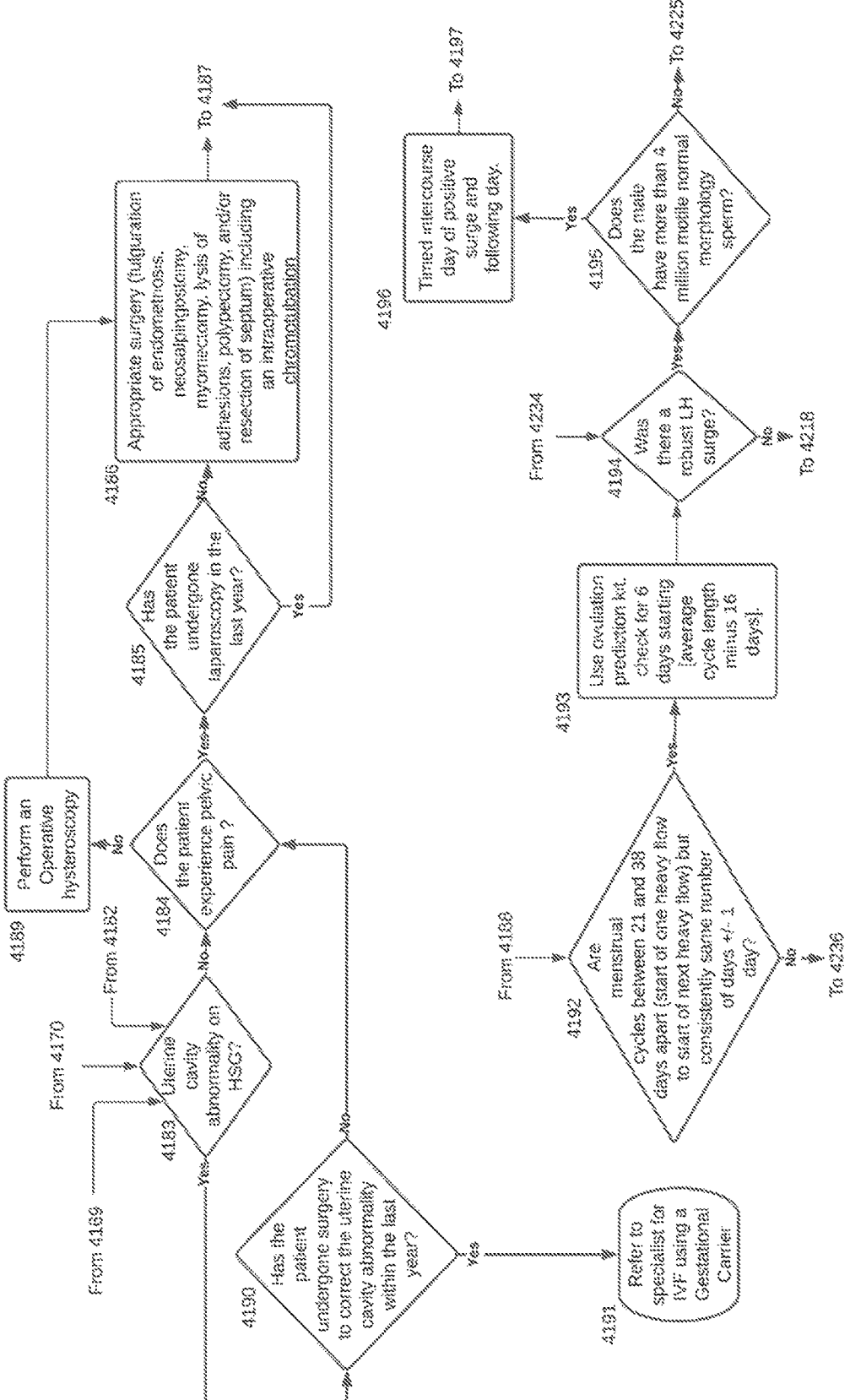
FIG. 4 Part K

To 4102
No

4187 — Has the patient had baseline blood tests drawn within the last year?

From 4186

From 4165

4183 — Resume diagnosis and treatment pathway 8 weeks post-operatively

To 4192

From 4210
From 4212
From 4214
From 4216
From 4217

4199 — Patient currently prescribed estradiol 2 mg BID?

Yes

4201 — Prescribe oral micronized estradiol 2mg PO BID now (and in future cycles beginning 2nd day after the LH surge or hCG trigger injection.)

4200 — Is estradiol > 150 pg/mL

No
Yes

4202 — Onset of menses less than 14 days following LH surge or hCG injection?

Yes → To 4203
No → To 4204

To 4207
No

4198 — Is progesterone > 15 ng/mL ?

Yes

From 4186

4197 — Check estradiol and progesterone levels one week later.

4224 — Prescribe hCG 10,000 U IM to trigger ovulation

4223 — Dominant follicle ≥ 17mm ?
Yes
No → To 4227

4222 — Pelvic ultrasound to measure the dominant ovarian follicle.

From 4221

4225 — Intra Uterine Insemination day after positive surge (or hCG trigger injection)

From 4195

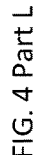

FIG. 4 Part L

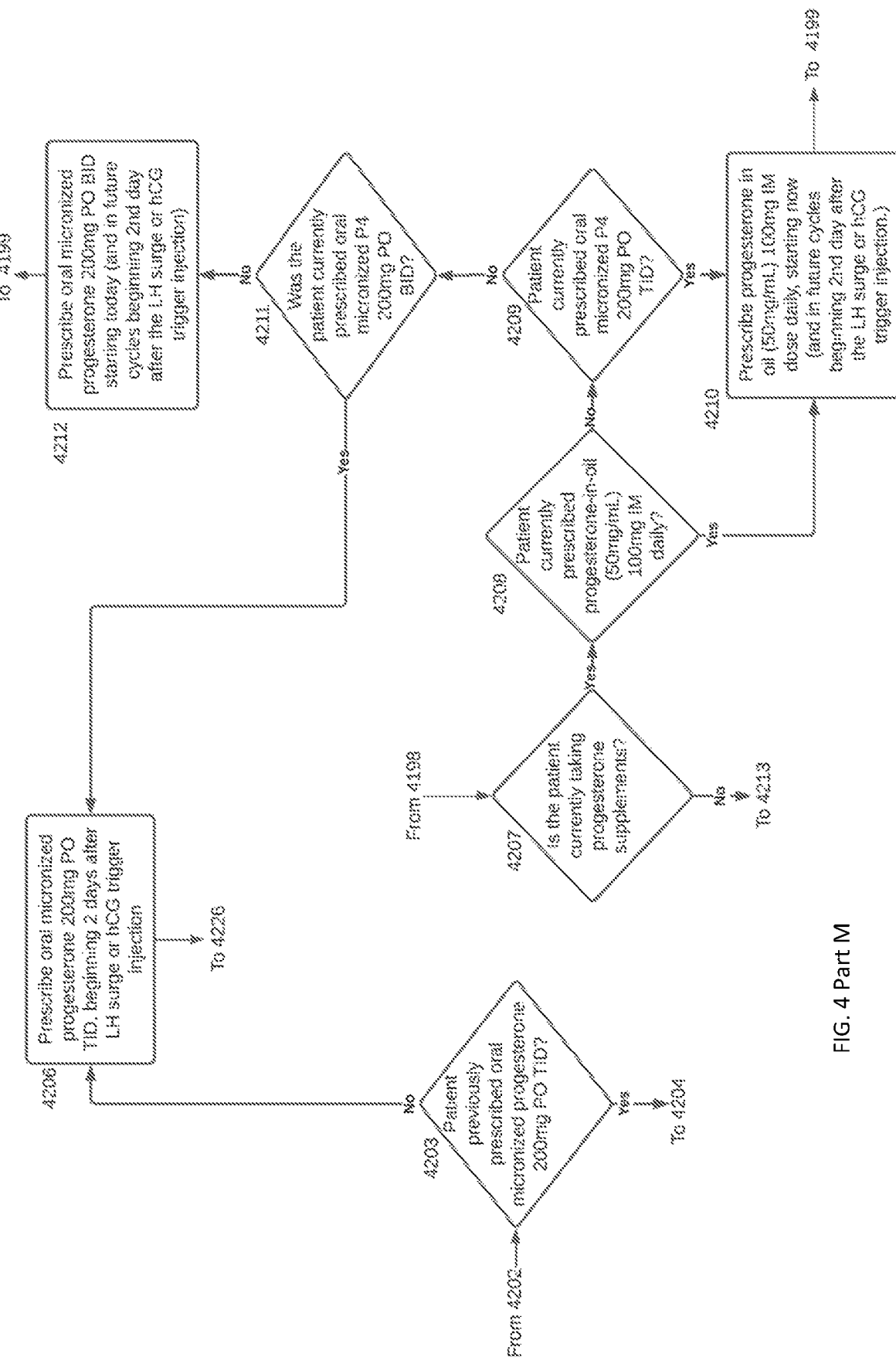
FIG. 4 Part M

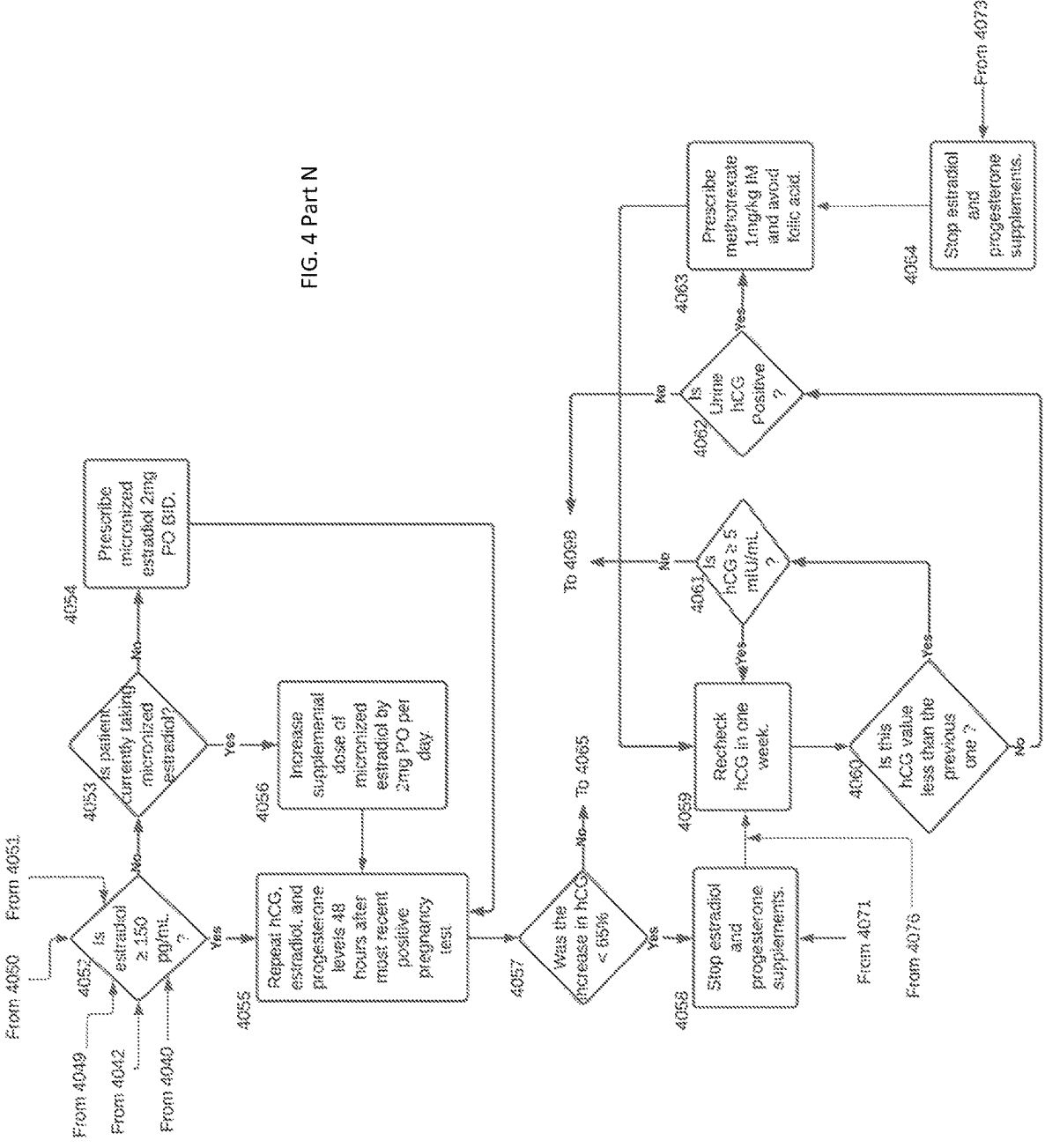
FIG. 4 Part N

Figure 4:
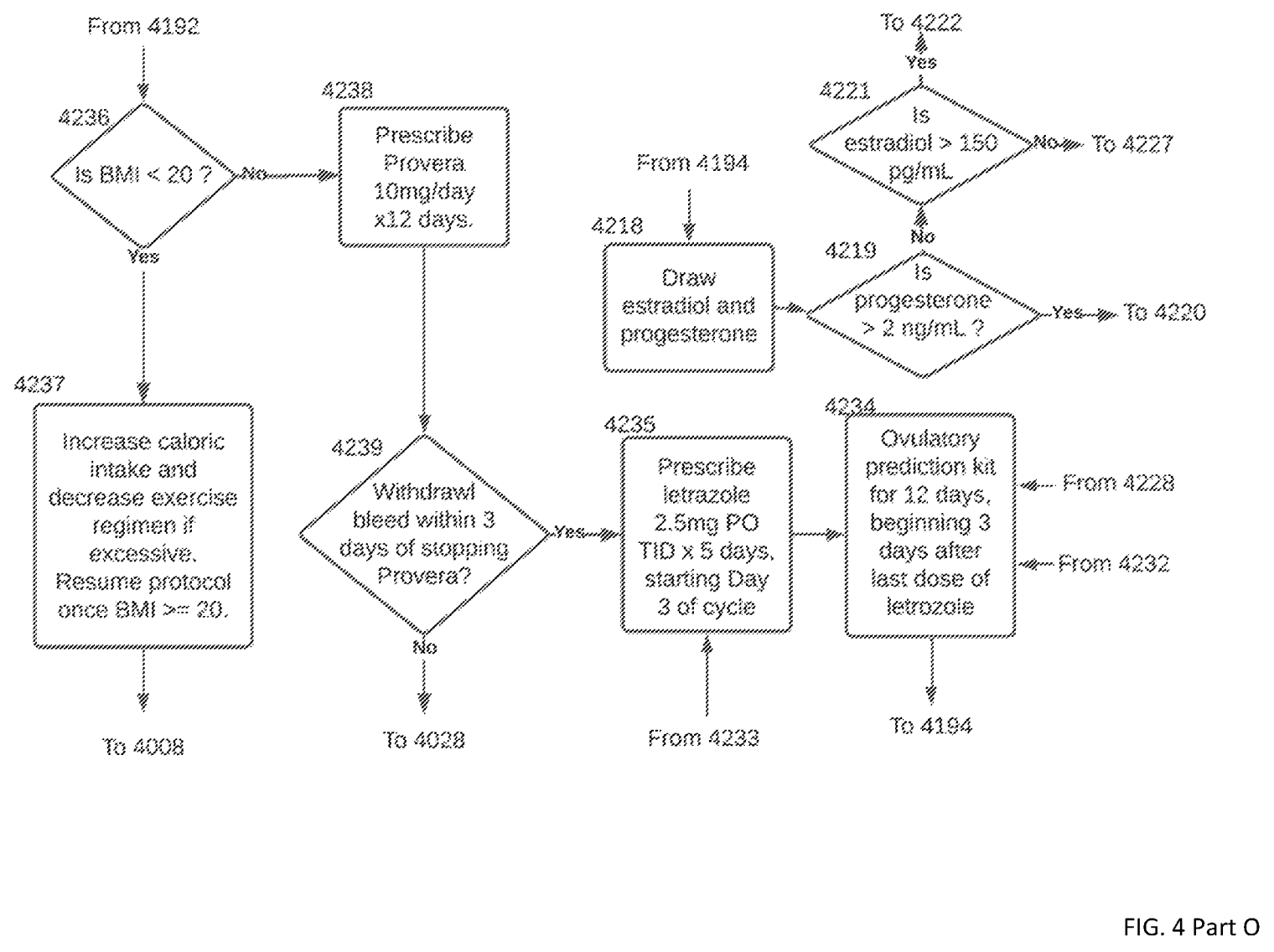

FIG. 4 Part O

To 4222
Yes

4221
Is estradiol > 150 pg/mL ?
No → To 4227

From 4194 →
4218
Draw estradiol and progesterone

4219
Is progesterone > 2 ng/mL ?
Yes → To 4220

4234
Ovulatory prediction kit for 12 days, beginning 3 days after last dose of letrozole
From 4228
From 4232
→ To 4194

4235
Prescribe letrazole 2.5mg PO TID x 5 days, starting Day 3 of cycle
← From 4233

4238
Prescribe Provera 10mg/day x12 days.

4239
Withdrawl bleed within 3 days of stopping Provera?
Yes
No → To 4028

From 4192 →
4236
Is BMI < 20 ?
No
Yes

4237
Increase caloric intake and decrease exercise regimen if excessive. Resume protocol once BMI >= 20.
→ To 4008

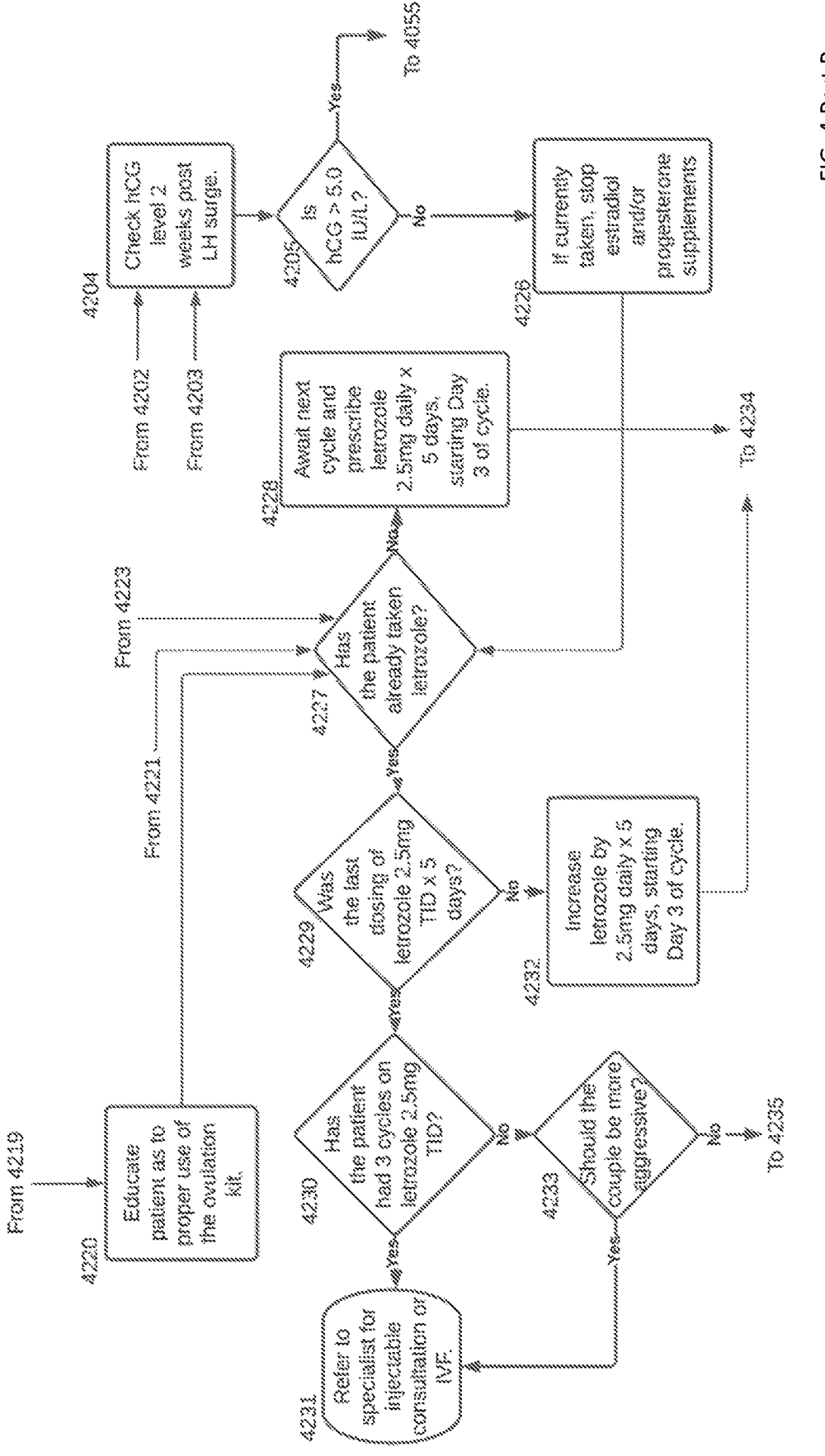
FIG. 4 Part P

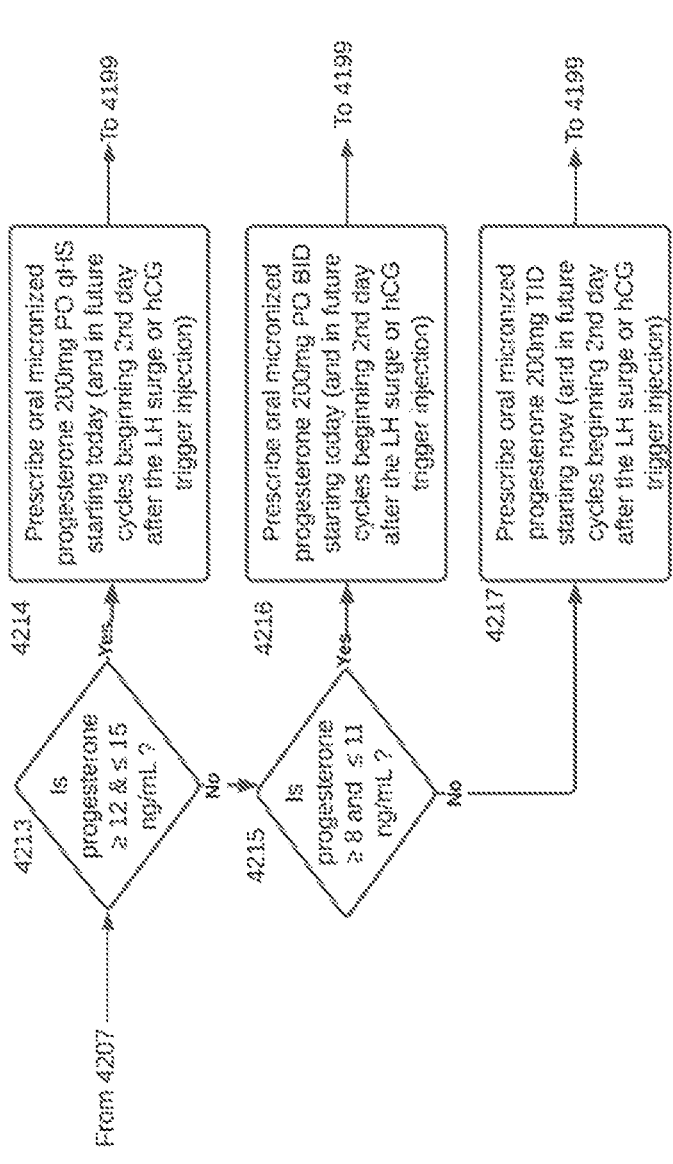
FIG. 4 Part Q

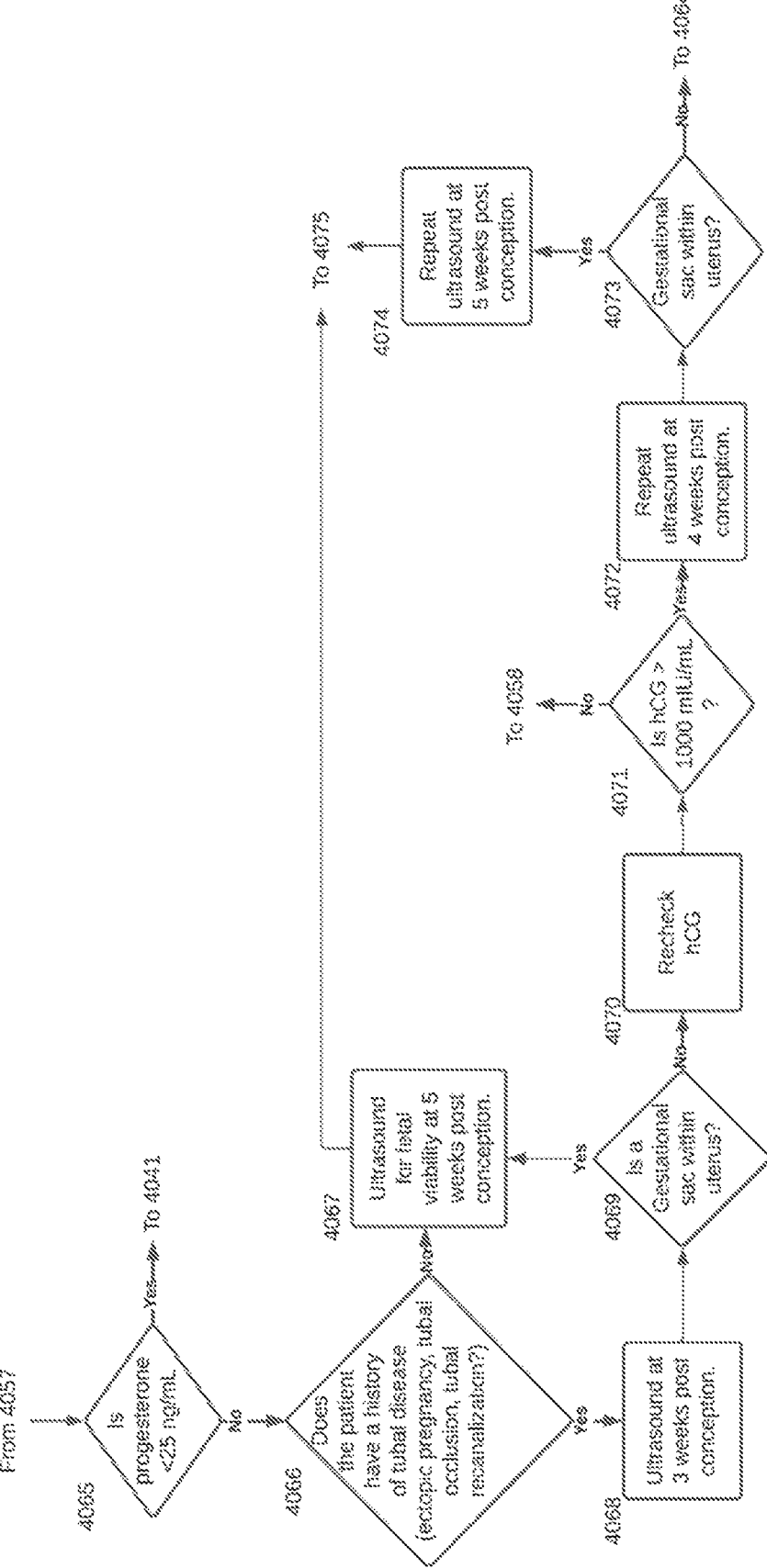
FIG. 4 Part R

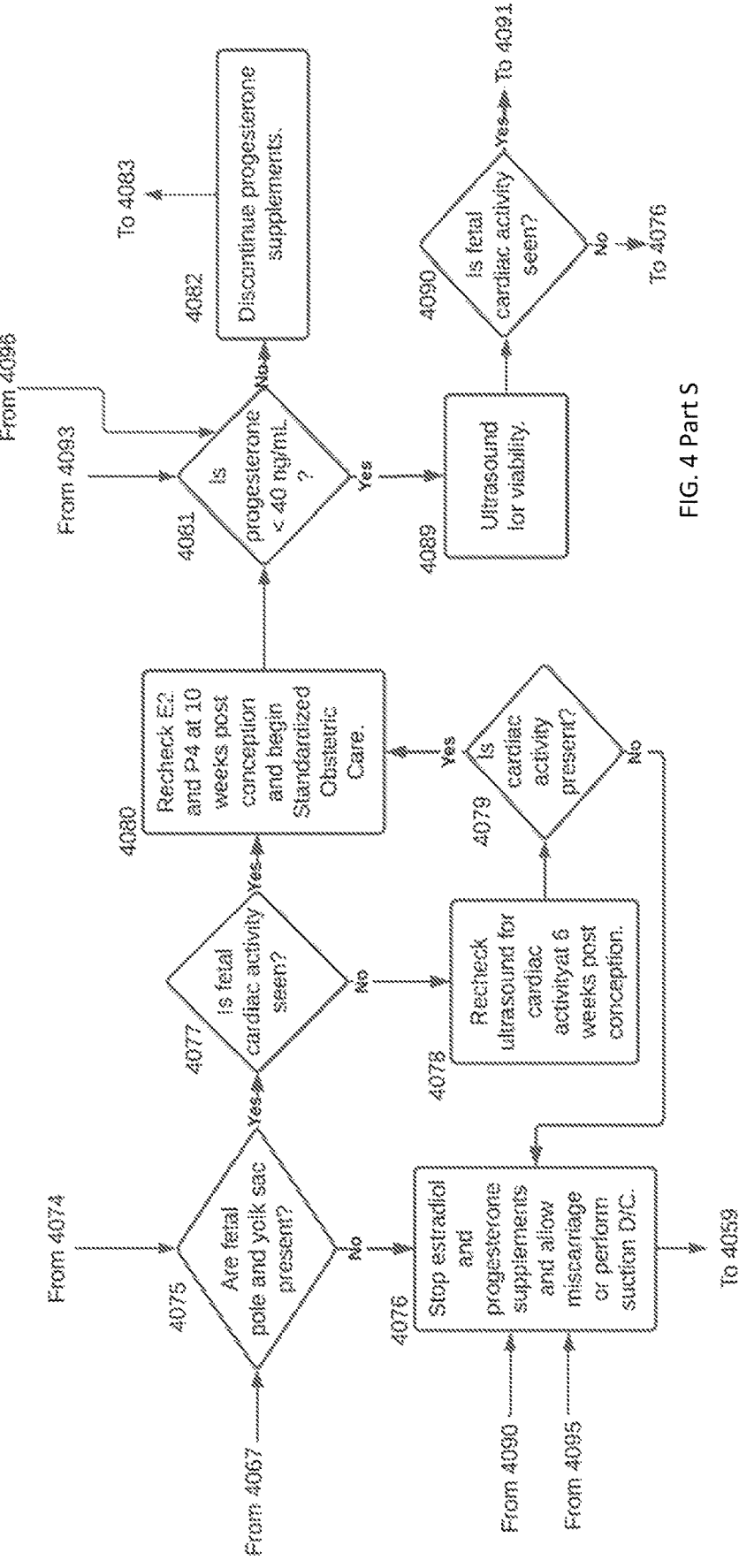
FIG. 4 Part S

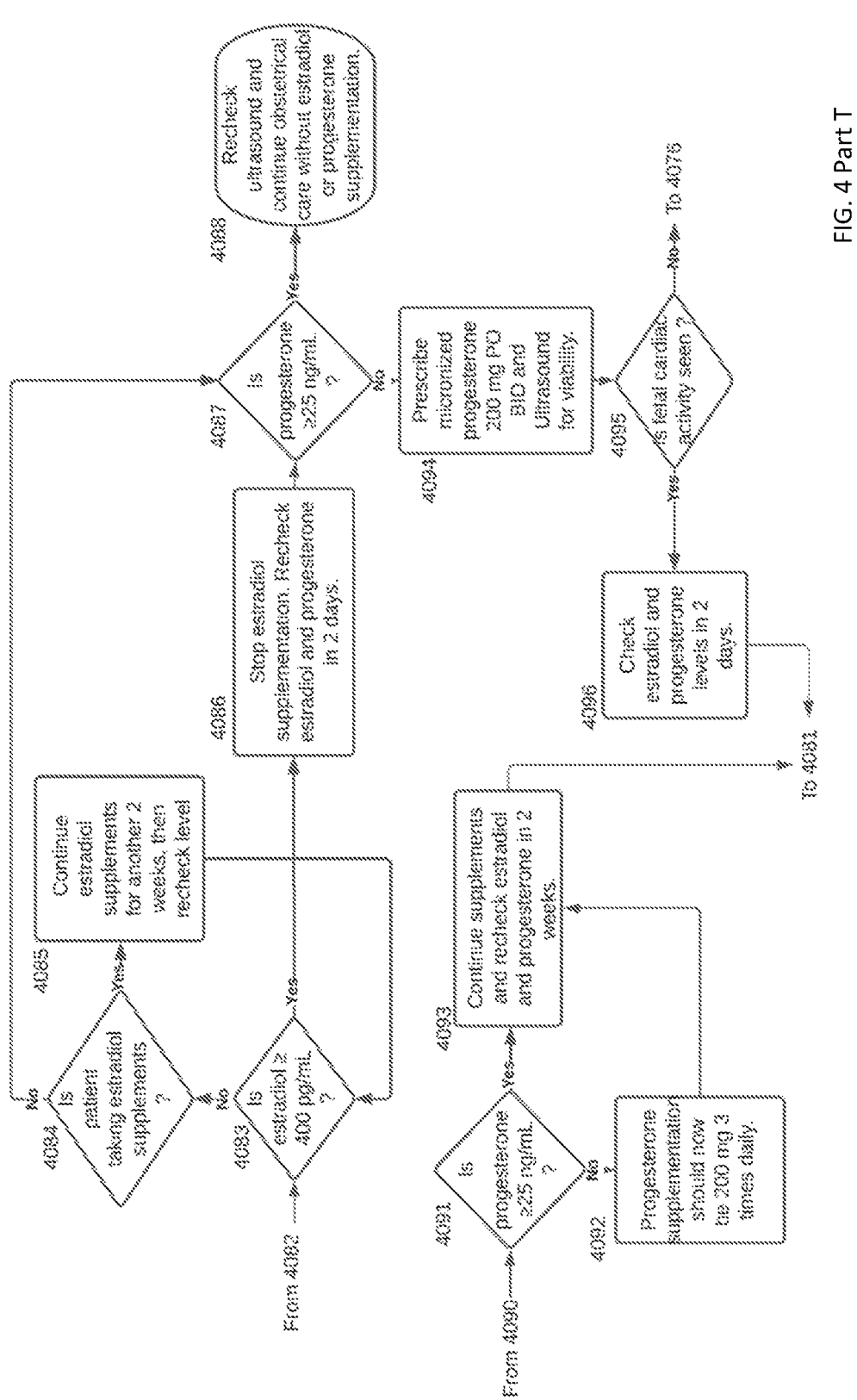
FIG. 4 Part T

MODERATED COMMUNICATION SYSTEM FOR INFERTILITY TREATMENT

CROSS-REFERENCE TO RELATED APPLICATIONS

This application claims priority to and benefit of U.S. provisional patent application Ser. No. 63/389,918 filed Jul. 27, 2022, the disclosure of which is hereby incorporated herein by reference in its entirety.

BACKGROUND

Field of the Invention

The invention is in the field of fertility treatment, and in some embodiments in the field of communication management for the optimization of fertility treatment.

Related Art

Fertility treatment is an area of medicine in which expertise is concentrated in a few locations and practitioners. It is, therefore, difficult for most patents to receive optimum care.

SUMMARY

The systems and methods of the invention provide several improvements directed at fertility treatment. These improvements include an expert/AI system configured to guide a caregiver, e.g., a physician, through the process of providing fertility treatment. They also include a communication system between the caregiver and a patient, which is moderated by the expert/AI system.

The expert/AI system (hereafter referred to simply as the "expert system") can include a traditional rules-based expert system and/or a machine learning system, the machine learning system including neural networks and/or knowledge graphs.

The communication system is configured to provide patients with appropriate information customized to their particular medical circumstances. For example, the communication system may provide documents and/or other information to patients to preemptively answer questions that they would otherwise direct at their caregiver. The information provided may be selected, at least in part, by the expert system, and may be responsive to the medical circumstances of the patient, e.g., to lab tests or other medically relevant characteristics.

Patients experiencing difficulties with conception and/or carrying a fetus to delivery, otherwise known as infertility, may often have a large number of potential anatomic or hormonal anomalies that can occur in either the man or the woman. The Fertility Basics Applications are a linked app system which facilitates a primary care provider of human healthcare to work up a couple with fertility issues. At its most fundamental level, human fertility management involve a male and female source of gametes and a medical provider managing the production and utilization of these gametes.

The two apps in the Fertility Basics system include a Provider app (FB-Pro) and a Patient app (FB-Patient). The provider app guides a medical provider through the evaluation and management of fertility issues in both males and females. The Patient app is an interactive app to the Provider app which allows for enhanced communication between providers and patients. The Patient app will not work without a link to the provider app.

FB-Pro contains an algorithm that walks a medical care provider through the workup and treatment of both male and female fertility issues. There is a standardized medical workup of fertility problems recognized in the medical literature [reference]. However, this workup is basic in nature and the success of this treatment in achieving a pregnancy is reportedly 28%.

The FB-Pro algorithm is an expanded workup which is significantly more successful in achieving and maintaining pregnancies. It is based on more than 25 years of clinical experience and medical literature which has been overlooked or underutilized by the healthcare industry in the United States. The steps of the protocol are all within normal medical care standards.

The barriers for primary care providers (PCP) to enter into treatment of fertility issues are many; however, the biggest two issues are knowledge base and time. This has created a sub-specialty that is focused on fertility management. This sub-specialty has focused on a procedure heavy approach to fertility management. Our system favors a medical management approach. FB-Pro addresses the knowledge gap that is present in the medical community on fertility management. The FB-Patient app provides information to the individual or couple seeking care to answer the questions they may have over why steps are being taken, what the steps will inform the team of, how to interpret the results and what the next step in the evaluation will be. The Patient App reduces the burden of communication that can prevent the normal functioning of a PCP's office while enhancing the communication between provider and patient of medical information that is desired by the patient or patients.

The Fertility Basics system collects data while progressing through the algorithm and the provider/patient interactions to track incident data. The causes for fertility problems in the US are generally known but incident data is sparse. Data collection allows for refining of this information. Definitions of medical terms are imprecise which impedes machine learning. This has limited the ability of researchers and other interested parties from mining the medical literature and standardizing medical care. The Fertility Basics system uses standardized definitions that provide stability for research purposes and interpretation of results. Initial statistical analysis will be descriptive and will progress to interpretive as data accumulates.

Descriptive statistics allows for a greater understanding of the true causes of reduced fertility in a population. Interpretive statistics allows for machine learning. Given the current state of the medical literature, the collection of descriptive statistics is a necessary precursor to useful machine learning.

Infertility is an anxiety producing condition for couples trying to conceive. Infertility is a disease that often can't be treated in rural areas. Infertility forces couples in rural areas to travel long distances to receive treatment from specialists. Currently, infertility is typically managed by expensive and invasive in vitro fertilization procedures. Couples undergoing these procedures must be highly motivated and are often far away from support networks at the time of treatment. Despite these challenges, current products on the market offer little assistance in helping infertile couples manage their condition, set goals, and stay motivated.

Therefore, it would be highly desirable to provide a system and method for addressing the above-mentioned problems associated with obtaining fertility management treatment in rural areas, obtaining non-invasive alternatives to IVF. Specifically, it would be desirable to provide an integrated system that is easy to wear; can record and learn from data; is easy to learn and teach; and gives the patient a platform to view and share data, view long term trends, interact with a healthcare professional, and provide other methods for remaining motivated.

In some embodiments, the fertility management system is composed of a Patient App, a Caregiver App, and an Expert System. In some embodiments, the Patient App allows the patient to input data manually or automatically through a sensor and then sends that information to the Expert System storage and processing. In some embodiments, the Caregiver App allows the healthcare provider to input clinical findings and laboratory results which are then sent to the Expert System for storage and processing. The Expert System receives information from the respective apps, performs algorithmic computations, stores patient information, and sends information and counseling to the Patient App and diagnostic and treatment information to the Caregiver App.

In some embodiments, the Patient App has a user interface, sensor, and stores relevant clinical information. In some embodiments, the Caregiver App has a user interface, stores relevant clinical data, and can perform some computational operations. In some embodiments, the Expert System has memory, a processor, and can perform algorithmic computations and communicate with both the Patient App and Caregiver App. In some embodiments, the Expert System further comprises a machine learning algorithm, a patient predictive model, and a monitoring algorithm.

The Patient App and Caregiver App are downloaded onto the respective user's smartphone. In some embodiments, the apps may be downloaded onto the respective user's computer or tablet. In some embodiments, the apps may be streamed over a web browser. In some embodiments, the Patient App may be connected to a sensor that collects pertinent clinical data, displays it to the patient, and sends it to the Expert System. In some embodiments, the Expert System resides in a physical server. In some embodiments, the Expert System resides in a cloud server system.

In some embodiments, the frontend apps can communicate with the Expert System by wireless means such as infrared technology, Wi-Fi, cellular telephone technology, radio frequency technology, or Bluetooth technology or by means of a USB port.

In some embodiments, the Patient App connects to a sensor that can automatically collect patient information. In some embodiments, the sensor collects patient information when initiated by the patient.

In some embodiments, a method for managing infertility proceeds as follows. A healthcare provider registers and logs onto the Caregiver App. The provider then adds a patient and begins investigating a series of questions produced by the app, including a partner fertility profile. The investigation proceeds until a treatment recommendation is reached. After said treatment, the provider returns to the Caregiver App to record the results and continue consultation, if required.

In some embodiments, the Caregiver App allows the provider the ability to register and login. In some embodiments, the Caregiver App allows the provider the ability to add a new patient, update information about that patient (clinical data includes at least one of: patient age, patient race, patient height and weight, patient lab results—e.g. Hb1c, patient medical and surgical history, patient allergies, patient current medications, family history, patient birth history, reset the patient, or delete the patient.

In some embodiments, the Caregiver App has an "Options" tab that displays buttons for a dashboard, a list of patients, some information about the app, and a logout button. In some embodiments, the Caregiver UI has persistent buttons for Protocol, Demographics, Weight, and History along the bottom of the UI.

BRIEF DESCRIPTION OF THE DRAWINGS

FIG. 3 illustrates a typical diagnostic and treatment methodology for the male patient in a sub-fertile couple, according to various embodiments. FIG. 3 is shown in parts A-E.

FIG. 4 illustrates a typical diagnostic and treatment methodology for the female patient in a sub-fertile couple, according to various s embodiments. FIG. 4 is shown in parts A-T.

DETAILED DESCRIPTION

Figure 1:
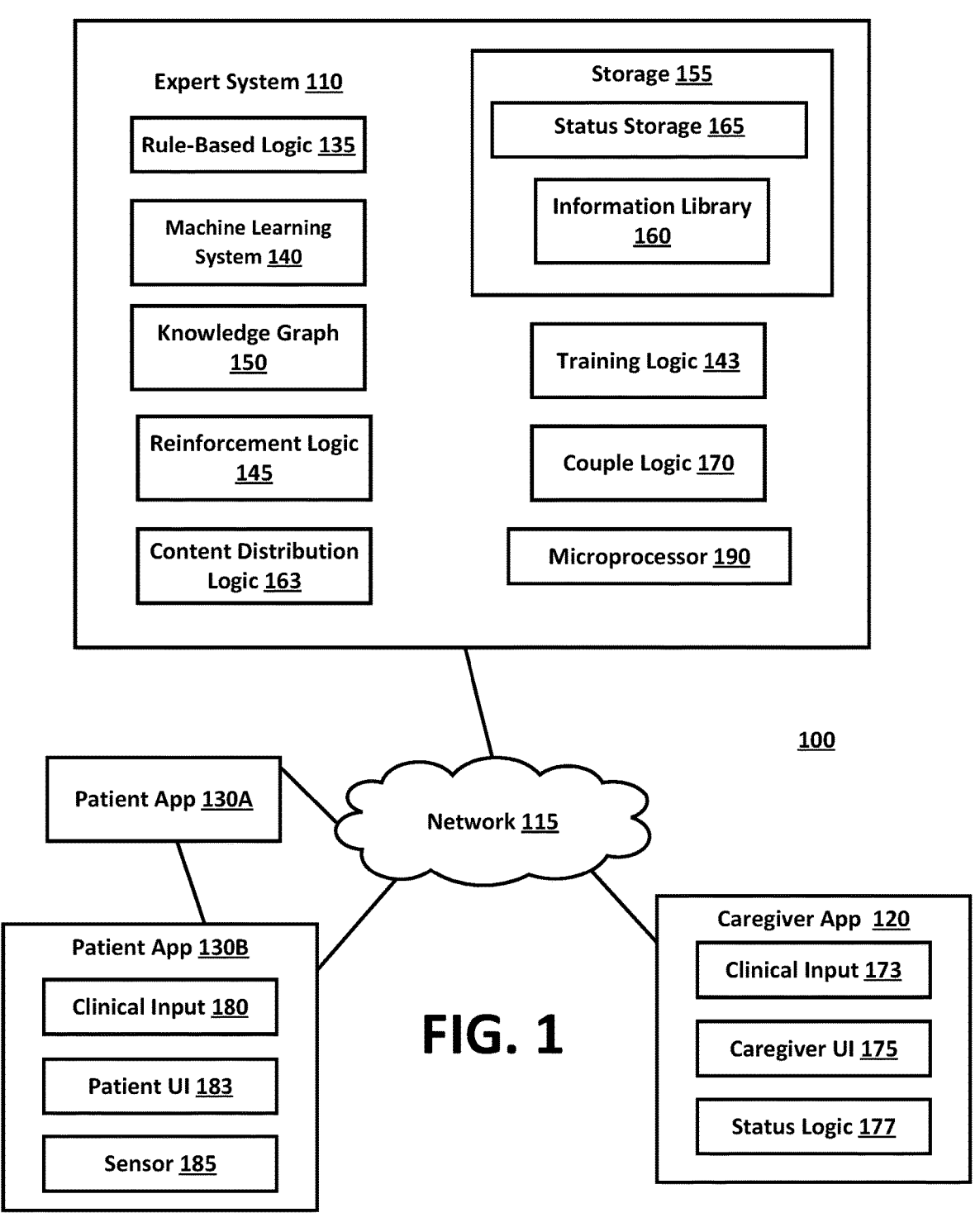
FIG. 1 is a block diagram of the internal elements of the backend server and frontend user interfaces illustrating a system configured for providing fertility treatment, according to various embodiments of the invention.

FIG. 1 illustrates System 100 configured for providing fertility treatment, according to various embodiments of the invention. System 100 can include an Expert System 110, one or more Caregiver Application 120 and one or more Patient Applications 130 (individually designated 130A, 130B, etc.). It is embodied in one or more computing devices, such as an internet-based server, it is configured to communicate over Network 115. The systems illustrated in FIG. 1 are configured to make selections for fertility treatments and for communicating between a caregiver and one or more patients.

In some embodiments, a fertility management system is provided that includes three interrelated components: Patient Apps 130, Caregiver App 120, and Expert System 110. These components interact with each other through the network 115.

The fertility management system includes three interrelated devices, i.e., a Patient app 130B, a Caregiver App 120, and Expert System 110. The Patient app 130B periodically or continuously takes information from the patient. The Patient App 130B transmits the information to the Expert System 110 via the network 115. The Expert System 110 receives patient information from both the Patient App 130B and the Caregiver App 120. The Expert System 110 performs algorithmic calculations and transmits information and instructions to the two apps. The Caregiver App 120 element periodically or continuously takes patient information from the healthcare provider. The Caregiver App 120 transmits the information to the Expert System 110 via the Network 115. In some embodiments, the communication between the apps and the server occurs over a wireless link. For example, infrared, Bluetooth, Wi-Fi, radio frequency, or cellular telephone networks can be used to transmit information between the Patient App 130B and Expert System 110 and Caregiver App 120 and Expert System 110. In other embodiments, the information can be communicated via wires, cables, or other physical means.

In some embodiments, the Caregiver App 120 contains a number of elements. In some embodiments, the Caregiver App 120 includes: Clinical Input 173, Caregiver UI 175, Status Logic 177. These elements are interconnected to receive information from the provider, communicate instructions to the provider, and perform calculations related to the status of the patient.

In some embodiments, the Caregiver App 120 component embodies a caregiver interface 175 element. In some embodiments, the caregiver interface 175 is touch sensitive to allow the provider to interact with the system by tapping, scrolling, or sliding a finger on the display screen. For example, in some embodiments, permanent buttons appear on the user interface allowing the user to view "Protocol," "Demographics," "Weight," and "History". In some embodiments, there are also dynamic buttons on the user interface allowing the user to "Reset Protocol," and "Add Feedback/Comment". All the information produced and collected is stored in the Status Storage 165 element of the Expert System 110.

In some embodiments, the Caregiver App 120 contains a Clinical Input 173 element. Clinical Input 173 contains information that can be uploaded to the Expert System 110 via Network 115. In some embodiments, the Clinical Input 173 element can be updated by information from the Expert System 110 through Network 115. In some embodiments, the back-and-forth communication can be done by wireless means such as infrared technology, Wi-Fi, cellular telephone technology, radio frequency technology, or Bluetooth technology or by means of a USB port.

In some embodiments, the Caregiver App 120 contains a Status Logic 177 element. In some embodiments, Status Logic 177 performs diagnostic calculations based on information inputted by the provider through Caregiver UI 175 and sends the results to the Clinical Input 173 element. In some embodiments, Status Logic 177 performs diagnostic calculations and sends the results back to the Caregiver UI 175 element to be displayed to the provider.

In some embodiments, the Caregiver App 120 contains a Caregiver UI 175 element. In some embodiments, Caregiver UI 175 receives information from the provider and sends said information to the Status Logic 177 element for calculation. In some embodiments, the Caregiver UI 175 sends said information to the Clinical Input 173 input for transmission to the Expert System 110 for processing and storage. In some embodiments, the Caregiver UI 175 provides instructions to the provider from the Expert System 110 or from the Status Logic 177. In some embodiments, a Caregiver User Interface is configured for a caregiver to receive the selections from among the alternative infertility treatments in Rules-Based Logic 135; in some embodiments the Caregiver UI is configured for a caregiver to receive selections derived from the Machine Learning System 140 according to a ranking and scoring assignment. In some embodiments, the Caregiver User Interface is configured for a caregiver to approve the selections, to forward the selections to the patient, to approve the content from the library of information, to forward the content from the library of information to the patient, to answer questions received from the patient, to require that the caregiver provide the clinical data, and/or to enter the clinical data.

In some embodiments, Status Logic 117 is configured to track the treatment including the selections from among the alternative infertility treatments along with tracking the treatment status of the patient. This includes treatments received and recorded in the treatment history.

In some embodiments, the fertility management system in FIG. 1 the Patient Apps 130 (i.e., Patient Apps 130A, 130B, 130C, etc.) component contains a number of elements. The patient applications are embodied in a patient computing device, wherein the patient applications include: a smartphone, a tablet, or personal computer.

In some embodiments, it includes a Patient App 130A which acts as a conduit to educate and inform the patient as to what the next step in the protocol will be and why it is necessarily the next step. It also informs the patient as to what their lab test results, and procedural findings are and what they mean.

In some embodiments, the Patient app 130B includes: the Clinical Input 180, Patient UI 183, and/or Sensor 185. These elements are interconnected to receive information from the patient, communicate counseling to the patient, and receive information from a sensor. In some embodiments, the Patient UI is configured to display the content from the library to the patient. In some embodiments, the Patient UI is further configured for the patient to enter the clinical data, to send questions to the caregiver, to require that the patient provide clinical data, and/or to display data generated by the sensor.

In some embodiments, the Patient App 130B includes a Clinical Input 180 element. In some embodiments, Clinical Input 180 receives information from the Expert System 110 over the Network 115 and sends it to the Patient UI 183 for display to the patient. In some embodiments, the Clinical Input 180 element receives patient information from the Patient UI 183 element and sends it to the Expert System for processing and storage.

In some embodiments, the Patient App 130B component contains a Patient UI 183 element. In some embodiments, Patient UI 183 receives information manually imputed by the patient to be sent to the Expert System 110 over Network 115. In some embodiments, the Patient UI 183 receives information automatically imputed by the Sensor 185 element to display to the patient and send to the Expert System 110. In some embodiments, the Patient UI 183 element can also receive counseling and other information from the Expert System 110 and display said information to the patient.

In some embodiments, the Patient App 130B component contains a Sensor 185 element. Sensor 185 receives information from a medical monitoring device and transmits said information either manually or automatically over Network 115 to the Expert System 110 for processing. In some embodiments, Sensor 185 receives information from a medical monitoring device and displays that information on Patient UI 183. In some embodiments, the sensor is a wearable medical device including but not limited to biosensors and implants. In some embodiments, the sensor is a medical monitor that is not wearable. Garnished data may include, but is not limited to vital signs, motion detection, sleep monitoring, anatomic findings and measurements via ultrasound, hormone levels, metabolic and biochemical markers, and various antibodies.

In some embodiments, the Patient App 130B may be downloaded onto the patient's smartphone. In some embodiments, the Patient App 130B may be downloaded onto the patient's computer or tablet. In some embodiments, the Patient App 130B may be streamed over a web browser. Similarly in some embodiments, the Caregiver App 120 may be downloaded onto the healthcare provider's smartphone. In other embodiments, the Caregiver App 120 may be downloaded onto the provider's computer or tablet. In other embodiments, the Caregiver App 120 may be streamed over the provider's web browser. In some embodiments, the Expert System 110 resides in a physical server. In other embodiments, the Expert System 110 resides in a cloud server.

In some embodiments, the Expert System 110 contains a number of elements. In some embodiments, the Expert System 110 contains one or more of the following: Rule-Based Logic 135, Machine Learning System 140, Knowledge Graph 150, Reinforcement Logic 145, Content Distribution Logic 163, Memory Storage System 155, Training Logic 143, Couple Logic 170, Microprocessor 190.

In some embodiments, the Rule-Based Logic 135 operates on premises and parameters currently proposed by experts in the field of infertility and/or their overseeing governing body. From this, a list of rules has been created and an inference engine performs a match-resolve-act cycle which measures information that it takes in against these rules.

In some embodiments, the Machine learning system 140 is configured to supplement the selections provided by the rule-based logic, and training logic configured to train the first machine learning system based on clinical success of the selections from among the alternative infertility treatments. Wherein the first machine learning system is further configured to provide a preference among selections provided by the rule-based logic, Machine Learning System 140 operates on an algorithm created by selecting an appropriate AI model and presenting it with a very large dataset. The algorithm then analyzes the dataset and determines relationships within that data; logic is then embedded in the algorithm, not encoded by a human. This model trains itself and learns from the data, creating a cohesive relationship between data inferences and future data outputs.

In some embodiments, the Knowledge Graph 150 can be the patient's accrued data entered into standardized graphs or graphs generated de novo using machine learning.

In some embodiments, the Reinforcement Logic 145 applies to when the software agent receives data as its sensory inputs and then acts on the environment by displaying on a screen, writing files, and sending network packets. It is configured to associate quality scores to members of the plurality of rules, the scores being based on at least clinical success of the selections. This embraces the three basic elements of Reinforcement Learning: Policy, which defines the way the agent behaves at a given time; Reward, which defines the goal of a learning problem as the maximizing of good (versus bad) results of that behavior; and, Value, the aggregated number of rewards expected by adherence to a refined policy. A fourth element germane to our system is the Model of the Environment, which implies that the behavior of an individual's reproductive environment (or milieu) will react in a manor favorable to a pregnancy. Feedback loops are at times quantitative and at times qualitative communicated from the Patient App 130B and/or the Caregiver App 120 to reinforce (raise score of) rules that seem to work while lowering rules that don't seem as good. These data are requisite in concurrence with their given step in the process or else progress halts In some embodiments, the Content Distribution Logic 163 refers to how data is managed and is configured to automatically provide content from the library of information to the first patient; optionally after approval by caregiver. The patient is informed of his/her data and what they mean in relation to their infertility as communicated through Patient UI 183 and is optimized to minimize questions to care giver. The caregiver receives feedback from Expert System 110 on Caregiver App 120 either through Caregiver UI 175 or Status Logic 177. In some embodiments the content distribution logic is configured to automatically provide content from the library of information to the first patient; optionally after approval by caregiver. In this manner the content distributed is optimized to minimize questions to care giver. A second machine learning system is trained on this goal. The Expert System 110 receives confirmation from both Caregiver UI 175 and, that content has been read by patient. In some embodiments, data is distributed elsewhere within each element of System 100.

In some embodiments, Storage 155 is configured to store a library of information regarding the alternative infertility treatments and the clinical data regarding the first patient, the storage including non-transient digital memory, and a patient Status Storage 165 containing pertinent positive and negative clinical data regarding the individual patient including non-transient digital memory. Storage 155 could store any of the logic discussed herein.

In some embodiments, there is an Information Library 160 regarding the alternative infertility treatments and information including content selected to answer patient questions. Herein the content distribution logic is optimized to minimize the number of questions asked of a caregiver. Storage could store any of the logic discussed herein. The Information Library of information also includes content selected to answer patient questions, and wherein the content distribution logic is optimized to minimize the number of questions asked a caregiver.

In some embodiments, Training Logic 143 is configured to train the first machine learning system based on clinical success provided by the caregiver and the clinical data.

In some embodiments, Couple Logic 170 is configured to treat a pair of patients as a reproductive unit and to coordinate the selections provided to both members of the reproductive unit based on clinical data regarding both the male patient and the female patient. When a Male Factor is a predominant cause for a couple's inability to conceive, priority is given to determining the cause for this problem and possibly providing a remedy. When the Male has a significant, but not absolute, problem the couple is steered towards intrauterine insemination or In vitro fertilization. If the Male problem is absolute and incorrigible, a recommendation that the couple considers using donor sperm is made. By the same token, when a Female Factor is the predominant cause of a couple's infertility considerable time, effort, and focus is invested in identifying and, when possible, correcting any obstacles. When both partners have issues contributing to the couple's infertility equal time, attention, and effort must begiven on behalf of the Male and the Female. An example of where a man's clinical data being used to suggest treatment of woman is when a Male is found to have an uncorrectable low sperm count and this is offset by ovarian hyperstimulation of the Female, or simply proceeding to In vitro Fertilization.

In some embodiments, Microprocessor 190 is configured to execute at least the rule-based logic; or any other logic discussed herein.

A Caregiver App 120 is embodied in a caregiver computing device, wherein the caregiver application includes: an ability of the Caregiver to insert new information into Clinical Input 173, receive feedback via the Caregiver UI 175, and affect change in the Status Logic 177. A clinical input configured to receive the clinical data could be a UI or a digital input such as a network connection to a medical record system, or a sensor.

In some embodiments, the Caregiver User Interface 175 is configured for a caregiver to receive the selections from among the alternative infertility treatments through the Microprocessor 190 as they are ranked according to their associated scores.

In some embodiments, the Caregiver UI 175 is configured for a caregiver to approve the selections, to forward the selections to the patient, to approve the content from the library of information, to forward the content from the library of information to the patient, to answer questions received from the patient, to require that the caregiver provide the clinical data, and/or to enter the clinical data.

In some embodiments, Status Logic 177 is configured to track treatment status of the patient, the treatment including the selections from among the alternative infertility treatments. Feedback will include treatments received, their resulting response, and the treatment history.

Figure 2:
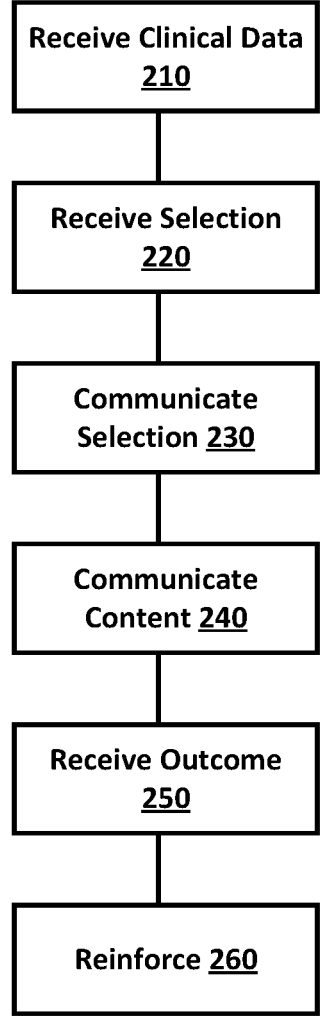
FIG. 2 is a flow chart illustrating a method of treating infertility, according to various embodiments of the invention.

FIG. 2 illustrates the method of treating infertility, according to various embodiments of the invention.

In a Receive Clinical Data Step 210, clinical data is received from various sensors 185, from the patient interface 183, and/or from a medical records system 180 via the Patient App 130A or 130B. As an example, the patient imports her sleep patterns, menstrual cycle characteristics, failed attempts at getting pregnant, and/or quantifiable data.

In Receive Selection Step 220 the data is delivered to the Expert System 110 to be processed through the Rule-Based Logic 135, the Machine Learning System 140, and/or the Knowledge Graph to select an appropriate course of action.

In a Communicate Selection Step 230 the action response is passed through the Reinforcement Logic 145, archived in Storage 155, run through the Training Logic 143 and Couple Logic 170, before passing through the Microprocessor 190 on its way to being made available to be acted upon.

In a Communicate Content Step 240 the action which has been decided upon is passed on via the Network 115 to the Caregiver App 120 and to the Patient App 130A or 130B. This is step is reinforced both through verbal communication between caregiver and patient, and via the apps. A confirmation that the correct information was received, read, and understood is made through Patient UI 183.

In a Receive Outcome Step 250 further assurance that the appropriate message and action plan was communicated is by the patient's compliance to tests ordered and/or medications prescribed.

In the Reinforce Step 260 a feedback loop to either the rule-based system and/or a machine learning system is completed.

FIG. 3 schematically illustrates a typical diagnostic and treatment methodology for the male patient in a sub-fertile couple. The diagnostic method proceeds as follows: The healthcare provider clicks the "Register for Fertility Pathways" button on the Patient UI 183 start screen. The click is transmitted to the Expert System 110 which adds de-identified demographic data for a patient of interest using a numbering system known only to the provider's office.

The Expert System 110 receives the addition of a new male patient from Patient UI 183 and stores the information in Storage 155. Rules-Based Logic 135 then sends the first diagnostic question to Caregiver UI 175 at 300, "Does the patient have a female partner?" The provider inputs the answer into Caregiver UI 175 which sends the information to Storage 155. Rules-Based Logic 135 then sends the next diagnostic question to the Caregiver UI 175, depending on the previous answer.

If the answer at 300 is no, then the information will be sent to and recorded in Storage 155 and Rules-Based Logic 135 will send a recommendation to Caregiver UI 175 for an oocyte donor and gestational carrier at 303 and recommend an IVF consultation at 307. This information is communicated to Patient UI 183 through Network 115. Those steps being done, the diagnostic review can continue onto 301.

If the answer at 300 is yes, then the information will be sent to and recorded in Storage 155 and Rules-Based Logic 135 will send the next diagnostic question to Caregiver UI 175 at 301, "Is the patient currently being prescribed calcium-channel blockers and/or androgen supplements?" The provider inputs the answer into Caregiver UI 175 which sends the information to Storage 155 and shares this information with Patient UI 183 through Network 115. Rules-Based Logic 135 then sends the next diagnostic question to the Caregiver UI 175, depending on the previous answer.

If the answer at 301 is yes, then the information will be sent to and recorded in Storage 155 and Rules-Based Logic 135 will send instructions to Caregiver UI 175 at 302, which counsels to discontinue calcium-channel blockers and androgen supplements and prescribe suitable alternative hypertensive control management. This information is shared with Patient UI 183 through Network 115. Those steps being done, the diagnostic review can continue to 304.

If the answer at 301 is no, then the information will be sent to and recorded in Storage 155 and Rules-Based Logic 135 will send the next diagnostic question to Caregiver UI 175 at 304, "Does the patient have a vasectomy?" The provider inputs the answer to Caregiver UI 175 which sends the information to Storage 155. Rules-Based Logic 135 then sends the next diagnostic question to Caregiver UI 175, depending on the previous answer.

If the answer at 304 is yes, then the information will be sent to and recorded in Storage 155 and Rules-Based Logic 135 will send the next diagnostic step to Caregiver UI 175 at 308, "Has the patient failed or is unwilling to get a reversal?" The provider inputs the answer into Caregiver UI 175 which sends the information to Storage 155. Rules-Based Logic then sends the next diagnostic question to Caregiver UI 175 depending on the previous answer.

If the answer at 304 is no, then the information will be sent to and recorded in Storage 155 and Rules-Based Logic 135 will send the next diagnostic question to Caregiver UI 175 at 353, "Does the patient have congenital absence of the vas deferens?" The provider inputs the answer into Caregiver UI 175 which sends the information to Storage 155. Rules-Based Logic then sends the next diagnostic question depending on the previous answer.

If the answer at 308 is yes, then the information will be sent to and recorded in Storage 155 and Rules-Based Logic 135 will send the next diagnostic step to Caregiver UI 175 at 317, "Is the Patient Willing to Undergo TESA?" The provider inputs the answer into Caregiver UI 175 which sends the information to Storage 155. Rules-Based Logic then sends the next diagnostic question to Caregiver UI 175 depending on the previous answer.

If the answer at 308 is no, then the information will be sent to and recorded in Storage 155 and Rules-Based Logic 135 will send the next diagnostic step to Caregiver UI 175 at 309, "A vasectomy reversal is recommended for the patient." The provider communicates this recommendation to the patient and schedules a follow up.

If the answer at 353 is yes, then the information will be sent to and recorded in Storage 155 and Rules-Based Logic 135 will send the next diagnostic step to Caregiver UI 175 at 317, "Is the patient willing to undergo TESA?" The provider inputs the answer into Caregiver UI 175 which sends the information to Storage 155. Rules-Based Logic then sends the next diagnostic question to Caregiver UI 175 depending on the previous answer.

If the answer at 353 is no, then the provider will input the information into Caregiver UI 175 which sends the information to Storage 155 for recording. Rules-Based Logic 135 then processes said information and sends the next diagnostic question to Caregiver UI 175 at 305, "Has the patient been involved in a recent pregnancy within the last year?" The provider then inputs the response into Caregiver UI 175 which sends the information to Storage 155 for recording.

Rules-Based Logic 135 then sends the next diagnostic question to Caregiver UI 175 depending on the previous answer.

If the patient agrees to and undergoes the vasectomy reversal recommended at 309, then on follow up after the procedure the diagnostic process will continue. After inputting the information into Caregiver UI 175, said information will be sent to and recorded in Storage 155 and Rules-Based Logic 135 will send the next diagnostic step to Caregiver UI 175 at 310, "Obtain a semen analysis within at least 2 days, but no more than 5 days of abstinence from ejaculation." The provider communicates this recommendation to the patient and schedules a follow up at 318.

If the answer at 317 is yes, the provider will input the information into Caregiver UI 175 which sends the information to Storage 155 for recording. Rules-Based Logic 135 then processes said information and sends the next diagnostic question to Caregiver UI 175 at 322, "TESA is recommended for the patient." The provider communicates this recommendation to the patient and Rules-Based Logic 135 processes the next step.

If the answer at 317 is no, the provider will input the information into Caregiver UI 175 which sends the information to Storage 155 for recording. Rules-Based Logic 135 then processes said information and sends the next diagnostic step to Caregiver UI 175 at 316, "Donor sperm is recommended for the patient." The provider communicates this recommendation to the patient and the diagnostic protocol is complete for the male partner.

If the answer at 305 is yes, then the provider will input the information into Caregiver UI 175 which sends the information to Storage 155 for recording. Rules-Based Logic 135 then processes said information and sends the next diagnostic question to Caregiver UI 175 at 306, "The patient's semen can be used for impregnation. There's no need to check him further at this time." At this point, the provider can return to the female diagnostic protocol.

If the answer at 305 is no, then the provider will input the information into Caregiver UI 175 which sends the information to Storage 155 for recording. Rules-Based Logic 135 then processes said information and sends the next diagnostic step to Caregiver UI 175 at 310, "Obtain a semen analysis within at least two days, but no more than 5 days of abstinence from ejaculation." The provider then orders the lab to be taken. When the lab results are obtained, the provider will input them into Caregiver UI 175 which sends the information to Storage 155 for recording. Rules-Based Logic 135 then sends the next diagnostic question to Caregiver UI 175 depending on the lab results.

If the patient agrees to and undergoes the semen analysis recommended at 310, then on follow up after the procedure the diagnostic process will continue with inputting the results at 318, "Is the semen volume greater or equal to 1.0 mL?" The provider inputs this information into Caregiver UI 175 which sends the information to Storage 155. Rules-Based Logic 135 then sends the next diagnostic question to Caregiver UI 175 depending on the previous answer.

If the answer at 318 is yes, then the provider will input the information into Caregiver UI 175 which will then send said information to be recorded in Storage 155. Rules-Based Logic 135 will then process said information and send the next diagnostic question to Caregiver UI 175 at 324, "Is the Morphology >14%?" The provider inputs the answer into Caregiver UI 175 which sends the information to Storage 155. Rules-Based Logic 135 then sends the next diagnostic question to Caregiver UI 175, depending on the previous answer.

If the answer at 318 is no, the provider will input the information into Caregiver UI 175 which will send said information to be recorded in Storage 155. Rules-Based Logic 135 will then process said information and send the next diagnostic question to Caregiver UI 175 at 319, "Is the Morphology greater than or equal to 14.0%?" The provider inputs the answer into Caregiver UI 175 which sends the information to Storage 155. Rules-Based Logic 135 then sends the next diagnostic question to Caregiver UI 175, depending on the previous answer.

If the patient agrees to TESA at 322, then the provider communicates the next step provided by Rules-Based Logic 175 to the patient at 332, "IVF is recommended for the patient." At this point the diagnostic protocol is complete.

At 316, a recommendation is made to use donor sperm at both Caregiver UI 174 and Patient UI 183 with content disseminated throughout System 110 via Content Distribution Logic 163. Diagnosis is complete.

At 306, a recommendation is made at both Caregiver UI 174 and Patient UI 183 to return to the female partner's focus of care as the seminal parameters have been found to be satisfactory. This conclusion is disseminated throughout System 110 via Content Distribution Logic 163. Diagnosis is complete.

If the answer at 324 is yes, the provider will input the information into Caregiver UI 175 which will then send said information to be recorded in Storage 155. Rules-Based Logic 135 will then process said information and send the next diagnostic question to Caregiver UI 175 at 324, "Is the Motility greater than or equal to 50%?" The provider inputs the answer into Caregiver UI 175 which sends said information to Storage 155. Rules-Based Logic 135 then sends the next diagnostic question to Caregiver UI 175, depending on the previous answer.

If the answer at 324 is no, the provider will input the information into Caregiver UI 175 which will then send said information to be recorded in Storage 155. Rules-Based Logic 135 will then process said information and send the next diagnostic question to Caregiver UI 175 at 323, "Is the Motility Grade greater than 30% (+3/+4)?" The provider inputs the answer into Caregiver UI 175 which sends said information to Storage 155. Rules-Based Logic 135 then sends the next diagnostic question to Caregiver UI 175, depending on the previous answer.

If the answer at 319 is yes, the provider will input the information into Caregiver UI 175 which will then send said information to be recorded in Storage 155. Rules-Based Logic 135 will then process said information and send the next diagnostic step to Caregiver UI 175 at 336, "Is the sperm count greater than or equal to 20 million/mL?" The provider inputs the answer into Caregiver UI 175 which sends said information to Storage 155. Rules-Based Logic 135 then sends the next diagnostic question to Caregiver UI 175, depending on the previous answer.

If the answer at 319 is no, the provider will input the information into Caregiver UI 175 which will then send said information to be recorded in Storage 155. Rules-Based Logic 135 will then process said information and send the next diagnostic step to Caregiver UI 175 at 325, "Is greater than 30% Grade Motility (+3/+4)?" The provider inputs the lab result into Caregiver UI 175 which sends said information to Storage 155. Rules-Based Logic 135 then sends the next diagnostic step to Caregiver UI 175, depending on the previous answer.

At 332 a recommendation is made to proceed with IVF and diagnosis is complete.

If the answer at 334 is yes, the provider will input the information into Caregiver UI 175 which will then send said information to be recorded in Storage 155. Rules-Based Logic 135 will then process said information and send the next diagnostic step to Caregiver UI 175 at 347, "Is the sperm count greater than or equal to 20 million/mL?" The provider inputs the lab result into Caregiver UI 175 which sends said information to Storage 155. Rules-Based Logic 135 then sends the next diagnostic step to Caregiver UI 175, depending on the previous answer.

If the answer at 334 is no, the provider will input the information into Caregiver UI 175 which will then send said information to be recorded in Storage 155. Rules-Based Logic 135 will then process said information and send the next diagnostic step to Caregiver UI 175 at 333, "Is the sperm count greater than or equal to 20 million/mL?" The provider inputs the lab result into Caregiver UI 175 which sends said information to Storage 155. Rules-Based Logic 135 then sends the next diagnostic step to Caregiver UI 175, depending on the previous answer.

If the answer at 323 is yes, the provider will input the information into Caregiver UI 175 which will then send said information to be recorded in Storage 155. Rules-Based Logic 135 will then process said information and send the next diagnostic step to Caregiver UI 175 at 335, "Is the Motility greater than or equal to 50%?" The provider inputs the lab result into Caregiver UI 175 which sends said information to Storage 155. Rules-Based Logic 135 then sends the next diagnostic step to Caregiver UI 175, depending on the previous answer.

If the answer at 323 is no, the provider will input the information into Caregiver UI 175 which will then send said information to be recorded in Storage 155. Rules-Based Logic 135 will then process said information and send the next diagnostic question to Caregiver UI 175 at 331, "Does the patient have a previous history of vasectomy?" The provider inputs the answer into Caregiver UI 175 which sends said information to Storage 155. Rules-Based Logic 135 then sends the next diagnostic step to Caregiver UI 175, depending on the previous answer.

If the answer at 336 is yes, the provider will input the information into Caregiver UI 175 which will then send said information to be recorded in Storage 155. Rules-Based Logic 135 will then process said information and send the next diagnostic step to Caregiver UI 175 at 348, "Is sperm count greater than or equal to 20 million/mL?" The provider inputs the answer into Caregiver UI 175 which sends said information to Storage 155. Rules-Based Logic 135 then sends the next diagnostic step to Caregiver UI 175, depending on the previous answer.

If the answer at 336 is no, the provider will input the information into Caregiver UI 175 which will then send said information to be recorded in Storage 155. Rules-Based Logic 135 will then process said information and send the next diagnostic question to Caregiver UI 175 at 345, "Does the patient have a varicocele?" The provider inputs the answer into Caregiver UI 175 which sends said information to Storage 155. Rules-Based Logic 135 then sends the next diagnostic step to Caregiver UI 175, depending on the previous answer.

If the answer at 325 is yes, the provider will input the information into Caregiver UI 175 which will then send said information to be recorded in Storage 155. Rules-Based Logic 135 will then process said information and send the next diagnostic step to Caregiver UI 175 at 335, "Is the Motility greater than or equal to 50%?" The provider inputs the answer into Caregiver UI 175 which sends said information to Storage 155. Rules-Based Logic 135 then sends the next diagnostic step to Caregiver UI 175, depending on the previous lab result.

If the answer at 325 is no, the provider will input the information into Caregiver UI 175 which will then send said information to be recorded in Storage 155. Rules-Based Logic 135 will then process said information and send the next diagnostic question to Caregiver UI 175 at 331, "Does the patient have a previous history of varicocelectomy?" The provider inputs the answer into Caregiver UI 175 which sends said information to Storage 155. Rules-Based Logic 135 then sends the next diagnostic step to Caregiver UI 175, depending on the previous answer.

If the answer at 347 is yes, the provider will input the information into Caregiver UI 175 which will then send said information to be recorded in Storage 155. Rules-Based Logic 135 will then process said information and send the next diagnostic step to Caregiver UI 175 at 350, "Is greater than 30% Grade Motility (+3/+4)?" The provider inputs the answer into Caregiver UI 175 which sends said information to Storage 155. Rules-Based Logic 135 then sends the next diagnostic step to Caregiver UI 175, depending on the previous lab result.

If the answer at is no, the provider will input the information into Caregiver UI 175 which will then send said information to be recorded in Storage 155. Rules-Based Logic 135 will then process said information and send the next diagnostic step to Caregiver UI 175 at 346, "Is total sperm count greater than 40 million?" The provider inputs the answer into Caregiver UI 175 which sends said information to Storage 155. Rules-Based Logic 135 then sends the next diagnostic step to Caregiver UI 175, depending on the previous lab result.

If the answer at 333 is yes, the provider will input the information into Caregiver UI 175 which will then send said information to be recorded in Storage 155. Rules-Based Logic 135 will then process said information and send the next diagnostic step to Caregiver UI 175 at 352, "Intrauterine Insemination (up to 6x)." The provider communicates this recommendation to the patient and the Rules-Based Logic 135 processes the next step.

If the answer at 333 is no, the provider will input the information into Caregiver UI 175 which will then send said information to be recorded in Storage 155. Rules-Based Logic 135 will then process said information and send the next diagnostic question to Caregiver UI 175 at 345, "Does the patient have a varicocele?" The provider inputs the answer into Caregiver UI 175 which sends said information to Storage 155. Rules-Based Logic 135 then sends the next diagnostic step to Caregiver UI 175, depending on the previous answer.

If the answer at 335 is yes, the provider will input the information into Caregiver UI 175 which will then send said information to be recorded in Storage 155. Rules-Based Logic 135 will then process said information and send the next diagnostic step to Caregiver UI 175 at 348, "Is the sperm count greater than or equal to 20 million/mL?" The provider inputs the answer into Caregiver UI 175 which sends said information to Storage 155. Rules-Based Logic 135 then sends the next diagnostic step to Caregiver UI 175, depending on the previous lab result.

If the answer at 335 is no, the provider will input the information into Caregiver UI 175 which will then send said information to be recorded in Storage 155. Rules-Based Logic 135 will then process said information and send the next diagnostic step to Caregiver UI 175 at 336, "Is the sperm count greater than or equal to 20 million/mL?" The provider inputs the answer into Caregiver UI 175 which sends said information to Storage 155. Rules-Based Logic 135 then sends the next diagnostic step to Caregiver UI 175, depending on the previous lab result.

If the answer at 331 is yes, the provider will input the information into Caregiver UI 175 which will then send said information to be recorded in Storage 155. Rules-Based Logic 135 will then process said information and send the next diagnostic step to Caregiver UI 175 at 330, "Is the patient taking Tamoxifen, Clomid, or Aromatase Inhibitors?" The provider inputs the answer into Caregiver UI 175 which sends said information to Storage 155. Rules-Based Logic 135 then sends the next diagnostic step to Caregiver UI 175, depending on the previous answer.

If the answer at 331 is no, the provider will input the information into Caregiver UI 175 which will then send said information to be recorded in Storage 155. Rules-Based Logic 135 will then process said information and send the next diagnostic question to Caregiver UI 175 at 345, "Does the patient have a varicocele?" The provider inputs the answer into Caregiver UI 175 which sends said information to Storage 155. Rules-Based Logic 135 then sends the next diagnostic step to Caregiver UI 175, depending on the previous answer.

If the answer at 348 is yes, the provider will input the information into Caregiver UI 175 which will then send said information to be recorded in Storage 155. Rules-Based Logic 135 will then process said information and send the next diagnostic step to Caregiver UI 175 at 352, "Intrauterine insemination (up to 6×)." The provider communicates the recommendation to the patient and Rules-Based Logic 135 processes the next diagnostic step.

If the answer at 348 is no, the provider will input the information into Caregiver UI 175 which will then send said information to be recorded in Storage 155. Rules-Based Logic 135 will then process said information and send the next diagnostic question to Caregiver UI 175 at 331, "Does the patient have a previous history of varicocelectomy?" The provider inputs the answer into Caregiver UI 175 which sends said information to Storage 155. Rules-Based Logic 135 then sends the next diagnostic step to Caregiver UI 175, depending on the previous answer.

If the answer at 345 is yes, the provider will input the information into Caregiver UI 175 which will then send said information to be recorded in Storage 155. Rules-Based Logic 135 will then process said information and send the next diagnostic step to Caregiver UI 175 at 349, "Ligation, recheck semen analysis in 3 months." The provider communicates the recommendation to the patient. Rules-Based Logic 135 then processes the next diagnostic step at 310 following the recommended procedure and sends it to Caregiver UI 175.

If the answer at 345 is no, the provider will input the information into Caregiver UI 175 which will then send said information to be recorded in Storage 155. Rules-Based Logic 135 will then process said information and send the next diagnostic step to Caregiver UI 175 at 330, "Is the patient taking Tamoxifen, Clomid, or Aromatase Inhibitors?" The provider inputs the answer into Caregiver UI 175 which sends said information to Storage 155. Rules-Based Logic 135 then sends the next diagnostic step to Caregiver UI 175, depending on the previous answer.

If the answer at 350 is yes, the provider will input the information into Caregiver UI 175 which will send said information to be recorded in Storage 155. Rules-Based Logic 135 will then process said information and send the next diagnostic step to Caregiver UI 175 at 351, "Male patient appears to be suitable for pregnancy. Check female partner." At this point the diagnostic protocol for the male patient is completed.

If the answer at 350 is no, the provider will input the information into Caregiver UI 175 which will send said information to be recorded in Storage 155. Rules-Based Logic 135 will then process said information and send the next diagnostic step to Caregiver UI 175 at 352, "Intrauterine insemination (up to 6×)." The provider will communicate this recommendation to the patient. Rules-Based Logic 135 will process the next step at 306 to be sent to the Caregiver UI 175.

If the answer at 346 is yes, the provider will input the information into Caregiver UI 175 which will send said information to be recorded in Storage 155. Rules-Based Logic 135 will then process said information and send the next diagnostic step to Caregiver UI at 352, "Intrauterine insemination (up to 6×)." The provider will communicate this recommendation to the patient. Rules-Based Logic 135 will process the next step at 306 to be sent to the Caregiver UI 175.

If the answer at 346 is no, the provider will input the information into Caregiver UI 175 which will send said information to be recorded in Storage 155. Rules-Based Logic 135 will then process said information and send the next diagnostic question to Caregiver UI at 345, "Does the patient have a varicocele?" The provider will input the answer into Caregiver UI 175 which will send said information to Storage 155. Rules-Based Logic 135 processes said information and sends the next diagnostic step to Caregiver UI 175, depending on the previous answer.

Transmit recommendation at 352 to Patient UI 183, Caregiver UI 175, and Content Distribution Logic 163. Then proceed to 306.

If the answer at 330 is yes, the provider will input the information into Caregiver UI 175 which will send said information to be recorded in Storage 155. Rules-Based Logic 135 will then process said information and send the next diagnostic step to Caregiver UI 175 at 332, "IVF is recommended for the patient." The provider will communicate this recommendation to the patient and the protocol is completed.

If the answer at 330 is no, the provider will input the information into Caregiver UI 175 which will send said information to be recorded in Storage 155. Rules-Based Logic 135 will then process said information and send the next diagnostic step to Caregiver UI 175 at 329, "Obtain FSH and Testosterone Levels." The provider will order the labs for the patient. Rules-Based Logic 135 will process the next step at 315 to be sent to the Caregiver UI 175.

After the recommended procedure at 349, the Rules-Based Logic 135 will process the next diagnostic step and send it to Caregiver UI 175 at 310, "Obtain a semen analysis within at least 2 days, but no more than 5 days, of abstinence from ejaculation." The provider will communicate this to the patient and order the follow up lab work. The Rules-Based Logic 135 will then process the next diagnostic step at 318.

If the answer at 315 is yes, the provider will input the information into Caregiver UI 175 which will then send said information to be recorded in Storage 155. Rules-Based Logic 135 will then process said information and send the next diagnostic step to Caregiver UI 175 at 316, "Donor sperm is recommended for the patient." The provider will communicate this recommendation to the patient and the male diagnostic protocol is complete.

If the answer at 315 is no, the provider will input the information into Caregiver UI 175 which will then send said information to be recorded in Storage 155. Rules-Based Logic 135 will then process said information and send the next diagnostic step to Caregiver UI 175 at 314, "Is the Testosterone less than or equal to 350 ng/dL?" The provider inputs the answer into Caregiver UI 175 which sends said information to Storage 155. Rules-Based Logic 135 then processes and sends the next diagnostic step to Caregiver UI 175, depending on the lab results.

If the answer at 314 is yes, the provider will input the information into Caregiver UI 175 which will then send said information to be recorded in Storage 155. Rules-Based Logic 135 will then process said information and send the next diagnostic step to Caregiver UI 175 at 313, "Is FSH greater than or equal to 10 IU/L?" The provider inputs the answer into Caregiver UI 175 which sends said information to Storage 155. Rules-Based Logic 135 then sends the next diagnostic step to Caregiver UI 175, depending on the previous answer.

If the answer at 314 is no, the provider will input the information into Caregiver UI 175 which will then send said information to be recorded in Storage 155. Rules-Based Logic 135 will then process said information and send the next diagnostic step to Caregiver UI 175 at 321, "Is Testosterone greater than or equal to 850 ng/dL?" The provider inputs the answer into Caregiver UI 175 which sends said information to Storage 155. Rules-Based Logic 135 then sends the next diagnostic step to Caregiver UI 175, depending on the previous answer.

If the answer at 313 is yes, the provider will input the information into Caregiver UI 175 which will then send said information to be recorded in Storage 155. Rules-Based Logic 135 will then process said information and send the next diagnostic step to Caregiver UI 175 at 311, "Has the patient already had a trial with Tamoxifen+Depo-Testosterone?" The provider inputs the answer into Caregiver UI 175 which sends said information to Storage 155. Rules-Based Logic 135 then sends the next diagnostic step to Caregiver UI 175, depending on the previous answer.

If the answer at 313 is no, the provider will input the information into Caregiver UI 175 which will then send said information to be recorded in Storage 155. Rules-Based Logic 135 will then process said information and send the next diagnostic step to Caregiver UI 175 at 320, "Prescribe Tamoxifen 20 mg/day×6 months but recheck FSH and testosterone in one month." The provider communicates this recommendation to the patient and schedules a follow up in one month. Rules-Based Logic 135 processes and sends the next diagnostic step at 337 to Caregiver UI 175.

FIG. 4 schematically illustrates a typical diagnostic and treatment methodology for the female patient in a sub-fertile couple. The diagnostic method proceeds as follows: The healthcare provider clicks the "Register for Fertility Pathways" button on the Patient UI 183 start screen. The click is transmitted to the Expert System 110 which adds deidentified demographic data for a patient of interest using a numbering system known only to the provider's office.

The Expert System 110 receives the addition of the new female patient from Patient UI 183 and stores the information in Storage 155. Rules-Based Logic 135 then sends the first diagnostic step to Caregiver UI 175 at 4000, "Is the patient over 43 years of age?" The provider inputs the answer into Caregiver UI 175 which sends the information to Storage 155. Rules-Based Logic 135 then sends the next step in the sequence, depending upon the previous response.

If the answer at 4000 is yes, the information will be sent to and recorded in Storage 155 and Rules-Based Logic 135 will send a notification to Caregiver UI 175 and Patient UI

183 at 4001, "Our maximum age for a female patient is 42". The encounter is concluded, thus ending the patient's access to the algorithm.

If the answer at 4000 is no, then the information will be sent to and recorded in Storage 155 and Rules-Based Logic 135 sends the second diagnostic step to Caregiver UI 175 at 4002, "Is the patient over years of age?" The provider inputs the answer into Caregiver UI 175 which sends the information to Storage 155. Rules-Based Logic 135 then sends information and explanations to Patient UI 183 and the next directive or diagnostic step to Caregiver UI 175, depending upon the previous response.

If the answer at 4002 is yes, then the information will be sent to and recorded in Storage 155 and Rules-Based Logic 135 will send relevant information and explanations to Patient IU 183 and the next step to Caregiver UI 175 at 4003, "The patient is over 38. There is an increased risk for fetal chromosomal abnormalities." The provider will instruct the patient as to the directive and enter a confirmation in Caregiver UI 175 which sends the information to Storage 155. Rules-Based Logic 135 sends the diagnostic step to Caregiver UI 175 at 4004, "Was the patient's weight entered within the last 7 days?" The provider inputs the answer into Caregiver UI 175 which sends the information to Storage 155. Rules-Based Logic 135 then sends information and explanations to Patient UI 183 and the next directive or diagnostic step to Caregiver UI 175, depending upon the previous response.

If the answer at 4002 is no, then the information will be sent to and recorded in Storage 155 and Rules-Based Logic 135 will send relevant information and explanations to Patient UI 183 and the next diagnostic step to Caregiver UI 175 at 4004, "Was the patient's weight entered within the last seven days?" The provider inputs the answer into Caregiver UI 175 which sends the information to Storage 155. Rules-Based Logic 135 then sends information and explanations to Patient UI 183 and the next directive or diagnostic step to Caregiver UI 175, depending upon the previous response.

If the answer at 4004 is no, then the information will be sent to and recorded in Storage 155 and Rules-Based Logic 135 will send a directive to Caregiver UI 175 at 4005, "Update patient weight." The provider will instruct the patient as to the directive, enter the requisite data, and enter a confirmation to Caregiver UI 175 which sends the information to Storage 155. Rules-Based Logic 135 will send relevant information and explanations to Patient UI 183 and the next diagnostic step to Caregiver UI 175 at 4006, "Is BMI≥17 and ≤37?" The provider inputs the answer into Caregiver 175 which sends the information to Storage 155. Rules-Based Logic 135 then sends the next directive or diagnostic step to Caregiver UI 175 depending on the previous answer.

If the answer at 4004 is yes, then the information will be sent to and recorded in Storage 155 and Rules-Based Logic 135 will send the next diagnostic step to Caregiver UI 175 at 4006, "Is BMI≥17 and ≤37?" The provider inputs the answer into Caregiver 175 which sends the information to Storage 155. Rules-Based Logic 135 then sends the next diagnostic step to Caregiver UI 175 depending on the previous answer.

If the answer at 4006 is yes, then the information will be sent to and recorded in Storage 155 and Rules-Based Logic 135 will send the next diagnostic question to Caregiver UI 175 at 4008, "Has the patient had a previous pregnancy?" The provider inputs the answer into Caregiver UI 175 which sends the information to Storage 155. Rules-Based Logic 135 then sends the next diagnostic step to Caregiver UI 175 depending on the previous answer.

If the answer at 4006 is no, then the information will be sent to and recorded in Storage 155 and Rules-Based Logic 135 will send relevant information and explanations to Patient UI 183 and the next directive to Caregiver UI 175 at 4007 stating, "Patient's BMI must be between 17 and 37 before proceeding." The provider will instruct the patient as to the directive and enter a confirmation to Caregiver UI 175 which sends the information to Storage 155. The algorithm comes to a hard stop until BMI re-entry complies with requirement of being between 17 and 37. This gets passed through the Expert System 110 in all 5 stages (135, 140, 150, 145, and 163). Resumption of protocol will again begin at 4000.

If the answer at 4008 is yes, then the information will be sent to and recorded in Storage 155 and Rules-Based Logic 135 will send relevant information with explanations to Patient UI 183 along with the next diagnostic step to Caregiver UI 175 at 4009, "Is the patient currently breast-feeding?" The provider inputs the answer into Caregiver UI 175 which sends the information to Storage 155. Rules-Based Logic 135 then sends the next directive or diagnostic step to Caregiver UI 175 depending on the previous answer.

If the answer at 4008 is no, then the information will be sent to and recorded in Storage 155 and Rules-Based Logic 135 will send relevant information and explanations to Patient UI 183 along with the next diagnostic step to Caregiver UI 175 at 4016, "Does the patient have a male partner?" The provider inputs the answer into Caregiver UI 175 which sends the information to Storage 155. Rules-Based Logic then sends the next directive or diagnostic step to Caregiver UI 175 depending on the previous answer.

If the answer at 4009 is yes, the information will be sent to and recorded in Storage 155 and Rules-Based Logic 135 will send relevant information and explanations to Patient UI 183 and the directive to Caregiver UI 175 and Patient UI 183 at 4010, "The patient must stop breastfeeding and return in 3 months." The provider will instruct the patient as to the directive and enter a confirmation to Caregiver UI 175. The algorithm comes to a hard stop until breastfeeding has stopped for 3 months. This gets passed through the Expert System 110 in all 5 stages (135, 140, 150, 145, and 163). Resumption of protocol will re-enter at 4011.

If the answer at 4009 is no, then the information will be sent to and recorded in Storage 155 and Rules-Based Logic 135 will send relevant information with explanations to Patient UI 183 along with the next diagnostic step to Caregiver UI 175 at 4011 stating, "Was the end of the last pregnancy less than one year ago?" The provider inputs the answer into Caregiver UI 175 which sends the information to Storage 155. Rules-Based Logic 135 then sends the next diagnostic step to Caregiver UI 175 depending on the previous answer.

If the answer at 4011 is yes, then information will be sent to and recorded in Storage 155 and Rules-Based Logic 135 will send relevant information with explanations to Patient UI 183 along with the next diagnostic step to Caregiver UI 175 at 4012, "Was the pregnancy carried to viability?" The provider inputs the answer into Caregiver UI 175 which sends the information to Storage 155. Rules-Based Logic 135 then sends the next diagnostic step to Caregiver UI 175 depending on the previous answer.

If the answer at 4011 is no, then the information will be sent to and recorded in Storage 155 and Rules-Based Logic 135 will send relevant information and explanations to Patient UI 183 along with the next diagnostic step to Caregiver UI 175 at 4016, "Does the patient have a male partner?" The provider inputs the answer into Caregiver UI 175 which sends the information to Storage 155. Rules-Based Logic 135 then sends the next diagnostic step to Caregiver UI 175 depending on the previous answer.

If the answer at 4012 is yes, then the information will be sent to and recorded in Storage 155 and Rules-Based Logic 135 will send relevant information with explanations to Patient UI 183 along with the next diagnostic step to Caregiver UI 175 at 4013, "Is the patient's age ≥35?" The provider inputs the answer into Caregiver UI 175 which sends the information to Storage 155. Rules-Based Logic 135 then sends the next directive to Caregiver UI 175 depending on the previous answer.

If the answer at 4012 is no, then the information will be sent to and recorded in Storage 155 and Rules-Based Logic 135 will send relevant information with explanations to Patient UI 183 along with the next diagnostic step to Caregiver UI 175 at 4098, "Has the patient been tested for the presence of anticardiolipin antibodies, lupus anticoagulant, anti-beta2-glycoprotein 1 antibodies, and Factor V Leiden mutation?" The provider inputs the answer into Caregiver UI 175 which sends the information to Storage 155. Rules-Based Logic 135 then sends the next directive or diagnostic step to Caregiver UI 175 depending on the previous answer.

If the answer at 4013 is yes, the information will be sent to and recorded in Storage 155 and Rules-Based Logic 135 will send relevant information and explanations to Patient UI 183 along with the hard-stop directive to Caregiver UI 175 at 4014, "The algorithm should be restarted 6 months postpartum." The provider will instruct the patient as to the directive and enter a confirmation to Caregiver UI 175. Re-entry will be at 4000.

If the answer at 4013 is no, the information will be sent to and recorded in Storage 155 and Rules-Based Logic 135 will send relevant information and explanations to Patient UI 183 along with the hard-stop directive to Caregiver UI 175 at 4015, "The algorithm should be restarted 12 months postpartum." The provider will instruct the patient as to the directive and enter a confirmation to Caregiver UI 175. Re-entry will be at 4000.

If the answer at 4016 is yes, then the information will be sent to and recorded in Storage 155 and Rules-Based Logic 135 will send relevant information with explanations to Patient UI 183 along with the next diagnostic step to Caregiver UI 175 at 4018, "Is the couple using a lubricant during intercourse that could be spermicidal?" The provider inputs the answer into Caregiver UI 175 which sends the information to Storage 155. Rules-Based Logic 135 then sends the next directive or diagnostic step to Caregiver UI 175 depending on the previous answer.

If the answer at 4016 is no, then the information will be sent to and recorded in Storage 155 and Rules-Based Logic 135 will send relevant information and explanations to Patient UI 183 along the directive to Caregiver UI 175 at 4017, "Donor sperm will be used for this pregnancy." The provider will instruct the patient as to the directive and enter a confirmation to Caregiver UI 175 which sends the information to Storage 155. Rules-Based Logic 135 will send relevant information with explanations to Patient UI 183 along with the next diagnostic step to Caregiver UI 175 at 4022, "Does the patient have spontaneous monthly cycles?" The provider inputs the answer into Caregiver UI 175 which sends the information to Storage 155. Rules-Based Logic 135 then sends the next directive or diagnostic step to Caregiver UI 175 depending on the previous answer.

If the answer at 4018 is yes, then the information will be sent to and recorded in Storage 155 and Rules-Based Logic 135 will send relevant information with explanations to Patient UI 183 along with the instruction to Caregiver UI 175 and Patient UI 183 at 4019, "Discontinue use of spermicidal lubricants." The provider will instruct the patient as to the directive and enter a confirmation to Caregiver UI 175 which sends the information to Storage 155. Rules-Based Logic 135 will send relevant information with explanations to Patient UI 183 along with the next diagnostic step to Caregiver UI 175 at 4020, "Has the male protocol been executed on the male partner?" The provider inputs the answer into Caregiver UI 175 which sends the information to Storage 155. Rules-Based Logic 135 then sends the next diagnostic step to Caregiver UI 175 depending on the previous answer.

If the answer at 4018 is no, then the information will be sent to and recorded in Storage 155 and Rules-Based Logic 135 will send relevant information with explanations to Patient UI 183 along with the next diagnostic step to Caregiver UI 175 at 4020, "Has the male protocol been executed on the male partner?" The provider inputs the answer into Caregiver UI 175 which sends the information to Storage 155. Rules-Based Logic 135 then sends the next directive or diagnostic step to Caregiver UI 175 depending on the previous answer.

If the answer at 4020 is yes, then the information will be sent to and recorded in Storage 155 and Rules-Based Logic 135 will send relevant information with explanations to Patient UI 183 along with the next diagnostic step to Caregiver UI 175 at 4022, "Does the patient have spontaneous monthly cycles?" The provider inputs the answer into Caregiver UI 175 which sends the information to Storage 155. Rules-Based Logic 135 then sends the next directive or diagnostic step to Caregiver UI 175 depending on the previous answer.

If the answer at 4020 is no, then the information will be sent to and recorded in Storage 155 and Rules-Based Logic 135 will send relevant information with explanations to Patient UI 183 along with the next directive to Caregiver UI 175 and Patient UI 183 at 4021, "Execute the male protocol before proceeding." This is a soft stop/pause which will allow the Couple Logic 170 to proceed to the diagnostic step at 4022, "Does the patient have spontaneous monthly cycles?" as the male protocol is also underway. The provider inputs the answer into Caregiver UI 175 which sends the information to Storage 155. Rules-Based Logic 135 then sends the next directive or diagnostic step to Caregiver UI 175 depending on the previous answer.

If the answer at 4022 is yes, then the information will be sent to and recorded in Storage 155 and Rules-Based Logic 135 will send relevant information with explanations to Patient UI 183 along with the next diagnostic step to Caregiver UI 175 at 4023, "is the patient taking Provera?" The provider inputs the answer into Caregiver UI 175 which sends the information to Storage 155. Rules-Based Logic 135 then sends the next directive to Caregiver UI 175 depending on the previous answer.

If the answer at 4022 is no, then the information will be sent to and recorded in Storage 155 and Rules-Based Logic 135 will send relevant information with explanations to Patient UI 183 along with the directive to Caregiver UI 175 and Patient UI 183 at 4025, "Prescribe Provera 10 mg/day× 12 days." The provider will instruct the patient as to the directive, prescribe the medication, and enter confirmation in Caregiver UI 175 which sends the information to Storage 155. Rules-Based Logic 135 will process the next diagnostic step at 4026, "Does the patient experience withdrawal bleed within three days of stopping Provera?" The provider inputs the answer into Caregiver UI 175 which sends the information to Storage 155. Rules-Based Logic 135 then sends the next directive to Caregiver UI 175 depending on the previous answer.

If the answer at 4023 is yes, then the information will be sent to and recorded in Storage 155 and Rules-Based Logic 135 will send relevant information with explanations to Patient UI 183 along the directive to Caregiver UI 175 and Patient UI 183 at 4024, "The patient should stop taking Provera." The provider will instruct the patient as to the directive and enter a confirmation to Caregiver UI 175. Rules-Based Logic will send the next directive to Caregiver UI 175 and Patient UI 183 at 4027, "Blood tests required on Day 2 (or 3) of cycle: estradiol and FSH" The provider will instruct the patient as to the directive, order the blood tests, and enter the results in Caregiver UI 175 which sends the information to Storage 155. Rules-Based Logic 135 will send relevant information with explanation to Patient UI 183 along with the next diagnostic step to Caregiver UI 175 at 4030, "Is FSH<4 mIU/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4023 is no, then the information will be sent to and recorded in Storage 155 and Rules-Based Logic 135 will send relevant information with explanations to Patient UI 183 along with the directive to Caregiver UI 175 and Patient UI 183 at 4027, "Blood tests required on Day2 (or 3) of cycle: estradiol and FSH." The provider will instruct the patient as to the directive, order the blood tests, and enter the results in Caregiver UI 175 which sends the information to Storage 155. Rules-Based Logic 135 will send relevant information with explanation to Patient UI 183 along with the next diagnostic step to Caregiver UI 175 step at 4030, "Is FSH<4 mIU/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4026 is yes, then the information will be sent to and recorded in Storage 155 and Rules-Based Logic 135 will send relevant information with explanations to Patient UI 183 along with the directive to Caregiver UI 175 and Patient UI 183 at 4027, "Blood tests required on Day 2 (or 3) of cycle: estradiol and FSH." The provider will instruct the patient as to the directive, order the blood tests, and enter the results in Caregiver UI 175 which sends the information to Storage 155. Rules-Based Logic 135 will send relevant information with explanation to Patient UI 183 along with the next diagnostic step to Caregiver UI 175 at 4030, "Is hCG≥5 mIU/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4026 is no, then the information will be sent to and recorded in Storage 155 and Rules-Based Logic 135 will send relevant information with explanations to Patient UI 183 along with the instruction to Caregiver UI 175 and Patient UI 183 at 4028, "Labs needed: Estradiol, FSH, hCG (or uCG)" The provider will instruct the patient as to the directive, order the blood tests, and enter the results in Caregiver UI 175 which sends the information to Storage 155. Rules-Based Logic 135 will send relevant information with explanation to Patient UI 183 along with the next diagnostic step to Caregiver UI 175 at 4029, "Is hCG≥5 mIU/mL or urine pregnancy test positive?" The provider inputs the answer into Caregiver UI 175 which sends the information to Storage 155. Rules-Based Logic 135 then sends the next directive or diagnostic step to Caregiver UI 175 depending on the previous answer.

If the answer at 4029 is yes, then the information will be sent to and recorded in Storage 155 and Rules-Based Logic 135 will send relevant information with explanations to Patient UI 183 along with the directive to Caregiver UI 175 and Patient UI 183 at 4039, "Draw estradiol and progesterone." The provider will instruct the patient as to the directive, order the blood tests, and enter the results in Caregiver UI 175 which sends the information to Storage 155. Rules-Based Logic 135 will send relevant information with explanation to Patient UI 183 along with the next diagnostic step to Caregiver UI 175 at 4040, "Is progesterone 25 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4029 is no, then the information will be sent to and recorded in Storage 155 and Rules-Based Logic 135 will send relevant information with explanations to Patient UI 183 along with the next diagnostic step to Caregiver UI 175 at 4030, "Is FSH<4 mIU/mL?" The provider inputs the answer into Caregiver UI 175 which sends the information to Storage 155. Rules-Based Logic 135 then sends the next diagnostic step to Caregiver UI 175 depending on the previous answer.

If the answer at 4030 is yes, the information will be sent to and recorded in Storage 155 and Rules-Based Logic 135 will send relevant information with explanations to Patient UI 183 along with the next hard stop directive to Caregiver UI 175 and Patient UI 183 at 4038, "The patient needs injectable gonadotropins prescribed by a fertility clinic." The provider will instruct the patient as to the directive and provide counselling about adoption or a referral to a specialty center.

If the answer at 4030 is no, then the information will be sent to and recorded in Storage 155 and Rules-Based Logic 135 will send relevant information with explanations to Patient UI 183 along with the next diagnostic step to Caregiver UI 175 at 4031, "Is FSH 25 mIU/mL?" The provider inputs the answer into Caregiver UI 175 which sends the information to Storage 155. Rules-Based Logic 135 then sends the next diagnostic step to Caregiver UI 175 depending on the previous answer.

If the answer at 4031 is yes, then the information will be sent to and recorded in Storage 155 and Rules-Based Logic 135 will send relevant information with explanations to Patient UI 183 along with the next diagnostic step to Caregiver UI 175 at 4032, "is estradiol <200 pg/mL?" The provider inputs the answer into Caregiver UI 175 which sends the information to Storage 155. Rules-Based Logic 135 then sends the next diagnostic step to Caregiver UI 175 depending on the previous answer.

If the answer at 4031 is no, then the information will be sent to and recorded in Storage 155 and Rules-Based Logic 135 will send relevant information with explanations to Patient UI 183 along with the next diagnostic step to Caregiver UI 175 at 4035, "FSH mIU/mL >20?" The provider inputs the answer into Caregiver UI 175 which sends the information to Storage 155. Rules-Based Logic 135 then sends the next diagnostic step to Caregiver UI 175 depending on the previous answer.

If the answer at 4032 is yes, then the information will be sent to and recorded in Storage 155 and Rules-Based Logic 135 will send relevant information with explanations to Patient UI 183 along with the directive to Caregiver UI 175 at 4033, "No ovarian reserve; patient will need donor eggs and IVF". The provider will instruct the patient as to the directive and enter a confirmation. The algorithm comes to a hard stop and the patient receives counselling about adoption or a referral to a specialty center.

If the answer at 4032 is no, then the information will be sent to and recorded in Storage 155 and Rules-Based Logic 135 will send relevant information with explanations to Patient UI 183 along with the directive to Caregiver UI 175 and Patient UI 183 at 4034, "Patient appears to be currently ovulating." The provider will instruct the patient as to the directive and enters a confirmation into Caregiver UI 175 which sends the information to Storage 155. Rules-Based Logic 135 will send relevant information with explanation to Patient UI 183 along with the next diagnostic step to Caregiver UI 175 at 4097, "Does the patient have a personal history of miscarriage or a family history of deep vein thrombosis?" The provider inputs the answer into Caregiver UI 175 which sends the information to Storage 155. Rules-Based Logic 135 then sends the next directive or diagnostic step to Caregiver UI 175 depending on the previous answer.

If the answer at 4035 is yes, then the information will be sent to and recorded in Storage 155 and Rules-Based Logic 135 will send relevant information with explanations Patient UI 183 along with the directive to Caregiver UI 175 and Patient UI 183 at 4036, "Is estradiol ≥150 pg/mL?" The provider inputs the answer into Caregiver UI 175 which sends the information to Storage 155. Rules-Based Logic then sends the next directive to Caregiver UI 175 depending on the previous answer.

If the answer at 4035 is no, then the information will be sent to and recorded in Storage 155 and Rules-Based Logic 135 will send relevant information with explanations to Patient UI 183 along with the next diagnostic step to Caregiver UI 175 at 4097, "Does the patient have a personal history of miscarriage or a family history of deep vein thrombosis?" The provider inputs the answer into Caregiver UI 175 which sends the information to Storage 155. Rules-Based Logic 135 then sends the next diagnostic step to Caregiver UI 175 depending on the previous answer.

If the answer at 4036 is yes, then the information will be sent to and recorded in Storage 155 and Rules-Based Logic 135 will send relevant information with explanations to Patient UI 183 along with the directive to Caregiver UI 175 and Patient UI 183 at 4034, "Patient appears to be currently ovulating." The provider will instruct the patient as to the directive and enters a confirmation in Caregiver UI 175 which sends the information to Storage 155. Rules-Based Logic 135 will send relevant information with explanations Patient UI 183 along with the directive to Caregiver UI 175 at 4097, "Does the patient have a personal history of miscarriage or a family history of deep vein thrombosis?" The provider inputs the answer into Caregiver UI 175 which sends the information to Storage 155. Rules-Based Logic 135 then sends the next directive or diagnostic step to Caregiver UI 175 depending on the previous answer.

If the answer at 4036 is no, then the information will be sent to and recorded in Storage 155 and Rules-Based Logic 135 will send relevant information with explanations Patient UI 183 along with the hard stop directive to Caregiver UI 175 and Patient UI 183 at 4037, "Ovarian reserve is extremely limited, an IVF consult is recommended for patient." The provider will instruct the patient as to the directive and provide counselling about adoption or a referral to a specialty center.

If the answer at 4040 is yes, then the information will be sent to and recorded in Storage 155 and Rules-Based Logic 135 will send relevant information with explanations to Patient UI 183 along with the next diagnostic step to Caregiver UI 175 at 4041, "is the patient currently taking P4 supplements?" The provider inputs the answer into Caregiver UI 175 which sends the information to Storage 155. Rules-Based Logic 135 then sends the next diagnostic step to Caregiver UI 175 depending on the previous answer.

If the answer at 4040 is no, then the information will be sent to and recorded in Storage 155 and Rules-Based Logic 135 will send relevant information with explanations to Patient UI 183 along with the next diagnostic step to Caregiver UI 175 at 4052, "is estradiol=150 pg/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4041 is yes, the information will be sent to and recorded in Storage 155 and Rules-Based Logic 135 will send relevant information with explanations to Patient UI 183 along with the next diagnostic step to Caregiver UI 175 at 4042, "Is the patient currently taking progesterone in oil (50 mg/mL) 100 mg IM dose daily?" The provider inputs the answer into Caregiver UI 175 which sends the information to Storage 155. Rules-Based Logic 135 then sends the next diagnostic step to Caregiver UI 175 depending on the previous answer.

If the answer at 4041 is no, then the information will be sent to and recorded in Storage 155 and Rules-Based Logic 135 will send relevant information with explanations to Patient UI 183 along with the directive to Caregiver UI 175 at 4043, "Prescribe oral micronized progesterone 200 mg AM and PM. Then recheck progesterone in two days." The provider will instruct the patient as to the directive, prescribe the medication, order the lab tests, and enter the results in Caregiver UI 175 which sends the information to Storage 155. Rules-Based Logic 135 will send relevant information with explanations to Patient UI 183 along with the next diagnostic step to Caregiver UI 175 at 4040 "Is progesterone 25 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4042 is yes, then the information will be sent to and recorded in Storage 155 and Rules-Based Logic 135 will send relevant information with explanations to Patient UI 183 along with the next diagnostic step to Caregiver UI 175 at 4052, "Is estradiol ≥150 ng/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4042 is no, then the information will be sent to and recorded in Storage 155 and Rules-Based Logic 135 will send relevant information with explanations to Patient UI 183 along with the next diagnostic step to Caregiver UI 175 at 4046, "is the patient currently taking oral micronized progesterone 200 mg TID?" The provider inputs the answer into Caregiver UI 175 which sends the information to Storage 155. Rules-Based Logic 135 then sends the next directive or diagnostic step to Caregiver UI 175 depending on the previous answer.

If the answer at 4044 is yes, then the information will be sent to and recorded in Storage 155 and Rules-Based Logic 135 will send relevant information with explanations to Patient UI 183 along with the directive to Caregiver UI 175 at 4043, "Prescribe oral micronized progesterone 200 mg BID. Then recheck progesterone in two days." The provider will instruct the patient as to the directive, prescribe the medication, order the lab tests, and enter the results which sends the information to Storage 155. Rules-Based Logic 135 will send relevant information with explanations to Patient UI 183 along with the next diagnostic step to Caregiver UI 175 at 4040 "Is progesterone ≤25 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4044 is no, then the information will be sent to and recorded in Storage 155 and Rules-Based Logic 135 will send relevant information with explanations to Patient UI 183 along with the next diagnostic step to Caregiver UI 175 at 4047, "Is progesterone ≥18 & <22 ng/mL?" The provider inputs the answer into Caregiver UI 175 which sends the information to Storage 155. Rules-Based Logic 135 then sends the next directive to Caregiver UI 175 depending on the previous answer.

If the answer at 4045 is yes, then the information will be sent to and recorded in Storage 155 and Rules-Based Logic 135 will send relevant information with explanations to Patient UI 183 along with the next diagnostic step to Caregiver UI 175 at 4048, "Is progesterone ≥22 & ≤25 ng/mL?" The provider inputs the answer into Caregiver UI 175 which sends the information to Storage 155. Rules-Based Logic 135 then sends the next directive to Caregiver UI 175 depending on the previous answer.

If the answer at 4045 is no, then the information will be sent to and recorded in Storage 155 and Rules-Based Logic 135 will send relevant information with explanations to Patient UI 183 along with the next diagnostic step to Caregiver UI 175 at 4044, "Is P4≥22 & ≤25 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4046 is yes, then the information will be sent to and recorded in Storage 155 and Rules-Based Logic 135 will send relevant information with explanations to Patient UI 183 along with the next directive to Caregiver UI 175 at 4049, "Prescribe progesterone in oil (50 mg/mL) 100 mg IM dose daily." The provider will instruct the patient as to the directive, prescribe the medication, and enter a confirmation in Caregiver UI 175 which sends the information to Storage 155. Rules-Based Logic 135 then sends the next diagnostic step to Caregiver UI 175 at 4052, "Is estradiol >150 pg/ML?" The provider inputs the answer into Caregiver UI 175 which sends the information to Storage 155. Rules-Based Logic 135 then sends the next diagnostic step to Caregiver UI 175 depending on the previous answer.

If the answer at 4046 is no, then the information will be sent to and recorded in Storage 155 and Rules-Based Logic 135 will send relevant information with explanations to Patient UI 183 along with the next diagnostic step to Caregiver UI 175 at 4045, "Is the patient currently taking oral micronized progesterone 200 mg BID?" The provider inputs the answer into Caregiver UI 175 which sends the information to Storage 155. Rules-Based Logic 135 then sends the next directive to Caregiver UI 175 depending on the previous answer.

If the answer at 4047 is yes, then the information will be sent to and recorded in Storage 155 and Rules-Based Logic 135 will send relevant information with explanations to Patient UI 183 along with the next directive to Caregiver UI 175 at 4051, "Prescribe oral micronized progesterone 200 mg TID." The provider will instruct the patient as to the directive, prescribe the medication, and enter this compliance into Caregiver UI 175 which sends the information to Storage 155. Rules-Based Logic then sends the next diagnostic step to Caregiver UI 175 at 4052, "Is estradiol >150 pg/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4047 is no, then the information will be sent to and recorded in Storage 155 and Rules-Based Logic 135 will send relevant information with explanations to Patient UI 183 along with the next directive to Caregiver UI 175 at 4050, "Prescribe progesterone in oil (50 mg/mL) 100 mg IM dose daily." The provider will instruct the patient as to the directive, prescribe the medication, and enter this compliance into Caregiver UI 175 which sends the information to Storage 155. Rules-Based Logic then sends the next diagnostic step to Caregiver UI 175 at 4052, "Is estradiol >150 pg/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4048 is yes, then the information will be sent to and recorded in Storage 155 and Rules-Based Logic 135 will send relevant information with explanations to Patient UI 183 along with the next directive to Caregiver UI 175 at 4051, "Prescribe oral micronized progesterone 200 mg TID." The provider will instruct the patient as to the directive, prescribe the medication, and enter this compliance into Caregiver UI 175 which sends the information to Storage 155. Rules-Based Logic then sends the next diagnostic step to Caregiver UI 175 at 4052, "Is estradiol >150 pg/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4048 is no, then the information will be sent to and recorded in Storage 155 and Rules-Based Logic 135 will send relevant information with explanations to Patient UI 183 along with the next directive to Caregiver UI 175 at 4050, "Prescribe progesterone in oil (50 mg/mL) 100 mg IM dose daily." The provider will instruct the patient as to the directive, prescribe the medication, and enter this compliance into Caregiver UI 175 which sends the information to Storage 155. Rules-Based Logic then sends the next diagnostic step to Caregiver UI 175 at 4052, "Is estradiol >150 pg/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4052 is yes, then the information will be sent to and recorded in Storage 155 and Rules-Based Logic 135 will send relevant information with explanations to Patient UI 183 along with the next directive to Caregiver UI 175 at 4055, "Repeat hCG, estradiol, and progesterone levels 48 hours after most recent positive pregnancy test." The provider will instruct the patient as to the directive, order the lab tests, enter the results, and register this compliance into Caregiver UI 175 which sends the information to Storage 155. Rules-Based Logic will process the next diagnostic step to Caregiver UI 175 at 4057, "Was the increase in hCG<65%?" The provider inputs the answer into Caregiver UI 175 which sends the information to Storage 155. Rules-Based Logic 135 then sends the next directive or diagnostic step to Caregiver UI 175 depending on the previous answer.

If the answer at 4052 is no, then the information will be sent to and recorded in Storage 155 and Rules-Based Logic 135 will send relevant information with explanations to Patient UI 183 along with the next diagnostic step to Caregiver UI 175 at 4053, "Is patient talking micronized estradiol?" The provider inputs the answer into Caregiver UI 175 which sends the information to Storage 155. Rules-Based Logic 135 then sends the next diagnostic step to Caregiver UI 175 depending on the previous answer.

If the answer at 4053 is yes, then the information will be sent to and recorded in Storage 155 and Rules-Based Logic 135 will send relevant information with explanations to Patient UI 183 along with the next directive to Caregiver UI 175 at 4056, "Increase supplemental dose of micronized estradiol by 2 mg PO per day." The provider will instruct the patient as to the directive, prescribe the medication, and enter this compliance into Caregiver UI 175 which sends the information to Storage 155. Rules-Based Logic then sends the next directive to Caregiver UI 175 at 4055, "Repeat hCG, estradiol, and progesterone levels 48 hours after most recent positive pregnancy test." The provider will instruct the patient as to the directive, order the lab tests, enter the results, and register this compliance into Caregiver UI 175 which sends the information to Storage 155. Rules-Based Logic 135 will process the next diagnostic step at 4057, "Was the increase in hCG <65%?" The provider inputs the answer into Caregiver UI 175 which sends the information to Storage 155. Rules-Based Logic 135 then sends the next directive or diagnostic step to Caregiver UI 175 depending on the previous answer.

If the answer at 4053 is no, then the information will be sent to and recorded in Storage 155 and Rules-Based Logic 135 will send relevant information with explanations to Patient UI 183 along with the next directive to Caregiver UI 175 at 4054, "Prescribe micronized estradiol 2 mg PO BID." The provider will instruct the patient as to the directive, prescribe the medication, and enter this compliance into Caregiver UI 175 which sends the information to Storage 155. Rules-Based Logic then sends the next directive to Caregiver UI 175 at 4055, "Repeat hCG, estradiol, and progesterone levels 48 hours after most recent positive pregnancy test." The provider will instruct the patient as to the directive, order the lab tests, enter the results, and register this compliance into Caregiver UI 175 which sends the information to Storage 155. Rules-Based Logic 135 will process the next diagnostic step at 4057, "Was the increase in hCG <65%?" The provider inputs the answer into Caregiver UI 175 which sends the information to Storage 155. Rules-Based Logic 135 then sends the next directive or diagnostic step to Caregiver UI 175 depending on the previous answer.

If the answer at 4057 is yes, then the information will be sent to and recorded in Storage 155 and Rules-Based Logic 135 will send relevant information with explanations to Patient UI 183 along with the next directive to Caregiver UI 175 at 4058, "Stop estradiol and progesterone supplements." The provider will instruct the patient as to the directive and enter this compliance into Caregiver UI 175 which sends the information to Storage 155. Rules-Based Logic 135 will send relevant information with explanations to Patient UI 183 along with the next directive 4059, "Recheck hCG in one week." The provider will instruct the patient as to the directive, order the lab test, enter the result, and register this compliance into Caregiver UI 175 which sends the information to Storage 155. Rules-Based Logic 135 will process the data from 4059 in the next diagnostic step at 4060, "Is this hCG value less than the previous one?" Rules-Based Logic will access Storage 155 and Information Library 160. Rules-Based Logic shares relevant information and explanations to Patient UI 183 along with the next diagnostic step to Caregiver UI 175 depending on the previous answer.

If the answer at 4057 is no, then the information will be sent to and recorded in Storage 155 and Rules-Based Logic 135 will send relevant information with explanations to Patient UI 183 along with the next diagnostic step to Caregiver UI 175 at 4065, "Is progesterone <25 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4060 is yes, then the information will be sent to and recorded in Storage 155 and Rules-Based Logic 135 will send relevant information with explanations to Patient UI 183 along with the next diagnostic step to Caregiver UI 175 at 4061, "Is hCG≥5 mIU/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4060 is no, then the information will be sent to and recorded in Storage 155 and Rules-Based Logic 135 will send relevant information with explanations to Patient UI 183 along with the next diagnostic step to Caregiver UI 175 at 4062, "Is Urine hCG Positive?" The provider inputs the answer into Caregiver UI 175 which sends the information to Storage 155. Rules-Based Logic 135 then sends the next diagnostic step to Caregiver UI 175 depending on the previous answer.

If the answer at 4061 is yes, then the information will be sent to and recorded in Storage 155 and Rules-Based Logic 135 will send relevant information with explanations to Patient UI 183 along with the next directive to Caregiver UI 175 at 4059, "Recheck hCG in one week." The provider will instruct the patient as to the directive, order the lab tests, enter the results, and register this compliance into Caregiver UI 175 which sends the information to Storage 155. Rules-Based Logic 135 will process the next diagnostic step at 4060, "Is the hCG value less than the previous one?" Comparison of results are made at the Information Library 160 and conclusions sent to the Caregiver UI 175 and recorded in Storage 155. The provider inputs the answer into Caregiver UI 175 which sends the information to Storage 155. Rules-Based Logic 135 then sends the next diagnostic step to Caregiver UI 175 depending on the previous answer.

If the answer at 4061 is no, then the information will be sent to and recorded in Storage 155 and Rules-Based Logic 135 will send relevant information with explanations to Patient UI 183 along with the next diagnostic step to Caregiver UI 175 at 4098, "Has the patient been tested for the presence of anticardiolipin antibodies, lupus anticoagulant, anti-beta2-glycoprotein 1 antibodies, and Factor V Leiden mutation?" The provider inputs the answer into Caregiver UI 175 which sends the information to Storage 155. Rules-Based Logic 135 then sends the next diagnostic step to Caregiver UI 175 depending on the previous answer.

If the answer at 4062 is yes, then the information will be sent to and recorded in Storage 155 and Rules-Based Logic 135 will send relevant information with explanations to Patient UI 183 along with the next directive to Caregiver UI 175 at 4063, "Prescribe methotrexate 1 mg/kg IM and avoid folic acid." The provider prescribes and administers the medication, then enters compliance information into Caregiver UI 175 which is then sent to Storage 155. Rules-Based Logic then sends the next directive to Caregiver UI 175 at 4059, "Recheck hCG in one week." The provider will instruct the patient as to the directive, order the blood test, and enter the result in Caregiver UI 175 and Storage 155. The data will be assessed via Knowledge Graph 150 and addressed in the Information Library 160. Rules-Based Logic 135 will send relevant information with explanations to Patient UI 183 along with the next step to Caregiver UI 175 at 4060, "Is this hCG value less than the previous one?" Comparison of results are made at the Information Library 160, recorded at Status Storage 165, and conclusions sent to the Caregiver UI 175. The provider confirms the answer into Caregiver UI 175 which sends the information to Storage 155. Rules-Based Logic 135 then sends the next diagnostic step to Caregiver UI 175 depending on the previous answer.

If the answer at 4062 is no, then the information will be sent to and recorded in Storage 155 and Rules-Based Logic 135 will send relevant information with explanations to Patient UI 183 along with the next step to Caregiver UI 175 at 4098, "Has the patient been tested for the presence of anticardiolipin antibodies, lupus anticoagulant, anti-beta2-glycoprotein 1 antibodies, and Factor V Leiden mutation?" The provider inputs the answer into Caregiver UI 175 which sends the information to Storage 155. Rules-Based Logic 135 then sends the next diagnostic step to Caregiver UI 175 depending on the previous answer.

If the answer at 4065 is yes, then the information will be sent to and recorded in Storage 155 and Rules-Based Logic 135 will send relevant information with explanations to Patient UI 183 along with the next diagnostic step to Caregiver UI 175 at 4041, "Is the patient currently taking progesterone supplements?" The provider inputs the answer into Caregiver UI 175 which sends the information to Storage 155. Rules-Based Logic 135 then sends the next directive or diagnostic step to Caregiver UI 175 depending on the previous answer.

If the answer at 4065 is no, then the information will be sent to and recorded in Storage 155 and Rules-Based Logic 135 will send relevant information with explanations to Patient UI 183 along with the next diagnostic step to Caregiver UI 175 at 4066, "Does the patient have a history of tubal disease (ectopic pregnancy, tubal occlusion, tubal recanalization)?" The provider inputs the answer into Caregiver UI 175 which sends the information to Storage 155. Rules-Based Logic 135 then sends the next directive to Caregiver UI 175 depending on the previous answer.

If the answer at 4066 is yes, then the information will be sent to and recorded in Storage 155 and Rules-Based Logic 135 will send relevant information with explanations to Patient UI 183 along with the next directive to Caregiver UI 175 at 4068, "Ultrasound at 3 weeks post conception." The provider will instruct the patient as to the directive, order the study for the patient, and enter the results in Caregiver UI 175 and Storage 155. Rules-Based Logic 135 and Knowledge Graph 150 will assess the next diagnostic step at 4069, "is a gestational sac seen within the uterus?" The provider inputs the answer into Caregiver UI 175 which sends the information to Storage 155. Rules-Based Logic 135 then sends the next directive to Caregiver UI 175 depending on the previous answer.

If the answer at 4066 is no, then the information will be sent to and recorded in Storage 155 and Rules-Based Logic 135 will send relevant information with explanations to Patient UI 183 along with the next directive to Caregiver UI 175 at 4067, "Ultrasound for fetal viability at 5 weeks post conception." The provider will instruct the patient as to the directive, order the study for the patient, and enter the results in Caregiver UI 175 and Storage 155. Rules-Based Logic 135 and Knowledge Graph 150 will assess the information. Rules-Based Logic will then send the next diagnostic step at 4075, "Are fetal pole and yolk sac present?" The provider inputs the answer into Caregiver UI 175 which sends the information to Storage 155. Rules-Based Logic 135 then sends the next directive or diagnostic step to Caregiver UI 175 depending on the previous answer.

If the answer at 4069 is yes, then the information will be sent to and recorded in Storage 155 and Rules-Based Logic 135 will send relevant information with explanations to Patient UI 183 along with the next directive to Caregiver UI 175 at 4067, "Ultrasound for fetal viability at 5 weeks post conception." The provider will instruct the patient as to this directive, order the study for the patient and enter the results in Caregiver UI 175 and Storage 155. Rules-Based Logic 135 and Knowledge Graph 150 will assess the information. Rules-Based Logic will then send the next diagnostic step at 4075, "Are fetal pole and yolk sac present?" The provider inputs the answer into Caregiver UI 175 which sends the information to Storage 155. Rules-Based Logic 135 then sends the next directive or diagnostic step to Caregiver UI 175 depending on the previous answer.

If the answer at 4069 is no, then the information will be sent to and recorded in Storage 155 and Rules-Based Logic 135 will send relevant information with explanations to Patient UI 183 along with the next directive to Caregiver UI 175 at 4070, "Recheck hCG level." The provider will instruct the patient as to the directive, order the blood test for the patient, and enter the result in Caregiver UI 175 and Storage 155. Rules-Based Logic 135 and Knowledge Graph 150 will assess the information and send the next diagnostic step at 4071, "Is hCG>1000 mIU/mL?" The provider inputs the answer into Caregiver UI 175 which sends the information to Storage 155. Rules-Based Logic 135 then sends the next directive to Caregiver UI 175 depending on the previous answer.

If the answer at 4071 is yes, then the information will be sent to and recorded in Storage 155 and Rules-Based Logic 135 will send relevant information with explanations to Patient UI 183 along with the next directive to Caregiver UI 175 at 4072, "Repeat ultrasound at 4 weeks post conception." The provider will instruct the patient as to the directive, order the study for the patient, and enter the results in Caregiver UI 175 and Storage 155. Rules-Based Logic 135 and Knowledge Graph 150 will assess the information and send the next diagnostic step at 4073, "is a gestational sac within the uterus?" The provider inputs the answer into Caregiver UI 175 which sends the information to Storage 155. Rules-Based Logic 135 then sends the next directive to Caregiver UI 175 depending on the previous answer.

If the answer at 4071 is no, then the information will be sent to and recorded in Storage 155 and Rules-Based Logic 135 will send relevant information with explanations to Patient UI 183 along with the next directive to Caregiver UI 175 at 4058, "Stop estradiol and progesterone supplements." The provider will instruct the patient as to this directive, order the blood test, enter the result in Caregiver UI 175 and Storage 155. Rules-Based Logic 135 will send relevant information with explanations to Patient UI 183 along with the next directive to Caregiver UI 175 at 4059, "Recheck hCG in one week." The provider will instruct the patient as to the directive, order the blood test for the patient, and enter the result in Caregiver UI 175 and Storage 155. Rules-Based Logic 135 and Knowledge Graph 150 will compare results in the Information Library 160 and present the next diagnostic step at 4060, "Is this hCG value less than the previous one?" The provider inputs the answer into Caregiver UI 175 which sends the information to Storage 155. Rules-Based Logic 135 then sends the next directive to Caregiver UI 175 depending on the previous answer.

If the answer at 4073 is yes, then the information will be sent to and recorded in Storage 155 and Rules-Based Logic 135 will send relevant information with explanations to Patient UI 183 along with the next directive to Caregiver UI 175 at 4074, "Repeat ultrasound at 5 weeks post conception." The provider will instruct the patient as to the directive, order the study for the patient, and enter the results in Caregiver UI 175 and Storage 155. Rules-Based Logic 135 and Knowledge Graph 150 will assess the information and send the next diagnostic step at 4075, "Are fetal pole and yolk sac present?" The provider inputs the answer into Caregiver UI 175 which sends the information to Storage 155. Rules-Based Logic 135 then sends the next directive or diagnostic step to Caregiver UI 175 depending on the previous answer.

If the answer at 4073 is no, then the information will be sent to and recorded in Storage 155 and Rules-Based Logic 135 will send relevant information with explanations to Patient UI 183 along with the next directive to Caregiver UI 175 at 4064, "Stop estradiol and progesterone supplements." The provider will instruct the patient as to this directive, confirm the communication, and proceed to the next directive at 4063, "Prescribe methotrexate 1 mg/kg IM and avoid folic acid." The provider will instruct the patient as to this directive, prescribe and administer the medication, then confirm compliance in Caregiver UI 175 and Storage 155. Rules-Based Logic 135 will send relevant information with explanations to Patient UI 183 along with the next directive to Caregiver UI 175 at 4059, "Recheck hCG in one week." The provider will instruct the patient as to this directive, order the blood test, enter the result in Caregiver UI 175 and Storage 155. Rules-Based Logic 135 and Knowledge Graph 150 will compare results in the Information Library 160 and present the next diagnostic step at 4060, "Is this hCG value less than the previous one?" Results are shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4075 is yes, then the information will be sent to and recorded in Storage 155 and Rules-Based Logic 135 will send relevant information with explanations to Patient UI 183 along with the next diagnostic step to Caregiver UI 175 at 4077, "Is fetal cardiac activity seen?" The provider inputs the answer into Caregiver UI 175 which sends the information to Storage 155. Rules-Based Logic 135 then sends the next directive to Caregiver UI 175 depending on the previous answer.

If the answer at 4075 is no, then the information will be sent to and recorded in Storage 155 and Rules-Based Logic 135 will send relevant information with explanations to Patient UI 183 along with the next directive to Caregiver UI 175 at 4076, "Stop estradiol and progesterone supplements and allow miscarriage or perform suction D&C." The provider will instruct the patient as to this directive and proceed according to patient preference and confirm compliance in Caregiver UI 175 and Storage 155. Rules-Based Logic 135 will send relevant information with explanations to Patient UI 183 along with the next directive to Caregiver UI 175 at 4059, "Recheck hCG in one week." The provider will instruct the patient as to this directive, order the blood test, enter the result in Caregiver UI 175 and Storage 155. Rules-Based Logic 135 and Information Library 160 will assess the next diagnostic step at 4060, "Is this hCG value less than the previous one?" The information is shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4077 is yes, then the information will be sent to and recorded in Storage 155 and Rules-Based Logic 135 will send relevant information with explanations to Patient UI 183 along with the next directive to Caregiver UI 175 at 4080, "Recheck estradiol and progesterone at 10 weeks post conception and begin Standardized Obstetric Care," The provider will instruct the patient as to this directive, order the blood tests, enter the results in Caregiver UI 175 and Storage 155. Rules-Based Logic 135 and Information Library 160 will assess the next diagnostic step at 4081, "Is progesterone level <40 ng/mL?" The provider inputs the answer into Caregiver UI 175 which sends the information to Storage 155. Rules-Based Logic 135 then sends the next directive to Caregiver UI 175 depending on the previous answer.

If the answer at 4077 is no, then the information will be sent to and recorded in Storage 155 and Rules-Based Logic 135 will send relevant information with explanations to Patient UI 183 along with the next directive to Caregiver UI 175 at 4078, "Recheck ultrasound for cardiac activity at 6 weeks post conception." The provider will instruct the patient as to this directive, order the study, and enter the results in Caregiver UI 175 and Storage 155. Rules-Based Logic 135 and Knowledge Graph 150 will assess the next diagnostic step at 4079, "is fetal cardiac activity present?" The provider inputs the answer into Caregiver UI 175 which sends the information to Storage 155. Rules-Based Logic 135 then sends the next directive or diagnostic step to Caregiver UI 175 depending on the previous answer.

If the answer at 4079 is yes, then the information will be sent to and recorded in Storage 155 and Rules-Based Logic 135 will send relevant information with explanations to Patient UI 183 along with the next directive to Caregiver UI 175 at 4080, "Recheck estradiol and progesterone at 10 weeks post conception and begin Standardized Obstetric Care." The provider will instruct the patient as to this directive, order the blood tests, enter the results in Caregiver UI 175 and Storage 155. Rules-Based Logic 135 and Knowledge Graph 150 will assess the next diagnostic step at 4081, "Is progesterone level <40 ng/mL?" The results are shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4079 is no, then the information will be sent to and recorded in Storage 155 and Rules-Based Logic 135 will send relevant information with explanations to Patient UI 183 along with the next directive to Caregiver UI 175 at 4076, "Stop estradiol and progesterone supplements and allow miscarriage or perform suction D&C." The provider will instruct the patient as to this directive and proceed according to patient preference and confirm compliance in Caregiver UI 175 and Storage 155. Rules-Based Logic 135 will send relevant information with explanations to Patient UI 183 along with the next directive to Caregiver UI 175 at 4059, "Recheck hCG in one week." The provider will instruct the patient as to this directive, order the blood tests, enter the results in Caregiver UI 175 and Storage 155. Rules-Based Logic 135 and Knowledge Graph 150 will assess the next diagnostic step at 4060, "Is this hCG value less than the previous one?" The information is shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4081 is yes, then the information will be sent to and recorded in Storage 155 and Rules-Based Logic 135 will send relevant information with explanations to Patient UI 183 along with the next directive to Caregiver UI 175 at 4089, "Ultrasound for viability." The provider will instruct the patient as to this directive, order the study for the patient and enter the results in Caregiver UI 175 and Storage 155. Rules-Based Logic 135 and Knowledge Graph 150 will assess the next diagnostic step at 4095, "is fetal cardiac activity seen?" The results are shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4081 is no, then the information will be sent to and recorded in Storage 155 and Rules-Based Logic 135 will send relevant information with explanations to Patient UI 183 along with the next directive to Caregiver UI 175 at 4082, "Discontinue progesterone supplements." The provider will instruct the patient as to this directive and enter confirmation in Caregiver UI 175 and Storage 155. Rules-Based Logic 135 will send relevant information with explanations to Patient UI 183 along with the next diagnostic step to Caregiver UI 175 at 4083, "is estradiol ≥400 pg/mL?" The information is shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4083 is yes, then the information will be sent to and recorded in Storage 155 and Rules-Based Logic 135 will send relevant information with explanations to Patient UI 183 along with the next directive to Caregiver UI 175 at 4086, "Stop estradiol supplementation. Recheck estradiol and progesterone in 2 days." The provider will instruct the patient as to this directive, order the blood tests, enter the results, and register confirmation in Caregiver UI 175 and Storage 155. Rules-Based Logic 135 will send relevant information with explanations to Patient UI 183 along with the next diagnostic step to Caregiver UI 175 at 4087, "is progesterone y 25 ng/mL?" The information is shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4083 is no, then the information will be sent to and recorded in Storage 155 and Rules-Based Logic 135 will send relevant information with explanations to Patient UI 183 along with the next diagnostic step to Caregiver UI 175 at 4084, "Is patient taking estradiol supplements?" The provider inputs the answer into Caregiver UI 175 which sends the information to Storage 155. Rules-Based Logic 135 then sends the next directive or diagnostic step to Caregiver UI 175 depending on the previous answer.

If the answer at 4084 is yes, then the information will be sent to and recorded in Storage 155 and Rules-Based Logic 135 will send relevant information with explanations to Patient UI 183 along with the next directive to Caregiver UI 175 at 4085, "Continue estradiol supplements for another 2 weeks, then recheck level." The provider will instruct the patient as to this directive, order the blood test, enter the result, and register confirmation in Caregiver UI 175 and Storage 155. Rules-Based Logic 135 will send relevant information with explanations to Patient UI 183 along with the next diagnostic step to Caregiver UI 175 at 4083, "Is estradiol ≥400 pg/mL?" The information is shared in Caregiver UI 175 and Patient UI 183. The provider inputs the answer into Caregiver UI 175 which sends the information to Storage 155. Rules-Based Logic 135 then sends the next directive or diagnostic step to Caregiver UI 175 depending on the previous answer.

If the answer at 4084 is no, then the information will be sent to and recorded in Storage 155 and Rules-Based Logic 135 will send relevant information with explanations to Patient UI 183 along with the next diagnostic step to Caregiver UI 175 at 4087, "Is progesterone ≥25 ng/mL?" The information is shared in Caregiver UI 175 and Patient UI 183. The provider inputs the answer into Caregiver UI 175 which sends the information to Storage 155. Rules-Based Logic 135 then sends the next directive or diagnostic step to Caregiver UI 175 depending on the previous answer.

If the answer at 4087 is yes, then the information will be sent to and recorded in Storage 155 and Rules-Based Logic 135 will send relevant information with explanations to Patient UI 183 along with the next hard stop directive to Caregiver UI 175 at 4088, "Recheck ultrasound and continue obstetrical care without estradiol or progesterone supplementation." The provider will instruct the patient as to this directive, order the study for the patient and enter the results in Caregiver UI 175 and Storage 155. The algorithm will close.

If the answer at 4087 is no, then the information will be sent to and recorded in Storage 155 and Rules-Based Logic 135 will send relevant information with explanations to Patient UI 183 along with the next directive to Caregiver UI 175 at 4094, "Prescribe micronized progesterone 200 mg PO BID and Ultrasound for viability." The provider will instruct the patient as to this directive, order the medication and the study, and enter the results in Caregiver UI 175 and Storage 155. Rules-Based Logic 135 and Knowledge Graph 150 will assess the next diagnostic step at 4095, "is fetal cardiac activity seen?" The results are shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4090 is yes, then the information will be sent to and recorded in Storage 155 and Rules-Based Logic 135 will send relevant information with explanations to Patient UI 183 along with the next diagnostic step to Caregiver UI 175 at 4091, "Is progesterone ≥25 ng/mL?" The results are shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4090 is no, then the information will be sent to and recorded in Storage 155 and Rules-Based Logic 135 will send relevant information with explanations to Patient UI 183 along with the next directive to Caregiver UI 175 at 4076, "Stop estradiol and progesterone supplements and allow miscarriage or perform suction D&C." The provider will instruct the patient as to this directive and proceed according to patient preference and confirm compliance in Caregiver UI 175 and Storage 155. Rules-Based Logic 135 will send relevant information with explanations to Patient UI 183 along with the next directive to Caregiver UI 175 at 4059, "Recheck hCG in one week." The provider will instruct the patient as to this directive, order the blood tests, enter the results in Caregiver UI 175 and Storage 155. Rules-Based Logic 135 and Knowledge Graph 150 will assess the next diagnostic step at 4060, "Is this hCG value less than the previous one?" The information is shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4091 is yes, then the information will be sent to and recorded in Storage 155 and Rules-Based Logic 135 will send relevant information with explanations to Patient UI 183 along with the next directive to Caregiver UI 175 at 4093, "Continue supplements and recheck estradiol and progesterone in 2 weeks." The provider will instruct the patient as to this directive, order the blood tests, and enter the results in Caregiver UI 175 and Storage 155. Rules-Based Logic 135 and Knowledge Graph 150 will assess the next diagnostic step at 4081, "Is progesterone level <40 ng/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4091 is no, then the information will be sent to and recorded in Storage 155 and Rules-Based Logic 135 will send relevant information with explanations to Patient UI 183 along with the next directive to Caregiver UI 175 at 4092, "Progesterone supplementation should be 200 mg 3 times daily." The provider will instruct the patient as to this directive, make needed changes to the progesterone dosing, record it in Storage 155, and then communicate this directive through Patient UI 183. Rules-Based Logic 135 and Knowledge Graph 150 will then proceed to the next directive at 4093, "Continue supplements and recheck estradiol and progesterone in 2 weeks." The provider will order the study for the patient and enter the results in Caregiver UI 175 and Storage 155. Rules-Based Logic 135 and Knowledge Graph 150 will assess the next diagnostic step at 4081, "Is progesterone level <40 ng/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4095 is yes, then the information will be sent to and recorded in Storage 155 and Rules-Based Logic 135 will send relevant information with explanations to Patient UI 183 along with the next directive to Caregiver UI 175 at 4096, "Check estradiol and progesterone levels in 2 days." The provider will instruct the patient as to this directive, order the blood tests, and enter the results in Caregiver UI 175 and Storage 155. Rules-Based Logic 135 and Knowledge Graph 150 will assess the next diagnostic step at 4081, "Is progesterone level <40 ng/mL?" The results are shared in Caregiver UI 175 and Patient UI 183 The provider inputs the answer into Caregiver UI 175 which sends the information to Storage 155. Rules-Based Logic 135 then sends the next directive or diagnostic step to Caregiver UI 175 depending on the previous answer.

If the answer at 4095 is no, then the information will be sent to and recorded in Storage 155 and Rules-Based Logic 135 will send relevant information with explanations to Patient UI 183 along with the next directive to Caregiver UI 175 at 4076, "Stop estradiol and progesterone supplements and allow miscarriage or perform suction D&C." The provider will instruct the patient as to this directive and then proceed according to patient preference. Results will be entered into Caregiver UI 175 and Storage 155. Rules-Based Logic 135 and Knowledge Graph 150 will assess the information at 4059, "Recheck hCG in one week." The provider will instruct the patient as to this directive, order the blood tests, and enter the results in Caregiver UI 175 and Storage 155. Rules-Based Logic 135 and Information Library 160 will assess the next diagnostic step at 4060, "Is this hCG value less than the previous one?" The information is shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4097 is yes, then the information will be sent to and recorded in Storage 155 and Rules-Based Logic 135 will send relevant information with explanations to Patient UI 183 along with the next diagnostic step to Caregiver UI 175 at 4098, "Has the patient been tested for the presence of anticardiolipin antibodies, lupus anticoagulant, anti-beta2-glycoprotein 1 antibodies, and Factor V Leiden mutation?" The information is shared in Caregiver UI 175 and Patient UI 183. The provider inputs the answer into Caregiver UI 175 which sends the information to Storage 155. Rules-Based Logic 135 then sends the next directive or diagnostic step to Caregiver UI 175 depending on the previous answer.

If the answer at 4097 is no, then the information will be sent to and recorded in Storage 155 and Rules-Based Logic 135 will send relevant information with explanations to Patient UI 183 along with the next directive to Caregiver UI 175 at 4102, "Baseline blood tests are to be drawn in the morning and before eating breakfast: TSH, prolactin, DHEA-S, 17-OH progesterone, CBC, CMP, and insulin. Also add this cycle's Day 2 (or 3) estradiol and FSH. (Bring on a withdrawal bleed using Provera 10 mg for 10 days, if necessary.)" The provider will instruct the patient as to this directive, order the blood tests, and enter the results in Caregiver UI 175 and Storage 155. Rules-Based Logic 135 and Knowledge Graph 150 will assess the next diagnostic step at 4103, "Is TSH<0.6 mIU/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4098 is yes, then the information will be sent to and recorded in Storage 155 and Rules-Based Logic 135 will send relevant information with explanations to Patient UI 183 along with the next diagnostic step to Caregiver UI 175 at 4100, "Were any of these positive?" The results are shared in Caregiver UI 175 and Patient UI 183. The provider inputs the answer into Caregiver UI 175 which sends the information to Storage 155. Rules-Based Logic

135 then sends the next directive step to Caregiver UI 175 depending on the previous answer.

If the answer at 4098 is no, then the information will be sent to and recorded in Storage 155 and Rules-Based Logic 135 will send relevant information with explanations to Patient UI 183 along with the next directive to Caregiver UI 175 at 4099, "Test for the presence of anticardiolipin antibodies, lupus anticoagulant, anti-beta2-glycoprotein 1 antibodies, and Factor V Leiden mutation now." The provider will instruct the patient as to this directive, order the blood tests, and enter the results in Caregiver UI 175 and Storage 155. Rules-Based Logic 135 and Knowledge Graph 150 will assess the next diagnostic step at 4100, "Were any of these positive?" The results are shared in Caregiver UI 175 and Patient UI 183. The provider inputs the answer into Caregiver UI 175 which sends the information to Storage 155. Rules-Based Logic 135 then sends the next directive to Caregiver UI 175 depending on the previous answer.

If the answer at 4100 is yes, then the information will be sent to and recorded in Storage 155 and Rules-Based Logic 135 will send relevant information with explanations to Patient UI 183 along with the next directive to Caregiver UI 175 and Patient UI 183 at 4101, "Prescribe enoxaparin 40 mg injection and aspirin 81 mg orally, daily during next pregnancy." The provider will instruct the patient as to this directive, order the medications, and enter confirmation in Caregiver UI 175 and Storage 155. Rules-Based Logic 135 and Knowledge Graph 150 will proceed to the next directive to Caregiver UI 175 and Patient UI 183 at 4102, "Baseline blood tests are to be drawn in the morning and before eating breakfast: TSH, prolactin, DHEA-S, 17-OH progesterone, CBC, CMP, and insulin. Also add this cycle's Day 2 (or 3) estradiol and FSH. (Bring on a withdrawal bleed using Provera 10 mg for 10 days, if necessary.)" The provider will instruct the patient as to this directive, order the blood tests, and enter the results in Caregiver UI 175 and Storage 155. Rules-Based Logic 135 and Knowledge Graph 150 will assess the next diagnostic step at 4103, "Is TSH<0.6 mIU/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4100 is no, then the information will be sent to and recorded in Storage 155 and Rules-Based Logic 135 will send relevant information with explanations to Patient UI 183 along with the next directive to Caregiver UI 175 and Patient UI 183 at 4102, "Baseline blood tests are to be drawn in the morning and before eating breakfast: TSH, prolactin, DHEA-S, 17-OH progesterone, CBC, CMP, and insulin. Also add this cycle's Day 2 (or 3) estradiol and FSH. (Bring on a withdrawal bleed using Provera 10 mg for 10 days, if necessary.)" The provider will instruct the patient as to this directive, order the blood tests, and enter the results in Caregiver UI 175 and Storage 155. Rules-Based Logic 135 and Knowledge Graph 150 will assess the next diagnostic step at 4103, "Is TSH<0.6 mIU/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4103 is yes, then the information will be sent to and recorded in Storage 155 and Rules-Based Logic 135 will send relevant information with explanations to Patient UI 183 along with the next diagnostic step to Caregiver UI 175 at 4104, "Is the patient taking Propylthiouracil or Methimazole?" The provider inputs the answer into Caregiver UI 175 which sends the information to Storage 155. Rules-Based Logic 135 then sends the next diagnostic step to Caregiver UI 175 depending on the previous answer.

If the answer at 4103 is no, then the information will be sent to and recorded in Storage 155 and Rules-Based Logic 135 will send relevant information with explanations to Patient UI 183 along with the next diagnostic step to Caregiver UI 175 at 4110, "Is TSH>2 and <5 mIU/mL?" The provider inputs the answer into Caregiver UI 175 which sends the information to Storage 155. Rules-Based Logic 135 then sends the next diagnostic step to Caregiver UI 175 depending on the previous answer.

If the answer at 4104 is yes, then the information will be sent to and recorded in Storage 155 and Rules-Based Logic 135 will send relevant information with explanations to Patient UI 183 along with the next directive and hard stop to Caregiver UI 175 at 4122, "Refer to an endocrinologist." The provider will instruct the patient as to this directive and input the confirmation in Caregiver UI 175 which sends the information to Storage 155. Upon compliance to this directive, the patient will resume at the beginning of the algorithm.

If the answer at 4104 is no, then the information will be sent to and recorded in Storage 155 and Rules-Based Logic 135 will send relevant information with explanations to Patient UI 183 along with the next diagnostic step to Caregiver UI 175 at 4105, "Does the patient have a palpable thyroid nodule?" The provider will instruct the patient as to this directive, carefully palpate the patient's thyroid gland, and input the answer into Caregiver UI 175 which sends the information to Storage 155. Rules-Based Logic 135 then sends the next directive or diagnostic step to Caregiver UI 175 depending on the previous answer.

If the answer at 4105 is yes, then the information will be sent to and recorded in Storage 155 and Rules-Based Logic 135 will send relevant information with explanations to Patient UI 183 along with the next directive and hard stop to Caregiver UI 175 at 4122, "Refer to an endocrinologist." The provider will instruct the patient as to this directive, make the referral, and input confirmation in Caregiver UI 175 which sends the information to Storage 155. Upon compliance to this directive, the patient will resume at the beginning of the algorithm.

If the answer at 4105 is no, then the information will be sent to and recorded in Storage 155 and Rules-Based Logic 135 will send relevant information with explanations to Patient UI 183 along with the next diagnostic step to Caregiver UI 175 at 4106, "Is the Hepatic Function Panel normal?" The provider inputs the answer into Caregiver UI 175 which sends the information to Storage 155. Rules-Based Logic then sends the next directive to Caregiver UI 175 depending on the previous answer.

If the answer at 4106 is yes, then the information will be sent to and recorded in Storage 155 and Rules-Based Logic 135 will send relevant information with explanations to Patient UI 183 along with the next directive to Caregiver UI 175 at 4107, "Check patient's Free T3 and Free T4." The provider will instruct the patient as to this directive, order the blood tests, and enter the results into Caregiver UI 175 and Storage 155. The Expert System 110 will process these data and Rules Based Logic 135 will send relevant information with explanations to Patient UI 183 along with the next diagnostic step to Caregiver UI 175 at 4108, "Is Free T3≥4.1 pg/mL or T4>12 µg/dL?" Results will be entered in Caregiver UI 175 and Storage 155. The provider inputs the answer into Caregiver UI 175 which sends the information to Storage 155. Rules-Based Logic 135 then sends the next diagnostic step to Caregiver UI depending on the previous answer.

If the answer at 4106 is no, then the information will be sent to and recorded in Storage 155 and Rules-Based Logic 135 will send relevant information with explanations to Patient UI 183 along with the next directive and hard stop to Caregiver UI 175 at 4122, "Refer to an endocrinologist." The provider will instruct the patient as to this directive, make the referral, and input confirmation in Caregiver UI 175 which sends the information to Storage 155. Upon compliance to this directive, the patient will resume at the beginning of the algorithm.

If the answer at 4108 is yes, then the information will be sent to and recorded in Storage 155 and Rules-Based Logic 135 will send relevant information with explanations to Patient UI 183 along with the next directive to Caregiver UI 175 at 4109, "Prescribe propylthiouracil 50 mg BID×7 days. Then, 50 mg TID thereafter and recheck TSH in 1 month." The provider will instruct the patient as to this directive, prescribe the medication, order the blood test, and enter the result into Caregiver UI 175 which sends the information to Storage 155. Rules-Based Logic 135 and Knowledge Graph 150 will assess the information. Rules-Based Logic 135 then sends the next diagnostic step to Caregiver UI 175 at 4103, "Is TSH<0.6 mIU/mL?" The provider inputs the answer into Caregiver UI 175 which sends the information to Storage 155. Rules-Based Logic 135 then sends the next diagnostic step to Caregiver UI 175 depending on the previous answer.

If the answer at 4108 is no, then the information will be sent to and recorded in Storage 155 and Rules-Based Logic 135 will send relevant information with explanations to Patient UI 183 along with the next diagnostic step to Caregiver UI 175 at 41:17, "Is prolactin 20?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI depending on the previous answer.

If the answer at 4110 is yes, then the information will be sent to and recorded in Storage 155 and Rules-Based Logic 135 will send relevant information with explanations to Patient UI 183 along with the next directive to Caregiver UI 175 at 4111, "Add levothyroxine 25 pg daily." The provider will instruct the patient as to this directive, prescribe the medication, and enter confirmation into Caregiver UI 175 which sends the information to Storage 155. Rules-Based Logic 135 will send the next directive to Caregiver UI 175 at 4116, "Recheck TSH in one week." The provider will instruct the patient as to this directive, order the blood test, enter the result in Caregiver UI 175 which sends the information to Storage 155. The Expert System 110 will process these data and Rules Based Logic 135 will send relevant information with explanations to Patient UI 183 and Storage 165. Rules-Based Logic 135 and Knowledge Graph 150 will assess the next diagnostic step at 4103, "Is TSH<0.6 mIU/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4110 is no, then the information will be sent to and recorded in Storage 155 and Rules-Based Logic 135 will send relevant information with explanations to Patient UI 183 along with the next diagnostic step to Caregiver UI 175 at 4112, "Is TSH>5 and 10 mIU/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4112 is yes, then the information will be sent to and recorded in Storage 155 and Rules-Based Logic 135 will send relevant information with explanations to Patient UI 183 along with the next directive to Caregiver UI 175 at 4113, "Add levothyroxine 50 μg daily." The provider will instruct the patient as to this directive, prescribe the medication, and enter confirmation into Caregiver UI 175 which sends the information to Storage 155. Rules-Based Logic 135 will send the next directive to Caregiver UI 175 at 4116, "Recheck TSH in one week." The provider will instruct the patient as to this directive, order the blood test, enter the result in Caregiver UI 175 which sends the information to Storage 155. The Expert System 110 will process these data and Rules Based Logic 135 will send relevant information with explanations to Patient UI 183 and Storage 165. Rules-Based Logic 135 and Knowledge Graph 150 will assess the next diagnostic step at 4103, "Is TSH<0.6 mIU/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4112 is no, then the information will be sent to and recorded in Storage 155 and Rules-Based Logic 135 will send relevant information with explanations to Patient UI 183 along with the next diagnostic step to Caregiver UI 175 at 4114, "Is TSH>10 mIU/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4114 is yes, then the information will be sent to and recorded in Storage 155 and Rules-Based Logic 135 will send relevant information with explanations to Patient UI 183 along with the next directive to Caregiver UI 175 at 4115, "Add levothyroxine 100 μg daily." The provider will instruct the patient as to this directive, prescribe the medication, and enter confirmation into Caregiver UI 175 which sends the information to Storage 155. Rules-Based Logic 135 will send the next directive to Caregiver UI 175 at 4116, "Recheck TSH in one week." The provider will instruct the patient as to this directive, order the blood test, enter the result in Caregiver UI 175 which sends the information to Storage 155. The Expert System 110 will process these data and Rules Based Logic 135 will send relevant information with explanations to Patient UI 183 and Storage 165. Rules-Based Logic 135 and Knowledge Graph 150 will assess the next diagnostic step at 4103, "Is TSH<0.6 mIU/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4114 is no, then the information will be sent to and recorded in Storage 155 and Rules-Based Logic 135 will send relevant information with explanations to Patient UI 183 along with the next diagnostic step to Caregiver UI 175 at 4117, "Is prolactin >20 ng/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4117 is yes, then the information will be sent to and recorded in Storage 155 and Rules-Based Logic 135 will send relevant information with explanations to Patient UI 183 along with the next diagnostic step to Caregiver UI 175 at 4118, "Is the patient currently on cabergoline?" The provider inputs the answer into Caregiver UI 175 which sends the information to Storage 155. Rules-Based Logic 135 then sends the next diagnostic step to Caregiver UI 175 depending on the previous answer.

If the answer at 4117 is no, then the information will be sent to and recorded in Storage 155 and Rules-Based Logic 135 will send relevant information with explanations to Patient UI 183 along with the next diagnostic step to Caregiver UI 175 at 4124, "Does the patient have galactorrhea?" The provider examines the patient and inputs the answer into Caregiver UI 175 which then sends the information to Storage 155. Rules-Based Logic 135 sends the next diagnostic step to Caregiver UI 175 depending on the previous answer.

If the answer at 4118 is yes, then the information will be sent to and recorded in Storage 155 and Rules-Based Logic 135 will send relevant information with explanations to Patient UI 183 along with the next directive to Caregiver UI 175 at 4119, "Increase cabergoline by 0.25 mg per dose and recheck prolactin each week until prolactin <20 ng/mL or to maximum of cabergoline 2 mg per week." The provider will instruct the patient as to this directive, prescribe the medication, and order the test in one week, inputs the test results into Caregiver UI 175 which sends the information to Storage 155. Rules-Based Logic 135 then sends the next diagnostic step to Caregiver UI 175 at 4120, "Is current cabergoline dose 2 mg weekly but prolactin still >20 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4118 is no, then the information will be sent to and recorded in Storage 155 and Rules-Based Logic 135 will send relevant information with explanations to Patient UI 183 along with the next diagnostic step to Caregiver UI 175 at 4125, "is prolactin ≥30 mg/L?" The provider inputs the answer into Caregiver UI 175 which sends the information to Storage 155. Rules-Based Logic 135 then sends the next directive or diagnostic step to Caregiver UI 175 depending on the previous answer.

If the answer at 4120 is yes, then the information will be sent to and recorded in Storage 155 and Rules-Based Logic 135 will send relevant information with explanations to Patient UI 183 along with the next diagnostic step to Caregiver UI 175 at 4121, "is a prolactinoma seen on CT or MRI?" The provider will instruct the patient as to this directive, order the imaging study, and inputs the test results into Caregiver UI 175 which sends the information to Storage 155. Rules-Based Logic 135 then sends the next directive to Caregiver UI 175 depending on the previous answer.

If the answer at 4120 is no, then the information will be sent to and recorded in Storage 155 and Rules-Based Logic 135 will send relevant information with explanations to Patient UI 183 along with the next diagnostic step to Caregiver UI 175 at 4133, "Is 17-OH Progesterone 5200 ng/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4121 is yes, then the information will be sent to and recorded in Storage 155 and Rules-Based Logic 135 will send relevant information with explanations to Patient UI 183 along with the next directive and hard stop to Caregiver UI 175 at 4123, "Refer to neurosurgery." The provider will instruct the patient as to this directive, makes the referral, and inputs confirmation of compliance to this directive in Caregiver UI 175 and Storage 155. Re-entry after treatment back onto the protocol will be at the beginning.

If the answer at 4121 is no, then the information will be sent to and recorded in Storage 155 and Rules-Based Logic 135 will send relevant information with explanations to Patient UI 183 along with the next directive and hard stop to Caregiver UI 175 at 4122, "Refer to endocrinologist." The provider will instruct the patient as to this directive, makes the referral, and inputs confirmation of compliance to this directive in Caregiver UI 175 and Storage 155. Re-entry after treatment back onto the protocol will be at the beginning.

If the answer at 4124 is yes, then the information will be sent to and recorded in Storage 155 and Rules-Based Logic 135 will send relevant information with explanations to Patient UI 183 along with the next diagnostic step to Caregiver UI 175 at 4118, "Is the patient currently on cabergoline?" The provider inputs the answer into Caregiver UI 175 which sends the information to Storage 155. Rules-Based Logic 135 then sends the next diagnostic step to Caregiver UI 175 depending on the previous answer.

If the answer at 4124 is no, then the information will be sent to and recorded in Storage 155 and Rules-Based Logic 135 will send relevant information with explanations to Patient UI 183 along with the next diagnostic step to Caregiver UI 175 at 4133, "Is 17-OH Progesterone ≥200 ng/mL?" The results are shared in Caregiver UI 175 and Patient UI 183. The provider inputs the answer into Caregiver UI 175 which sends the information to Storage 155. Rules-Based Logic 135 then sends the next diagnostic step to Caregiver UI 175 depending on the previous answer.

If the answer at 4125 is yes, then the information will be sent to and recorded in Storage 155 and Rules-Based Logic 135 will send relevant information with explanations to Patient UI 183 along with the next directive to Caregiver UI 175 at 4128, "Prescribe cabergoline 0.25 mg PO every Sunday and Wednesday."

The provider will instruct the patient as to this directive, prescribe the medication, and enter a confirmation in Caregiver UI 175. Rules-Based Logic 135 will send the next directive to Caregiver UI 175 at 4132, "Prolactin should be rechecked in 1 week." The provider will instruct the patient as to this directive, order the blood test, and enter the result in Caregiver UI 175. The Expert System 110 will process these data and Rules Based Logic 135 will send relevant information with explanations to Patient 183 along with the next diagnostic step to Caregiver UI 175 at 4117, "Is prolactin ≥20 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4125 is no, then the information will be sent to and recorded in Storage 155 and Rules-Based Logic 135 will send relevant information with explanations to Patient UI 183 along with the next diagnostic step to Caregiver UI 175 at 4126, "is patient currently on bromocriptine 1.25 mg PO qHS?"

The provider inputs the answer into Caregiver UI 175 which sends the information to Storage 155. Rules-Based Logic 135 then sends the next directive or diagnostic step to Caregiver UI 175 depending on the previous answer.

If the answer at 4126 is yes, then the information will be sent to and recorded in Storage 155 and Rules-Based Logic 135 will send relevant information with explanations to Patient UI 183 along with the next directive to Caregiver UI 175 at 4129, "Prescribe bromocriptine 2.5 mg PO qHS." The provider will prescribe the medication and instruct the patient as to this directive and then enter confirmation into Caregiver UI 175. Rules-Based Logic 135 will send the next directive to Caregiver UI 175 at 4132, "Prolactin should be rechecked in 1 week." The provider will instruct the patient as to this directive, order the blood test, and enter the result in Caregiver UI 175. The Expert System 110 will process these data and Rules Based Logic 135 will send relevant information with explanations to Patient UI 183 along with the next diagnostic step to Caregiver UI 175 at 4117, "Is prolactin ≥20 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4126 is no, then the information will be sent to and recorded in Storage 155 and Rules-Based Logic 135 will send relevant information with explanations to Patient UI 183 along with the next diagnostic step to Caregiver UI 175 at 4127, "is patient currently on bromocriptine 2.5 mg PO qHS?" The provider inputs the answer into Caregiver UI 175 which sends the information to Storage 155. Rules-Based Logic 135 then sends the next directive to Caregiver UI 175 depending on the previous answer.

If the answer at 4127 is yes, then the information will be sent to and recorded in Storage 155 and Rules-Based Logic 135 will send relevant information with explanations to Patient UI 183 along with the next directive to Caregiver UI 175 at 4130, "Stop bromocriptine." The provider will instruct the patient as to this directive and enter a confirmation in Caregiver UI 175. Rules-Based Logic 135 will send the next directive to Caregiver UI 175 at 4128, "Prescribe cabergoline 0.25 mg PO every Sunday and Wednesday." The provider will instruct the patient as to this directive, prescribe the medication, and enter a confirmation in Caregiver UI 175. Rules-Based Logic 135 will send the next directive to Caregiver UI 175 at 4132, "Prolactin should be rechecked in 1 week." The provider will instruct the patient as to this directive, order the blood test, and enter the result in Caregiver UI 175. The Expert System 110 will process these data and Rules Based Logic 135 will send relevant information with explanations to Patient UI 183 along with the next diagnostic step to Caregiver UI 175 at 4117, "Is prolactin 20 ng/mL?" The provider inputs the answer into Caregiver UI 175 which sends the information to Storage 155. Rules-Based Logic 135 then sends the next directive to Caregiver UI 175 depending on the previous answer.

If the answer at 4127 is no, then the information will be sent to and recorded in Storage 155 and Rules-Based Logic 135 will send relevant information with explanations to Patient UI 183 along with the next directive to Caregiver UI 175 at 4131, "Prescribe bromocriptine 1.25 mg PO qHS." The provider will instruct the patient as to this directive, prescribe the medication, and enter a confirmation in Caregiver UI 175. Rules-Based Logic 135 will send the next directive to Caregiver UI 175 at 4132, "Prolactin should be rechecked in 1 week." The provider will instruct the patient as to this directive, order the blood test, and enter the result in Caregiver UI 175. The Expert System 110 will process these data and Rules Based Logic 135 will send relevant information with explanations to Patient 183 along with the diagnostic step to Caregiver UI 175 at 4117, "is prolactin ≥20 ng/mL?" The provider inputs the answer into Caregiver UI 175 which sends the information to Storage 155. Rules-Based Logic 135 then sends the next directive to Caregiver UI 175 depending on the previous answer.

If the answer at 4133 is yes, then the information will be sent to and recorded in Storage 155 and Rules-Based Logic 135 will send relevant information with explanations to Patient UI 183 along with the next diagnostic step to Caregiver UI 175 at 4134, "Is DHEA-S>200 ng/ml?" The provider inputs the answer into Caregiver UI 175 which sends the information to Storage 155. Rules-Based Logic 135 then sends the next diagnostic step to Caregiver UI 175 depending on the previous answer.

If the answer at 4133 is no, then the information will be sent to and recorded in Storage 155 and Rules-Based Logic 135 will send relevant information with explanations to Patient UI 183 along with the next diagnostic step to Caregiver UI 175 at 4137, "Is DHEA-S>200 ng/ml?" The provider inputs the answer into Caregiver UI 175 which sends the information to Storage 155. Rules-Based Logic 135 then sends the next diagnostic step to Caregiver UI 175 depending on the previous answer.

If the answer at 4134 is yes, then the information will be sent to and recorded in Storage 155 and Rules-Based Logic 135 will send relevant information with explanations to Patient UI 183 along with the next diagnostic step to Caregiver UI 175 at 4135, "is the patient currently taking dexamethasone?" The provider inputs the answer into Caregiver UI 175 which sends the information to Storage 155. Rules-Based Logic 135 then sends the next directive or diagnostic step to Caregiver UI 175 depending on the previous answer.

If the answer at 4134 is no, then the information will be sent to and recorded in Storage 155 and Rules-Based Logic 135 will send relevant information with explanations to Patient UI 183 along with the next diagnostic step to Caregiver UI 175 at 4138, "is the patient currently taking dexamethasone?" The provider inputs the answer into Caregiver UI 175 which sends the information to Storage 155. Rules-Based Logic 135 then sends the next directive or directive or diagnostic step to Caregiver UI 175 depending on the previous answer.

If the answer at 4135 is yes, then the information will be sent to and recorded in Storage 155 and Rules-Based Logic 135 will send relevant information with explanations to Patient UI 183 along with the next diagnostic step to Caregiver UI 175 at 4138, "is the patient currently taking dexamethasone?" The provider inputs the answer into Caregiver UI 175 which sends the information to Storage 155. Rules-Based Logic 135 then sends the next diagnostic step to Caregiver UI 175 depending on the previous answer.

If the answer at 4135 is no, then the information will be sent to and recorded in Storage 155 and Rules-Based Logic 135 will send relevant information with explanations to Patient UI 183 along with the next directive to Caregiver UI 175 at 4136, "Rx dexamethasone 0.25 mg PO qHS." The provider will instruct the patient as to this directive, prescribe the medication, and then enter a confirmation in Caregiver UI 175. Rules-Based Logic 135 will send the next directive to Caregiver UI 175 at 4140, "Recheck 17-OH Progesterone and DHEA-S in 7 days." The provider will instruct the patient as to this directive, order the blood test, and enter the result in Caregiver UI 175. The Expert System 110 will process these data and Rules Based Logic 135 will send relevant information with explanations to Patient UI

183 along with the next diagnostic step to Caregiver UI 175 at 4133, "Is 17-OH Progesterone ≥200 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4137 is yes, then the information will be sent to and recorded in Storage 155 and Rules-Based Logic 135 will send relevant information with explanations to Patient UI 183 along with the next diagnostic step to Caregiver UI 175 at 4138, "is the patient currently taking dexamethasone?" The provider inputs the answer into Caregiver UI 175 which sends the information to Storage 155. Rules-Based Logic 135 then sends the next directive or diagnostic step to Caregiver UI 175 depending on the previous answer.

If the answer at 4137 is no, then the information will be sent to and recorded in Storage 155 and Rules-Based Logic 135 will send relevant information with explanations to Patient UI 183 along with the next diagnostic step to Caregiver UI 175 at 4142, "Is Hgb<8 gr/dL?" The provider inputs the answer into Caregiver UI 175 which sends the information to Storage 155. Rules-Based Logic 135 then sends the next diagnostic step to Caregiver UI 175 depending on the previous answer.

If the answer at 4138 is yes, then the information will be sent to and recorded in Storage 155 and Rules-Based Logic 135 will send relevant information with explanations to Patient UI 183 along with the next diagnostic step to Caregiver UI 175 at 4139, "Current dose of dexamethasone 0.25 mg PO qHS?" The provider inputs the answer into Caregiver UI 175 which sends the information to Storage 155. Rules-Based Logic 135 then sends the next diagnostic step to Caregiver UI 175 depending on the previous answer.

If the answer at 4138 is no, then the information will be sent to and recorded in Storage 155 and Rules-Based Logic 135 will send relevant information with explanations to Patient UI 183 along with the next directive to Caregiver UI 175 at 4136, "Rx dexamethasone 0.25 mg PO qHS." The provider will instruct the patient as to this directive, prescribe the medication, and enter a confirmation in Caregiver UI 175. Rules-Based Logic 135 will send the next directive to Caregiver UI 175 at 4140, "Recheck 17-OH Progesterone and DHEA-S in 7 days." The provider will instruct the patient as to this directive, order the blood test, and enter the result in Caregiver UI 175. The Expert System 110 will process these data and Rules Based Logic 135 will send relevant information with explanations to Patient UI 183 along with the next diagnostic step to Caregiver UI 175 at 4133, "Is 17-OH Progesterone ≥200 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4139 is yes, then the information will be sent to and recorded in Storage 155 and Rules-Based Logic 135 will send relevant information with explanations to Patient UI 183 along with the next directive to Caregiver UI 175 at 4141, "Increase dose of dexamethasone to 0.5 mg PO qHS." The provider will instruct the patient as to this directive, prescribe the medication, and enter a confirmation into Caregiver UI 175. Rules-Based Logic 135 will send the next diagnosis step to Caregiver UI 175 at 4142, "Is Hgb<8 gm/dL?" The provider inputs the answer into Caregiver UI 175 which sends the information to Storage 155. Rules-Based Logic 135 then sends the next diagnostic step to Caregiver UI depending on the previous answer.

If the answer at 4139 is no, then the information will be sent to and recorded in Storage 155 and Rules-Based Logic 135 will send relevant information with explanations to Patient UI 183 along with the next diagnostic step to Caregiver UI 175 at 4142, "Is Hgb<8 gm/dL?" The provider inputs the answer into Caregiver UI 175 which sends the information to Storage 155. Rules-Based Logic 135 then sends the next diagnostic step to Caregiver UI 175 depending on the previous answer.

If the answer at 4143 is yes, then the information will be sent to and recorded in Storage 155 and Rules-Based Logic 135 will send relevant information with explanations to Patient UI 183 along with the next directive and hard stop to Caregiver UI 175 at 4148, "Consult hematology." The provider informs the patient, makes the referral, and inputs confirmation of compliance to this directive in Caregiver UI 175 and Storage 155. Re-entry after treatment back onto the protocol will be at the beginning.

If the answer at 4143 is no, then the information will be sent to and recorded in Storage 155 and Rules-Based Logic 135 will send relevant information with explanations to Patient UI 183 along with the next directive to Caregiver UI 175 at 4144, "Prescribe prenatal vitamins and iron." The provider will instruct the patient as to this directive, prescribe the medication, and enter a confirmation in Caregiver UI 175. Rules-Based Logic 135 will send the next directive to Caregiver UI 175 at 4145, "Check CBC in 1 month." The provider will order the test and results will be entered into Caregiver UI 175. The Expert System 110 will process these data and Rules Based Logic 135 will send relevant information with explanations to Patient 183 along with the next diagnostic step to Caregiver UI 175 at 4142, "Is Hgb<8 gm/dL?" The provider inputs the answer into Caregiver UI 175 which sends the information to Storage 155. Rules-Based Logic 135 then sends the next diagnostic step to Caregiver UI 175 depending on the previous answer.

If the answer at 4146 is yes, then the information will be sent to and recorded in Storage 155 and Rules-Based Logic 135 will send relevant information with explanations to Patient UI 183 along with the next directive and hard stop to Caregiver UI 175 at 4148, "Consult hematology." The provider informs the patient, makes the referral, and inputs confirmation of compliance to this directive in Caregiver UI 175 and Storage 155. Re-entry after treatment back onto the protocol will be at the beginning.

If the answer at 4146 is no, then the information will be sent to and recorded in Storage 155 and Rules-Based Logic 135 will send relevant information with explanations to Patient UI 183 along with the next diagnostic step to Caregiver UI 175 at 4147, "Are platelets <150 k or >450 k?" The provider inputs the answer into Caregiver UI 175 which sends the information to Storage 155. Rules-Based Logic 135 then sends the next directive or diagnostic step to Caregiver UI 175 depending on the previous answer.

If the answer at 4147 is yes, then the information will be sent to and recorded in Storage 155 and Rules-Based Logic 135 will send relevant information with explanations to Patient UI 183 along with the next directive and hard stop to Caregiver UI 175 at 4148, "Consult hematology." The provider informs the patient, makes the referral, and inputs confirmation of compliance to this directive in Caregiver UI 175 and Storage 155. Re-entry after treatment back onto the protocol will be at 4150.

If the answer at 4147 is no, then the information will be sent to and recorded in Storage 155 and Rules-Based Logic 135 will send relevant information with explanations to Patient UI 183 along with the next diagnostic step to Caregiver UI 175 at 4149, "Is WBC <4 or >11?" The provider inputs the answer into Caregiver UI 175 which sends the information to Storage 155. Rules-Based Logic 135 then sends the next directive or diagnostic step to Caregiver UI 175 depending on the previous answer.

If the answer at 4149 is yes, then the information will be sent to and recorded in Storage 155 and Rules-Based Logic 135 will send relevant information with explanations to Patient UI 183 along with the next directive and hard stop to Caregiver UI 175 at 4148, "Consult hematology." The provider informs the patient, makes the referral, and inputs confirmation of compliance to this directive in Caregiver UI 175 and Storage 155. Re-entry after treatment back onto the protocol will be at 4150.

If the answer at 4149 is no, then the information will be sent to and recorded in Storage 155 and Rules-Based Logic 135 will send relevant information with explanations to Patient UI 183 along with the next diagnostic step to Caregiver UI 175 at 4150, "Are the electrolytes within normal limits?" The provider inputs the answer into Caregiver UI 175 which sends the information to Storage 155. Rules-Based Logic 135 then sends the next directive or diagnostic step to Caregiver UI 175 depending on the previous answer.

If the answer at 4150 is yes, then the information will be sent to and recorded in Storage 155 and Rules-Based Logic 135 will send relevant information with explanations to Patient UI 183 along with the next diagnostic step to Caregiver UI 175 at 4153, "is fasting glucose >126 mg/dL?" The provider inputs the answer into Caregiver UI 175 which sends the information to Storage 155. Rules-Based Logic 135 then sends the next diagnostic step to Caregiver UI 175 depending on the previous answer.

If the answer at 4150 is no, then the information will be sent to and recorded in Storage 155 and Rules-Based Logic 135 will send relevant information with explanations to Patient UI 183 along with the next directive to Caregiver UI 175 at 4151, "Correct electrolyte abnormalities." The provider will instruct the patient as to this directive, remedy the situation, and then enter a confirmation into Caregiver UI 175. Rules-Based Logic 135 will send the next directive to Caregiver UI 175 at 4152, "Recheck electrolytes in one week." The provider will instruct the patient as to this directive, order the blood test, and enter the results in Caregiver UI 175. The Expert System 110 will process these data and Rules Based Logic 135 will send relevant information with explanations to Patient UI 183 along with the diagnostic step to Caregiver UI 175 at 4150, "Are the electrolytes within normal limits?" The provider inputs the answer into Caregiver UI 175 which sends the information to Storage 155. Rules-Based Logic 135 then sends the next directive or diagnostic step to Caregiver UI 175 depending on the previous answer.

If the answer at 4153 is yes, then the information will be sent to and recorded in Storage 155 and Rules-Based Logic 135 will send relevant information with explanations to Patient UI 183 along with the next diagnostic step to Caregiver UI 175 at 4154, "is patient currently taking metformin 1,000 mg BID?" The provider inputs the answer into Caregiver UI 175 which sends the information to Storage 155. Rules-Based Logic 135 then sends the next directive to Caregiver UI 175 depending on the previous answer.

If the answer at 4153 is no, then the information will be sent to and recorded in Storage 155 and Rules-Based Logic 135 will send relevant information with explanations to Patient UI 183 along with the next diagnostic step to Caregiver UI 175 at 4156, "is fasting glucose ≥99 mg/dL & ≤126 mg/dL?" The provider inputs the answer into Caregiver UI 175 which sends the information to Storage 155. Rules-Based Logic 135 then sends the next directive or diagnostic step to Caregiver UI 175 depending on the previous answer.

If the answer at 4154 is yes, then the information will be sent to and recorded in Storage 155 and Rules-Based Logic 135 will send relevant information with explanations to Patient UI 183 along with the next directive to Caregiver UI 175 at 4155, "Prescribe insulin to control blood glucose until hemoglobin A1c is less than 6." The provider will instruct the patient as to this directive, remedy the situation, then input a confirmation in Caregiver UI 175. Rules-Based Logic 135 will send the next diagnostic step to Caregiver UI 175 at 4162, "Are $CO_2$, BUN, creatinine, albumin, calcium, bilirubin, AST, ALT, alkaline phosphatase within normal limits?" The provider inputs the answer into Caregiver UI 175 which sends the information to Storage 155. Rules-Based Logic 135 then sends the next directive or diagnostic step to Caregiver UI 175 depending on the previous answer.

If the answer at 4154 is no, then the information will be sent to and recorded in Storage 155 and Rules-Based Logic 135 will send relevant information with explanations to Patient UI 183 along with the next directive to Caregiver UI 175 at 4160, "Prescribe metformin 500 mg PO BID for 2 weeks, then 500 mg TID for 3 weeks, followed by 1000 mg BID thereafter." The provider will instruct the patient as to this directive, order the medication, and enter a confirmation into Caregiver UI 175. Rules-Based Logic 135 will send the next directive to Caregiver UI 175 at 4161, "Repeat fasting glucose and insulin 8 weeks after initiation of metformin." The provider will instruct the patient as to this directive, order the blood test, and enter the results in Caregiver UI 175. The Expert System 110 will process these data and Rules Based Logic 135 will send relevant information with explanations to Patient UI 183 along with the next diagnostic step to Caregiver UI 175 at 4153, "Is fasting glucose >126 mg/dL?" The provider inputs the answer into Caregiver UI 175 which sends the information to Storage 155. Rules-Based Logic 135 then sends the next diagnostic step to Caregiver UI 175 depending on the previous answer.

If the answer at 4156 is yes, then the information will be sent to and recorded in Storage 155 and Rules-Based Logic 135 will send relevant information with explanations to Patient UI 183 along with the next directive to Caregiver UI 175 at 4157, "Prediabetic: Diet and Exercise." The provider will instruct the patient as to this directive and then inputs the confirmation into Caregiver UI 175. Rules-Based Logic 135 will send the next diagnostic step to Caregiver UI 175 at 4158, "Is fasting insulin ≥10?" The provider inputs the answer into Caregiver UI 175 which sends the information to Storage 155. Rules-Based Logic 135 then sends the next diagnostic step to Caregiver UI 175 depending on the previous answer.

If the answer at 4156 is no, then the information will be sent to and recorded in Storage 155 and Rules-Based Logic 135 will send relevant information with explanations to Patient UI 183 along with the next diagnostic step to Caregiver UI 175 at 4158, "Is fasting insulin ≥10?" The provider inputs the answer into Caregiver UI 175 which sends the information to Storage 155. Rules-Based Logic 135 then sends the next diagnostic step to Caregiver UI 175 depending on the previous answer.

If the answer at 4158 is yes, then the information will be sent to and recorded in Storage 155 and Rules-Based Logic 135 will send relevant information with explanations to Patient UI 183 along with the next diagnostic step to Caregiver UI 175 at 4159, "is patient currently taking metformin 1000 mg BID?" The provider inputs the answer into Caregiver UI 175 which sends the information to Storage 155. Rules-Based Logic 135 then sends the next directive or diagnostic step to Caregiver UI 175 depending on the previous answer.

If the answer at 4158 is no, then the information will be sent to and recorded in Storage 155 and Rules-Based Logic 135 will send relevant information with explanations to Patient UI 183 along with the next diagnostic step to Caregiver UI 175 at 4162, "Are $CO_2$, BUN, creatinine, albumin, calcium, bilirubin, AST, ALT, alkaline phosphatase within normal limits?" The provider inputs the answer into Caregiver UI 175 which sends the information to Storage 155. Rules-Based Logic 135 then sends the next directive or diagnostic step to Caregiver UI 175 depending on the previous answer.

If the answer at 4159 is yes, then the information will be sent to and recorded in Storage 155 and Rules-Based Logic 135 will send relevant information with explanations to Patient UI 183 along with the next diagnostic step to Caregiver UI 175 at 4162, "Are $CO_2$, BUN, creatinine, albumin, calcium, bilirubin, AST, ALT, alkaline phosphatase within normal limits?" The provider inputs the answer into Caregiver UI 175 which sends the information to Storage 155. Rules-Based Logic 135 then sends the next directive or diagnostic step to Caregiver UI 175 depending on the previous answer.

If the answer at 4159 is no, then the information will be sent to and recorded in Storage 155 and Rules-Based Logic 135 will send relevant information with explanations to Patient UI 183 along with the next directive to Caregiver UI 175 at 4160, "Prescribe metformin 500 mg PO BID for 2 weeks, then 500 mg TID for 3 weeks, followed by 1000 mg BID thereafter." The provider will instruct the patient as to this directive, order the medication and enter a confirmation in Caregiver UI 175. Rules-Based Logic 135 will send the next directive to Caregiver UI 175 at 4161, "Repeat fasting glucose and insulin 8 weeks after initiation of metformin." The provider will instruct the patient as to this directive, order the blood tests, and enter the results in Caregiver UI 175. The Expert System 110 will process these data and Rules Based Logic 135 will send relevant information with explanations to Patient UI 183 along with the diagnostic step to Caregiver UI 175 at 4153, "Is fasting glucose >126 mg/dL?" The provider inputs the answer into Caregiver UI 175 which sends the information to Storage 155. Rules-Based Logic 135 then sends the next directive or diagnostic step to Caregiver UI 175 depending on the previous answer.

If the answer at 4162 is yes, then the information will be sent to and recorded in Storage 155 and Rules-Based Logic 135 will send relevant information with explanations to Patient UI 183 along with the next diagnostic step to Caregiver UI 175 at 4164, "Is FSH≥25 IU/L?" The provider inputs the answer into Caregiver UI 175 which sends the information to Storage 155. Rules-Based Logic 135 then sends the next directive or diagnostic step to Caregiver UI 175 depending on the previous answer.

If the answer at 4162 is no, then the information will be sent to and recorded in Storage 155 and Rules-Based Logic 135 will send relevant information with explanations to Patient UI 183 along with the next directive to Caregiver UI 175 at 4163, "Pause to resolve any abnormalities. Re-enter at 4164."

The provider will instruct the patient as to this directive, repeat the blood test, enter the results, and register a confirmation into Caregiver UI 175. Rules-Based Logic 135 will send the next directive to Caregiver UI 175 at 4164, "Is FSH≥25 IU/L?" The provider inputs the answer into Caregiver UI 175 which sends the information to Storage 155. Rules-Based Logic 135 then sends the next directive or diagnostic step to Caregiver UI 175 depending on the previous answer.

If the answer at 4164 is yes, then the information will be sent to and recorded in Storage 155 and Rules-Based Logic 135 will send relevant information with explanations to Patient UI 183 along with the next directive to Caregiver UI 175 at 4172, "No ovarian reserve; patient will need donor eggs and IVF. Refer to a specialist." The provider will instruct the patient as to this directive, enter confirmation into Caregiver UI 175. Rules-Based Logic 135 will come to a hard stop.

If the answer at 4164 is no, then the information will be sent to and recorded in Storage 155 and Rules-Based Logic 135 will send relevant information with explanations to Patient UI 183 along with the next diagnostic step to Caregiver UI 175 at 4165, "Is FSH≥12 & ≤25 mIU/mL?" The provider inputs the answer into Caregiver UI 175 which sends the information to Storage 155. Rules-Based Logic 135 then sends the next diagnostic step to Caregiver UI 175 depending on the previous answer.

If the answer at 4165 is yes, then the information will be sent to and recorded in Storage 155 and Rules-Based Logic 135 will send relevant information with explanations to Patient UI 183 along with the next diagnostic step to Caregiver UI 175 at 4171, "is this the third time in a row that FSH is >12 mIU/mL?" The provider inputs the answer into Caregiver UI 175 which sends the information to Storage 155. Rules-Based Logic 135 then sends the next directive to Caregiver UI 175 depending on the previous answer.

If the answer at 4165 is no, then the information will be sent to and recorded in Storage 155 and Rules-Based Logic 135 will send relevant information with explanations to Patient UI 183 along with the next diagnostic step to Caregiver UI 175 at 4166, "is patient's age >35 & estradiol >85 μg/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4166 is yes, then the information will be sent to and recorded in Storage 155 and Rules-Based Logic 135 will send relevant information with explanations to Patient UI 183 along with the next directive to Caregiver UI 175 at 4173, "Recheck Day 2 (or 3) FSH and estradiol." The provider will instruct the patient as to this directive, order the blood test, and enter a confirmation in Caregiver UI 175. Rules-Based Logic 135 will send the next directive to Caregiver UI 175 at 4164, "Is FSH≥25 IU/L?" The provider inputs the answer into Caregiver UI 175 which sends the information to Storage 155. Rules-Based Logic 135 then sends the next directive or diagnostic step to Caregiver UI 175 depending on the previous answer.

If the answer at 4166 is no, then the information will be sent to and recorded in Storage 155 and Rules-Based Logic 135 will send relevant information with explanations to Patient UI 183 along with the next diagnostic step to Caregiver UI 175 at 4167, "Is patient age <30?" The provider inputs the answer into Caregiver UI 175 which sends the information to Storage 155. Rules-Based Logic 135 then sends the next diagnostic step to Caregiver UI 175 depending on the previous answer.

If the answer at 4167 is yes, then the information will be sent to and recorded in Storage 155 and Rules-Based Logic

135 will send relevant information with explanations to Patient UI 183 along with the next diagnostic step to Caregiver UI 175 at 4168, "Has the patient had a hystero-salpingogram within the last year?" The provider inputs the answer into Caregiver UI 175 which sends the information to Storage 155. Rules-Based Logic 135 then sends the next diagnostic step to Caregiver UI 175 depending on the previous answer.

If the answer at 4167 is no, then the information will be sent to and recorded in Storage 155 and Rules-Based Logic 135 will send relevant information with explanations to Patient UI 183 along with the next diagnostic step to Caregiver UI 175 at 4174, "Is estradiol ≥20 & ≤85 ng/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4168 is yes, then the information will be sent to and recorded in Storage 155 and Rules-Based Logic 135 will send relevant information with explanations to Patient UI 183 along with the next diagnostic step to Caregiver UI 175 at 4169, "is there bilateral tubal patency?" The provider inputs the answer into Caregiver UI 175 which sends the information to Storage 155. Rules-Based Logic 135 then sends the next diagnostic step to Caregiver UI 175 depending on the previous answer.

If the answer at 4168 is no, then the information will be sent to and recorded in Storage 155 and Rules-Based Logic 135 will send relevant information with explanations to Patient UI 183 along with the next diagnostic step to Caregiver UI 175 at 4175, "Does the patient have a history of bilateral tubal ligation?" The provider inputs the answer into Caregiver UI 175 which sends the information to Storage 155. Rules-Based Logic 135 then sends the next directive or diagnostic step to Caregiver UI 175 depending on the previous answer.

If the answer at 4169 is yes, then the information will be sent to and recorded in Storage 155 and Rules-Based Logic 135 will send relevant information with explanations to Patient UI 183 along with the next diagnostic step to Caregiver UI 175 at 4183, "Was a uterine cavity abnormality seen on HSG?" The provider inputs the answer into Caregiver UI 175 which sends the information to Storage 155. Rules-Based Logic 135 then sends the next diagnostic step to Caregiver UI 175 depending on the previous answer.

If the answer at 4169 is no, then the information will be sent to and recorded in Storage 155 and Rules-Based Logic 135 will send relevant information with explanations to Patient UI 183 along with the next diagnostic step to Caregiver UI 175 at 4170, "Are there bilateral proximal tubal occlusions?" The provider inputs the answer into Caregiver UI 175 which sends the information to Storage 155. Rules-Based Logic 135 then sends the next diagnostic step to Caregiver UI 175 depending on the previous answer.

If the answer at 4170 is yes, then the information will be sent to and recorded in Storage 155 and Rules-Based Logic 135 will send relevant information with explanations to Patient UI 183 along with the next diagnostic step to Caregiver UI 175 at 4180," Was a tubal re-canalization or re-anastomosis recently performed?" The provider inputs the answer into Caregiver UI 175 which sends the information to Storage 155. Rules-Based Logic 135 then sends the next directive or diagnostic step to Caregiver UI 175 depending on the previous answer.

If the answer at 4170 is no, then the information will be sent to and recorded in Storage 155 and Rules-Based Logic 135 will send relevant information with explanations to Patient UI 183 along with the next diagnostic step to Caregiver UI 175 at 4183, "Was a uterine cavity abnormality seen on HSG?" The provider inputs the answer into Caregiver UI 175 which sends the information to Storage 155. Rules-Based Logic 135 then sends the next diagnostic step to Caregiver UI 175 depending on the previous answer.

If the answer at 4171 is yes, then the information will be sent to and recorded in Storage 155 and Rules-Based Logic 135 will send relevant information with explanations to Patient UI 183 along with the next directive to Caregiver UI 175 at 4172, "No ovarian reserve; patient will need donor eggs and IVF. Refer to a specialist." The provider will instruct the patient as to this directive, enter confirmation into Caregiver UI 175. Rules-Based Logic 135 will come to a hard stop.

If the answer at 4171 is no, then the information will be sent to and recorded in Storage 155 and Rules-Based Logic 135 will send relevant information with explanations to Patient UI 183 along with the next directive to Caregiver UI 175 at 4173, "Recheck Day 2 (or 3) FSH and estradiol." The provider will instruct the patient as to this directive, orders the blood test, enters the result, and registers a confirmation in Caregiver UI 175. Rules-Based Logic 135 will send the next diagnostic step to Caregiver UI 175 at 4164, "Is FSH≥25 IU/L?" The provider inputs the answer into Caregiver UI 175 which sends the information to Storage 155. Rules-Based Logic 135 then sends the next directive or diagnostic step to Caregiver UI 175 depending on the previous answer.

If the answer at 4174 is yes, then the information will be sent to and recorded in Storage 155 and Rules-Based Logic 135 will send relevant information with explanations to Patient UI 183 along with the next diagnostic step to Caregiver UI 175 at 4168, "Has the patient had a hysterosalpingogram within the last year?" The provider inputs the answer into Caregiver UI 175 which sends the information to Storage 155. Rules-Based Logic 135 then sends the next diagnostic step to Caregiver UI 175 depending on the previous answer.

If the answer at 4174 is no, then the information will be sent to and recorded in Storage 155 and Rules-Based Logic 135 will send relevant information with explanations to Patient UI 183 along with the next directive to Caregiver UI 175 at 4179, "Refer to a specialty clinic for complicated care." The provider will instruct the patient as to this directive, make the referral, and enter a confirmation into Caregiver UI 175. Rules-Based Logic 135 will come to a hard stop.

If the answer at 4175 is yes, then the information will be sent to and recorded in Storage 155 and Rules-Based Logic 135 will send relevant information with explanations to Patient UI 183 along with the next diagnostic step to Caregiver UI 175 at 4177, "is it possible for the patient to have a tubal re-anastomosis?" The provider inputs the answer into Caregiver UI 175 which sends the information to Storage 155. Rules-Based Logic 135 then sends the next directive or diagnostic step to Caregiver UI 175 depending on the previous answer.

If the answer at 4175 is no, then the information will be sent to and recorded in Storage 155 and Rules-Based Logic 135 will send relevant information with explanations to Patient UI 183 along with the next directive to Caregiver UI 175 at 4176, "Perform a hysterosalpingogram on 2nd, 3rd, or 4th day after end of menses." The provider will instruct the patient as to this directive, schedules the procedure, records the results, and then inputs a confirmation into Caregiver UI 175. Rules-Based Logic 135 will send the next diagnostic step to Caregiver UI 175 at 4169, "Is there bilateral tubal patency?" The provider inputs the answer into Caregiver UI 175 which sends the information to Storage 155. Rules-Based Logic 135 then sends the next diagnostic step to Caregiver UI 175 depending on the previous answer.

If the answer at 4177 is yes, then the information will be sent to and recorded in Storage 155 and Rules-Based Logic 135 will send relevant information with explanations to Patient UI 183 along with the next directive to Caregiver UI 175 at 4178, "Perform a Tubal re-anastomosis. Permit 6 weeks of healing before performing an HSG." The provider will instruct the patient as to this directive, schedule and perform the procedure, then enter a confirmation into Caregiver UI 175. Rules-Based Logic 135 will send the next directive to Caregiver UI 175 at 4176, "Perform a hysterosalpingogram on 2nd, 3rd, or 4th day after end of menses." The provider will schedule the procedure and results will be entered into Caregiver UI 175. The Expert System 110 will process these data and Rules Based Logic 135 will send relevant information with explanations to Patient UI 183 along with the diagnostic step to Caregiver UI at 4169, "is there bilateral tubal patency The provider inputs the answer into Caregiver UI 175 which sends the information to Storage 155. Rules-Based Logic 135 then sends the next diagnostic step to Caregiver UI 175 depending on the previous answer.

If the answer at 4177 is no, then the information will be sent to and recorded in Storage 155 and Rules-Based Logic 135 will send relevant information with explanations to Patient UI 183 along with the next directive to Caregiver UI 175 at 4179, "Refer to a specialty clinic for complicated care." The provider will instruct the patient as to this directive, make a referral, and enter a confirmation into Caregiver UI 175. Rules-Based Logic 135 will come to a hard stop.

If the answer at 4180 is yes, then the information will be sent to and recorded in Storage 155 and Rules-Based Logic 135 will send relevant information with explanations to Patient UI 183 along with the next diagnostic step to Caregiver UI 175 at 4182, "Was the tubal re-canalization successful?" The provider inputs the answer into Caregiver UI 175 which sends the information to Storage 155. Rules-Based Logic 135 then sends the next directive or diagnostic step to Caregiver UI 175 depending on the previous answer.

If the answer at 4180 is no, then the information will be sent to and recorded in Storage 155 and Rules-Based Logic 135 will send relevant information with explanations to Patient UI 183 along with the next directive to Caregiver UI 175 at 4181, "Perform a tubal re-canalization." The provider will instruct the patient as to this directive, schedules the procedure, records the results, and registers a confirmation in Caregiver UI 175. Rules-Based Logic 135 will send the next diagnostic step to Caregiver UI 175 at 4182, "Was the establishment of patency to at least one tube successful?" The provider inputs the answer into Caregiver UI 175 which sends the information to Storage 155. Rules-Based Logic 135 then sends the next directive or diagnostic step to Caregiver UI 175 depending on the previous answer.

If the answer at 4182 is yes, then the information will be sent to and recorded in Storage 155 and Rules-Based Logic 135 will send relevant information with explanations to Patient UI 183 along with the next diagnostic step to Caregiver UI 175 at 4183, "Was a uterine cavity abnormality seen on HSG?" The provider inputs the answer into Caregiver UI 175 which sends the information to Storage 155. Rules-Based Logic 135 then sends the next diagnostic step to Caregiver UI 175 depending on the previous answer.

If the answer at 4182 is no, then the information will be sent to and recorded in Storage 155 and Rules-Based Logic 135 will send relevant information with explanations to Patient UI 183 along with the next directive to Caregiver UI 175 at 4179, "Refer to a specialty clinic for complicated care." The provider will instruct the patient as to this directive, make a referral, and enter s confirmation in Caregiver UI 175. Rules-Based Logic 135 will come to a hard stop.

If the answer at 4183 is yes, then the information will be sent to and recorded in Storage 155 and Rules-Based Logic 135 will send relevant information with explanations to Patient UI 183 along with the next diagnostic step to Caregiver UI 175 at 4190, "Has the patient undergone surgery to correct the uterine cavity abnormality in the last year?" The provider inputs the answer into Caregiver UI 175 which sends the information to Storage 155. Rules-Based Logic 135 then sends the next directive or diagnostic step to Caregiver UI 175 depending on the previous answer.

If the answer at 4183 is no, then the information will be sent to and recorded in Storage 155 and Rules-Based Logic 135 will send relevant information with explanations to Patient UI 183 along with the next diagnostic step to Caregiver UI 175 at 4184, "Does the patient experience pelvic pain?" The provider inputs the answer into Caregiver UI 175 which sends the information to Storage 155. Rules-Based Logic 135 then sends the next diagnostic step to Caregiver UI 175 depending on the previous answer.

If the answer at 4184 is yes, then the information will be sent to and recorded in Storage 155 and Rules-Based Logic 135 will send relevant information with explanations to Patient UI 183 along with the next diagnostic step to Caregiver UI 175 at 4185, "Has the patient undergone laparoscopy in the last year?" The provider inputs the answer into Caregiver UI 175 which sends the information to Storage 155. Rules-Based Logic 135 then sends the next directive or diagnostic step to Caregiver UI 175 depending on the previous answer.

If the answer at 4184 is no, then the information will be sent to and recorded in Storage 155 and Rules-Based Logic 135 will send relevant information with explanations to Patient UI 183 along with the next directive to Caregiver UI 175 at 4189, "Perform an operative hysteroscopy" The provider will instruct the patient as to this directive, schedule the surgery, and then enter confirmation into Caregiver UI 175. Rules-Based Logic 135 will send the next directive to Caregiver UI 175 at 4186, "Appropriate surgery (fulguration of endometriosis, neo salpingostomy, myomectomy, lysis of adhesions, polypectomy, and/or resection of septum) including an intraoperative chromotubation." The provider will perform the procedure and enter the resulting data into Caregiver UI 175. The Expert System 110 will process these data and Rules Based Logic 135 will send relevant information with explanations to Patient 183 along with the diagnostic step to Caregiver UI 175 at 4187, "Has the patient had baseline blood tests drawn within the last year?" The provider inputs the answer into Caregiver UI 175 which sends the information to Storage 155. Rules-Based Logic 135 then sends the next directive to Caregiver UI 175 depending on the previous answer.

If the answer at 4185 is yes, then the information will be sent to and recorded in Storage 155 and Rules-Based Logic 135 will send relevant information with explanations to Patient UI 183 along with the next diagnostic step to Caregiver UI 175 at 4187, "Has the patient had baseline blood tests drawn within the last year?" The provider inputs the answer into Caregiver UI 175 which sends the information to Storage 155. Rules-Based Logic 135 then sends the next directive or diagnostic step to Caregiver UI depending on the previous answer.

If the answer at 4185 is no, then the information will be sent to and recorded in Storage 155 and Rules-Based Logic 135 will send relevant information with explanations to Patient UI 183 along with the next directive to Caregiver UI 175 at 4186, "Appropriate surgery (fulguration of endometriosis, neo salpingostomy, myomectomy, lysis of adhesions, polypectomy, and/or resection of septum) including an intraoperative chromotubation." The provider will instruct the patient as to this directive, schedule the procedure, and then registers a confirmation in Caregiver UI 175. Rules-Based Logic 135 will send the next diagnostic step to Caregiver UI 175 at 4187, "Has the patient had baseline blood tests drawn within the last year?" The provider inputs the answer into Caregiver UI 175 which sends the information to Storage 155. Rules-Based Logic 135 then sends the next directive or diagnostic step to Caregiver UI 175 depending on the previous answer.

If the answer at 4187 is yes, then the information will be sent to and recorded in Storage 155 and Rules-Based Logic 135 will send relevant information with explanations to Patient UI 183 along with the next directive to Caregiver UI 175 at 4188, "Resume diagnosis and treatment pathway 8 weeks post-operatively." The provider will instruct the patient as to this directive and input a confirmation in Caregiver UI 175. Rules-Based Logic 135 will send the next diagnostic step to Caregiver UI 175 at 4103, "Is TSH<0.6 mIU/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4187 is no, then the information will be sent to and recorded in Storage 155 and Rules-Based Logic 135 will send relevant information with explanations to Patient UI 183 along with the next directive to Caregiver UI 175 at 4102, "Baseline blood tests are to be drawn in the morning and before eating breakfast: TSH, prolactin, DHEA-S, 17-OH progesterone, CBC, CMP, and insulin. Also add this cycle's Day 2 (or 3) estradiol and FSH. (Bring on a withdrawal bleed using Provera 10 mg for 10 days, if necessary.)" The provider will instruct the patient as to this directive, order the blood tests, enter the results, and then register a confirmation in Caregiver UI 175. Rules-Based Logic 135 will send the next diagnostic step to Caregiver UI 175 at 4192, "Are menstrual cycles between 21 and 38 days apart (start of one heavy flow to start of next heavy flow) but consistently same number of days+/−1 day?" The provider inputs the answer into Caregiver UI 175 which sends the information to Storage 155. Rules-Based Logic 135 then sends the next directive or diagnostic step to Caregiver UI 175 depending on the previous answer.

If the answer at 4190 is yes, then the information will be sent to and recorded in Storage 155 and Rules-Based Logic 135 will send relevant information with explanations to Patient UI 183 along with the next directive to Caregiver UI 175 at 4191, "Refer to specialist for IVF using a Gestational Carrier" The provider will instruct the patient as to this directive, make a referral, enter a confirmation into Caregiver UI 175. Rules-Based Logic 135 will come to a hard stop.

If the answer at 4190 is no, then the information will be sent to and recorded in Storage 155 and Rules-Based Logic 135 will send relevant information with explanations to Patient UI 183 along with the next diagnostic step to Caregiver UI 175 at 4184, "Does the patient experience pelvic pain?" The provider inputs the answer into Caregiver UI 175 which sends the information to Storage 155. Rules-Based Logic 135 then sends the next directive or diagnostic step to Caregiver UI 175 depending on the previous answer.

If the answer at 4192 is yes, then the information will be sent to and recorded in Storage 155 and Rules-Based Logic 135 will send relevant information with explanations to Patient UI 183 along with the next directive to Caregiver UI 175 at 4193, "Use ovulation prediction kit, check for 6 days starting [average cycle length minus 16 days]." The provider will instruct the patient as to this directive, and then input a confirmation into Caregiver UI 175. Rules-Based Logic 135 will send the next diagnostic step to Caregiver UI 175 at 4194, "Was there a robust LH surge?" The provider inputs the answer into Caregiver UI 175 which sends the information to Storage 155. Rules-Based Logic 135 then sends the next directive or diagnostic step to Caregiver UI 175 depending on the previous answer.

If the answer at 4192 is no, then the information will be sent to and recorded in Storage 155 and Rules-Based Logic 135 will send relevant information with explanations to Patient UI 183 along with the next diagnostic step to Caregiver UI 175 at 4236, "Is BMI<20?" The provider inputs the answer into Caregiver UI 175 which sends the information to Storage 155. Rules-Based Logic 135 then sends the next directive to Caregiver UI 175 depending on the previous answer.

If the answer at 4194 is yes, then the information will be sent to and recorded in Storage 155 and Rules-Based Logic 135 will send relevant information with explanations to Patient UI 183 along with the next diagnostic step to Caregiver UI 175 at 4195, "Does the male have more than 4 million motile normal morphology sperm?" The provider inputs the answer into Caregiver UI 175 which sends the information to Storage 155. Rules-Based Logic 135 then sends the next directive to Caregiver UI 175 depending on the previous answer.

If the answer at 4194 is no, then the information will be sent to and recorded in Storage 155 and Rules-Based Logic 135 will send relevant information with explanations to Patient UI 183 along with the next directive to Caregiver UI 175 at 4218, "Draw estradiol and progesterone" The provider will instruct the patient as to this directive, order the blood tests, enter the results, and register a confirmation in Caregiver UI 175. Rules-Based Logic 135 will send the next diagnostic step to Caregiver UI 175 at 4219, "is progesterone>2 ng/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4195 is yes, then the information will be sent to and recorded in Storage 155 and Rules-Based Logic 135 will send relevant information with explanations to Patient UI 183 along with the next directive to Caregiver UI 175 at 4196, "Timed intercourse day of positive surge and following day." The provider will instruct the patient as to this directive, and then enter a confirmation in Caregiver UI 175. Rules-Based Logic 135 will send the next directive to Caregiver UI 175 at 4197, "Check estradiol and progesterone levels one week later." The provider will instruct the patient as to this directive, order the blood tests, and enter the results in Caregiver UI 175. The Expert System 110 will process these data and Rules Based Logic 135 will send relevant information with explanations to Patient UI 183 along with the diagnostic step to Caregiver UI 175 at 4198, "is progesterone >15 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4195 is no, then the information will be sent to and recorded in Storage 155 and Rules-Based Logic 135 will send relevant information with explanations to Patient UI 183 along with the next directive to Caregiver UI 175 at 4225, "Intra Uterine Insemination the day after positive surge (or hCG trigger injection)" The provider will instruct the patient as to this directive, perform the procedure, and then enter a confirmation in Caregiver UI 175. Rules-Based Logic 135 will send the next directive to Caregiver UI 175 at 4197, "Check estradiol and progesterone levels one week later." The provider will instruct the patient as to the directive, order the blood tests, and enter the results in Caregiver UI 175. The Expert System 110 will process these data and Rules Based Logic 135 will send relevant information with explanations to Patient UI 183 along with the diagnostic step to Caregiver UI 175 at 4198, "is progesterone >15 ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4198 is yes, then the information will be sent to and recorded in Storage 155 and Rules-Based Logic 135 will send relevant information with explanations to Patient UI 183 along with the next diagnostic step to Caregiver UI 175 at 4199, "Patient currently prescribed estradiol 2 mg BID?" The provider inputs the answer into Caregiver UI 175 which sends the information to Storage 155. Rules-Based Logic 135 then sends the next diagnostic step to Caregiver UI 175 depending on the previous answer.

If the answer at 4198 is no, then the information will be sent to and recorded in Storage 155 and Rules-Based Logic 135 will send relevant information with explanations to Patient UI 183 along with the next diagnostic step to Caregiver UI 175 at 4207, "Is the patient currently taking progesterone supplements?" The provider inputs the answer into Caregiver UI 175 which sends the information to Storage 155. Rules-Based Logic 135 then sends the next diagnostic step to Caregiver UI 175 depending on the previous answer.

If the answer at 4199 is yes, then the information will be sent to and recorded in Storage 155 and Rules-Based Logic 135 will send relevant information with explanations to Patient UI 183 along with the next diagnostic step to Caregiver UI 175 at 4202, "Onset of menses less than 14 days following LH surge or hCG injection?" The provider inputs the answer into Caregiver UI 175 which sends the information to Storage 155. Rules-Based Logic 135 then sends the next directive or diagnostic step to Caregiver UI 175 depending on the previous answer.

If the answer at 4199 is no, then the information will be sent to and recorded in Storage 155 and Rules-Based Logic 135 will send relevant information with explanations to Patient UI 183 along with the next diagnostic step to Caregiver UI 175 at 4200, "is estradiol >150 μg/mL? The provider inputs the answer into Caregiver UI 175 which sends the information to Storage 155. Rules-Based Logic 135 then sends the next directive or diagnostic step to Caregiver UI 175 depending on the previous If the answer at 4200 is yes, then the information will be sent to and recorded in Storage 155 and Rules-Based Logic 135 will send relevant information with explanations to Patient UI 183 along with the next diagnostic step to Caregiver UI 175 at 4202, "Onset of menses less than 14 days following LH surge or hCG injection?" The provider inputs the answer into Caregiver UI 175 which sends the information to Storage 155. Rules-Based Logic 135 then sends the next directive or diagnostic step to Caregiver UI 175 depending on the previous answer.

If the answer at 4200 is no, then the information will be sent to and recorded in Storage 155 and Rules-Based Logic 135 will send relevant information with explanations to Patient UI 183 along with the next directive to Caregiver UI 175 at 4201 "Prescribe oral micronized estradiol 2 mg PO BID now (and in future cycles beginning 2nd day after the LH surge or hCG trigger injection)." The provider will instruct the patient as to this directive, prescribe the medication, and input a confirmation in Caregiver UI 175. Rules-Based Logic 135 will send the next diagnostic step to Caregiver UI 175 at 4202, "Onset of menses less than 14 days following LH surge or hCG injection?" The provider inputs the answer into Caregiver UI 175 which sends the information to Storage 155. Rules-Based Logic 135 then sends the next directive or diagnostic step to Caregiver UI 175 depending on the previous answer.

If the answer at 4202 is yes, then the information will be sent to and recorded in Storage 155 and Rules-Based Logic 135 will send relevant information with explanations to Patient UI 183 along with the next diagnostic step to Caregiver UI 175 at 4203, "Patient previously prescribed oral micronized progesterone 200 mg PO TID?" The provider inputs the answer into Caregiver UI 175 which sends the information to Storage 155. Rules-Based Logic 135 then sends the next directive to Caregiver UI 175 depending on the previous answer.

If the answer at 4202 is no, then the information will be sent to and recorded in Storage 155 and Rules-Based Logic 135 will send relevant information with explanations to Patient UI 183 along with the next directive to Caregiver UI 175 at 4204, "Check hCG level 2 weeks post LH surge." The provider will instruct the patient as to this directive, order the blood test, enter the result, and register a confirmation into Caregiver UI 175. Rules-Based Logic 135 will send the next diagnostic step to Caregiver UI 175 at 4205, "is hCG>5.0 IU/L?" The provider inputs the answer into Caregiver UI 175 which sends the information to Storage 155. Rules-Based Logic 135 then sends the next directive to Caregiver UI 175 depending on the previous answer.

If the answer at 4203 is yes, then the information will be sent to and recorded in Storage 155 and Rules-Based Logic 135 will send relevant information with explanations to Patient UI 183 along with the next directive to Caregiver UI 175 at 4204, "Check hCG level 2 weeks post LH surge." The provider will instruct the patient as to this directive, order the blood test, enter the result, and register a confirmation in Caregiver UI 175. Rules-Based Logic 135 will send the next diagnostic step to Caregiver UI 175 at 4205, "Is hCG>5.0 IU/L?" The provider inputs the answer into Caregiver UI 175 which sends the information to Storage 155. Rules-Based Logic 135 then sends the next directive to Caregiver UI 175 depending on the previous answer If the answer at 4203 is no, then the information will be sent to and recorded in Storage 155 and Rules-Based Logic 135 will send relevant information with explanations to Patient UI 183 along with the next directive to Caregiver UI 175 at 4206, "Prescribe oral micronized progesterone 200 mg PO TID, beginning 2 days after LH surge or hCG trigger injection" The provider will instruct the patient as to this directive, prescribe the medication, and then enter a confirmation in Caregiver UI 175. Rules-Based Logic 135 will send the next directive to Caregiver UI 175 at 4226, "if currently taken, stop estradiol and/or progesterone supplements" The provider will instruct the patient as to the directive, and enter the confirmation into Caregiver UI 175. Rules Based Logic 135 will send relevant information with explanations to Patient UI 183 along with the diagnostic step to Caregiver UI 175 at 4227, "Has the patient already taken letrozole?" The provider inputs the answer into Caregiver UI 175 which sends the information to Storage 155. Rules-Based Logic 135 then sends the next directive or diagnostic step to Caregiver UI 175 depending on the previous answer.

If the answer at 4205 is yes, then the information will be sent to and recorded in Storage 155 and Rules-Based Logic 135 will send relevant information with explanations to Patient UI 183 along with the next directive to Caregiver UI 175 at 4055, "Repeat hCG, estradiol, and progesterone levels 48 hours after most recent positive pregnancy test." The provider will instruct the patient as to this directive, order the blood tests, enter the results, and register a confirmation in Caregiver UI 175. Rules-Based Logic 135 will send the next diagnostic step to Caregiver UI 175 at 4057, "Was the increase in hCG <65%?" The provider inputs the answer into Caregiver UI 175 which sends the information to Storage 155. Rules-Based Logic 135 then sends the next directive or diagnostic step to Caregiver UI 175 depending on the previous answer.

If the answer at 4205 is no, then the information will be sent to and recorded in Storage 155 and Rules-Based Logic 135 will send relevant information with explanations to Patient UI 183 along with the next directive to Caregiver UI 175 at 4226 "if currently taken, stop estradiol and/or progesterone supplements." The provider will instruct the patient as to this directive and input a confirmation in Caregiver UI 175. Rules-Based Logic 135 will send the next diagnostic step to Caregiver UI 175 at 4227, "Has the patient previously taken letrozole?" The provider inputs the answer into Caregiver UI 175 which sends the information to Storage 155. Rules-Based Logic 135 then sends the next directive or diagnostic step to Caregiver UI 175 depending on the previous answer.

If the answer at 4207 is yes, then the information will be sent to and recorded in Storage 155 and Rules-Based Logic 135 will send relevant information with explanations to Patient UI 183 along with the next diagnostic step to Caregiver UI 175 at 4208, "Patient currently prescribed progesterone-in-oil (50 mg/mL) 100 mg IM daily?" The provider inputs the answer into Caregiver UI 175 which sends the information to Storage 155. Rules-Based Logic 135 then sends the next directive or diagnostic step to Caregiver UI 175 depending on the previous answer.

If the answer at 4207 is no, then the information will be sent to and recorded in Storage 155 and Rules-Based Logic 135 will send relevant information with explanations to Patient UI 183 along with the next diagnostic step to Caregiver UI 175 at 4213, "is progesterone ≥12 and ≤15 ng/mL?" The provider inputs the answer into Caregiver UI 175 which sends the information to Storage 155. Rules-Based Logic then sends the next diagnostic step to Caregiver UI 175 depending on the previous answer.

If the answer at 4208 is yes, then the information will be sent to and recorded in Storage 155 and Rules-Based Logic 135 will send relevant information with explanations to Patient UI 183 along with the next directive to Caregiver UI 175 at 4210, "Prescribe progesterone in oil (50 mg/mL) 100 mg IM dose daily, starting now and in future cycles beginning 2nd day after the LH surge or hCG trigger injection," The provider will instruct the patient as to this directive, prescribe the medication, and input a confirmation in Caregiver UI 175. Rules-Based Logic 135 will send the next diagnostic step to Caregiver UI 175 at 4199, "Patient currently prescribed estradiol 2 mg BID?" The provider inputs the answer into Caregiver UI 175 which sends the information to Storage 155. Rules-Based Logic 135 then sends the next directive or diagnostic step to Caregiver UI 175 depending on the previous answer.

If the answer at 4208 is no, then the information will be sent to and recorded in Storage 155 and Rules-Based Logic 135 will send relevant information with explanations to Patient UI 183 along with the next diagnostic step to Caregiver UI 175 at 4209, "Patient currently prescribed oral micronized progesterone 200 mg PO TID?" The provider inputs the answer into Caregiver UI 175 which sends the information to Storage 155. Rules-Based Logic 135 then sends the next directive or diagnostic step to Caregiver UI 175 depending on the previous answer.

If the answer at 4209 is yes, then the information will be sent to and recorded in Storage 155 and Rules-Based Logic 135 will send relevant information with explanations to Patient UI 183 along with the next directive to Caregiver UI 175 at 4210, "Prescribe progesterone in oil (50 mg/mL) 100 mg IM dose daily, starting now and in future cycles beginning 2nd day after the LH surge or hCG trigger injection." The provider will instruct the patient as to this directive, prescribe the medication, and input a confirmation in Caregiver UI 175. Rules-Based Logic 135 will send the next diagnostic step to Caregiver UI 175 at 4199, "Patient currently prescribed estradiol 2 mg BID?" The provider inputs the answer into Caregiver UI 175 which sends the information to Storage 155. Rules-Based Logic 135 then sends the next diagnostic step to Caregiver UI 175 depending on the previous answer.

If the answer at 4209 is no, then the information will be sent to and recorded in Storage 155 and Rules-Based Logic 135 will send relevant information with explanations to Patient UI 183 along with the next diagnostic step to Caregiver UI 175 at 4211, "Was the patient currently prescribed oral micronized progesterone 200 mg PO BID?" The provider inputs the answer into Caregiver UI 175 which sends the information to Storage 155. Rules-Based Logic 135 then sends the next diagnostic step to Caregiver UI 175 depending on the previous answer.

If the answer at 4211 is yes, then the information will be sent to and recorded in Storage 155 and Rules-Based Logic 135 will send relevant information with explanations to Patient UI 183 along with the next directive to Caregiver UI 175 at 4206, "Prescribe oral micronized progesterone 200 mg PO TID, beginning 2 days after LH surge or hCG trigger injection" The provider will instruct the patient as to this directive, prescribe the medication, and then enter confirmation into Caregiver UI 175. Rules-Based Logic 135 will send the next directive to Caregiver UI 175 at 4226, "If currently taken, stop estradiol and/or progesterone supplements" The provider will instruct the patient as to the directive, and enter the confirmation into Caregiver UI 175. Rules Based Logic 135 will send relevant information with explanations to Patient UI 183 along with the diagnostic step to Caregiver UI 175 at 4227, "Has the patient already taken letrozole?" The provider inputs the answer into Caregiver UI 175 which sends the information to Storage 155. Rules-Based Logic 135 then sends the next directive or diagnostic step to Caregiver UI 175 depending on the previous answer.

If the answer at 4211 is no, then the information will be sent to and recorded in Storage 155 and Rules-Based Logic 135 will send relevant information with explanations to Patient UI 183 along with the next directive to Caregiver UI 175 at 4212, "Prescribe oral micronized progesterone 200 mg PO BID starting today and in future cycles beginning 2nd day after the LH surge or hCG trigger injection" The provider will instruct the patient as to this directive, prescribes the medication, and then inputs the confirmation into Caregiver UI 175. Rules-Based Logic 135 will send the next diagnostic step to Caregiver UI 175 at 4199, "Patient currently prescribed estradiol 2 mg BID?" The provider inputs the answer into Caregiver UI 175 which sends the information to Storage 155. Rules-Based Logic 135 then sends the next diagnostic step to Caregiver UI 175 depending on the previous answer.

If the answer at 4213 is yes, then the information will be sent to and recorded in Storage 155 and Rules-Based Logic 135 will send relevant information with explanations to Patient UI 183 along with the next directive to Caregiver UI 175 at 4214, "Prescribe oral micronized progesterone 200 mg PO qHS, starting today and in future cycles beginning 2nd day after the LH surge or hCG trigger injection" The provider will instruct the patient as to this directive, prescribe the medication, and input a confirmation in Caregiver UI 175. Rules-Based Logic 135 will send the next diagnostic step to Caregiver UI 175 at 4199, "Patient currently prescribed estradiol 2 mg BID?" The provider inputs the answer into Caregiver UI 175 which sends the information to Storage 155. Rules-Based Logic 135 then sends the next diagnostic step to Caregiver UI 175 depending on the previous answer.

If the answer at 4213 is no, then the information will be sent to and recorded in Storage 155 and Rules-Based Logic 135 will send relevant information with explanations to Patient UI 183 along with the next diagnostic step to Caregiver UI 175 at 4215, "is progesterone $\geq 8$ and $\leq 11$ ng/mL?" The provider inputs the answer into Caregiver UI 175 which sends the information to Storage 155. Rules-Based Logic 135 then sends the next diagnostic step to Caregiver UI 175 depending on the previous answer.

If the answer at 4215 is yes, then the information will be sent to and recorded in Storage 155 and Rules-Based Logic 135 will send relevant information with explanations to Patient UI 183 along with the next directive to Caregiver UI 175 at 4216, "Prescribe oral micronized progesterone 200 mg PO BID starting today and in future cycles beginning 2nd day after the LH surge or hCG trigger injection" The provider will instruct the patient as to this directive, prescribe the medication, and input a confirmation in Caregiver UI 175. Rules-Based Logic 135 will send the next diagnostic step to Caregiver UI 175 at 4199, "Patient currently prescribed estradiol 2 mg BID?" The provider inputs the answer into Caregiver UI 175 which sends the information to Storage 155. Rules-Based Logic 135 then sends the next diagnostic step to Caregiver UI 175 depending on the previous answer.

If the answer at 4215 is no, then the information will be sent to and recorded in Storage 155 and Rules-Based Logic 135 will send relevant information with explanations to Patient UI 183 along with the next directive to Caregiver UI 175 at 4217, "Prescribe oral micronized progesterone 200 mg TID starting now and in future cycles beginning 2nd day after the LH surge or hCG trigger injection" The provider will instruct the patient as to this directive, prescribe the medication, and input a confirmation in Caregiver UI 175. Rules-Based Logic 135 will send the next diagnostic step to Caregiver UI 175 at 4199, "Patient currently prescribed estradiol 2 mg BID?" The provider inputs the answer into Caregiver UI 175 which sends the information to Storage 155. Rules-Based Logic 135 then sends the next diagnostic step to Caregiver UI 175 depending on the previous answer.

If the answer at 4219 is yes, then the information will be sent to and recorded in Storage 155 and Rules-Based Logic 135 will send relevant information with explanations to Patient UI 183 along with the next directive to Caregiver UI 175 at 4220, "Educate patient as to proper use of the ovulation kit." The provider will instruct the patient as to this directive, and then enter confirmation into Caregiver UI 175. Rules-Based Logic 135 will send the next diagnostic step to Caregiver UI 175 at 4227, "Has the patient already taken letrozole?" The provider inputs the answer into Caregiver UI 175 which sends the information to Storage 155. Rules-Based Logic 135 then sends the next directive or diagnostic step to Caregiver UI 175 depending on the previous answer.

If the answer at 4219 is no, then the information will be sent to and recorded in Storage 155 and Rules-Based Logic 135 will send relevant information with explanations to Patient UI 183 along with the next diagnostic step to Caregiver UI 175 at 4221, "is estradiol >150 pg/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4221 is yes, then the information will be sent to and recorded in Storage 155 and Rules-Based Logic 135 will send relevant information with explanations to Patient UI 183 along with the next directive to Caregiver UI 175 at 4222, "Pelvic ultrasound to measure the dominant ovarian follicle." The provider will instruct the patient as to this directive, order the image study, input findings, and register a confirmation in Caregiver UI 175. Rules-Based Logic 135 will send the next diagnostic step to Caregiver UI 175 at 4223, "is the dominant follicle ≥17 mm?" The provider inputs the answer into Caregiver UI 175 which sends the information to Storage 155. Rules-Based Logic 135 then sends the next directive or diagnostic step to Caregiver UI 175 depending on the previous answer.

If the answer at 4221 is no, then the information will be sent to and recorded in Storage 155 and Rules-Based Logic 135 will send relevant information with explanations to Patient UI 183 along with the next diagnostic step to Caregiver UI 175 at 4227, "Has the patient already taken letrozole?" The provider inputs the answer into Caregiver UI 175 which sends the information to Storage 155. Rules-Based Logic 135 then sends the next directive or diagnostic step to Caregiver UI 175 depending on the previous answer.

If the answer at 4223 is yes, then the information will be sent to and recorded in Storage 155 and Rules-Based Logic 135 will send relevant information with explanations to Patient UI 183 along with the next directive to Caregiver UI 175 at 4224, "Prescribe hCG 10,000 IU IM to trigger ovulation" The provider will instruct the patient as to this directive, prescribe and administer the medication, and then enter a confirmation in Caregiver UI 175. Rules-Based Logic 135 will send the next directive to Caregiver UI 175 at 4225, "Intra Uterine Insemination the day after positive surge (or hCG trigger injection)" The provider will instruct the patient as to the directive, perform the procedure and enter a confirmation in Caregiver UI 175. Rules Based Logic 135 will send relevant information with explanations to Patient UI 183 along with the next directive to Caregiver UI 175 at 4197, "Check estradiol and progesterone levels one week later." The provider will instruct the patient as to this directive, order the blood tests, enter the results, and input a confirmation in Caregiver UI 175. Rules-Based Logic 135 will send the next diagnostic step to Caregiver UI 175 at

4198, "is progesterone >15 ng/mL?" The provider inputs the answer into Caregiver UI 175 which sends the information to Storage 155. Rules-Based Logic 135 then sends the next directive or diagnostic step to Caregiver UI 175 depending on the previous answer.

If the answer at 4223 is no, then the information will be sent to and recorded in Storage 155 and Rules-Based Logic 135 will send relevant information with explanations to Patient UI 183 along with the next diagnostic step to Caregiver UI 175 at 4227, "Has the patient already taken letrozole?" The provider inputs the answer into Caregiver UI 175 which sends the information to Storage 155. Rules-Based Logic 135 then sends the next directive or diagnostic step to Caregiver UI 175 depending on the previous answer.

If the answer at 4227 is yes, then the information will be sent to and recorded in Storage 155 and Rules-Based Logic 135 will send relevant information with explanations to Patient UI 183 along with the next diagnostic step to Caregiver UI 175 at 4229, "Was the last dosing of letrozole 2.5 mg TID×5 days?" The provider inputs the answer into Caregiver UI 175 which sends the information to Storage 155. Rules-Based Logic 135 then sends the next directive or diagnostic step to Caregiver UI 175 depending on the previous answer.

If the answer at 4227 is no, then the information will be sent to and recorded in Storage 155 and Rules-Based Logic 135 will send relevant information with explanations to Patient UI 183 along with the next directive to Caregiver UI 175 at 4228, "Await next cycle and prescribe letrozole 2.5 mg daily×5 days, starting Day 3 of cycle." The provider will instruct the patient as to this directive, order the medication and then enter a confirmation into Caregiver UI 175. Rules-Based Logic 135 will send the next directive to Caregiver UI 175 at 4234, "Ovulatory prediction kit for 12 days, beginning 3 days after last dose of letrozole." The provider will instruct the patient as to the directive and enter a confirmation in Caregiver UI 175. Rules Based Logic 135 will send relevant information with explanations to Patient UI 183 along with the diagnostic step to Caregiver UI 175 at 4194, "Was there a robust LH surge?" The provider inputs the answer into Caregiver UI 175 which sends the information to Storage 155. Rules-Based Logic 135 then sends the next directive or diagnostic step to Caregiver UI 175 depending on the previous answer.

If the answer at 4229 is yes, then the information will be sent to and recorded in Storage 155 and Rules-Based Logic 135 will send relevant information with explanations to Patient UI 183 along with the next diagnostic step to Caregiver UI 175 at 4230, "Has the patient had 3 cycles on letrozole 2.5 mg TID?" The provider inputs the answer into Caregiver UI 175 which sends the information to Storage 155. Rules-Based Logic 135 then sends the next directive or diagnostic step to Caregiver UI 175 depending on the previous answer.

If the answer at 4229 is no, then the information will be sent to and recorded in Storage 155 and Rules-Based Logic 135 will send relevant information with explanations to Patient UI 183 along with the next directive to Caregiver UI 175 at 4232, "Increase letrozole by 2.5 mg daily×5 days, starting Day 3 of cycle." The provider will instruct the patient as to this directive, order the medication and then enter a confirmation in Caregiver UI 175. Rules-Based Logic 135 will send the next directive to Caregiver UI 175 at 4234, "Ovulatory prediction kit for 12 days, beginning 3 days after last dose of letrozole." The provider will instruct the patient as to the directive and enter a confirmation in Caregiver UI 175. Rules Based Logic 135 will send relevant information with explanations to Patient UI 183 along with the diagnostic step to Caregiver UI 175 at 4194, "Was there a robust LH surge?" The provider inputs the answer into Caregiver UI 175 which sends the information to Storage 155. Rules-Based Logic 135 then sends the next directive or diagnostic step to Caregiver UI 175 depending on the previous answer.

If the answer at 4230 is yes, then the information will be sent to and recorded in Storage 155 and Rules-Based Logic 135 will send relevant information with explanations to Patient UI 183 along with the next directive to Caregiver UI 175 at 4231, "Refer to specialist for injectable consultation or IVF."

The provider will instruct the patient as to the directive, make a referral, and enter a confirmation in Caregiver UI 175. Rules-Based Logic 135 then meets a hard stop.

If the answer at 4230 is no, then the information will be sent to and recorded in Storage 155 and Rules-Based Logic 135 will send relevant information with explanations to Patient UI 183 along with the next diagnostic step to Caregiver UI 175 at 4233, "Should the couple be more aggressive?" The provider inputs the answer into Caregiver UI 175 which sends the information to Storage 155. Rules-Based Logic then sends the next directive to Caregiver UI 175 depending on the previous answer.

If the answer at 4233 is yes, then the information will be sent to and recorded in Storage 155 and Rules-Based Logic 135 will send relevant information with explanations to Patient UI 183 along with the next directive to Caregiver UI 175 at 4231, "Refer to specialist for injectable consultation or IVF." The provider will instruct the patient as to the directive, make a referral, and enter a confirmation in Caregiver UI 175. Rules-Based Logic 135 then meets a hard stop If the answer at 4233 is no, then the information will be sent to and recorded in Storage 155 and Rules-Based Logic 135 will send relevant information with explanations to Patient UI 183 along with the next directive to Caregiver UI 175 at 4235, "Prescribe letrozole 2.5 mg PO TID×5 days, starting Day 3 of cycle." The provider will instruct the patient as to this directive, order the medication and then enter confirmation into Caregiver UI 175. Rules-Based Logic 135 will send the next directive to Caregiver UI 175 at 4234, "Ovulatory prediction kit for 12 days, beginning 3 days after last dose of letrozole." The provider will instruct the patient as to the directive and enter confirmation into Caregiver UI 175. Rules Based Logic 135 will send relevant information with explanations to Patient UI 183 along with the diagnostic step to Caregiver UI 175 at 4194, "Was there a robust LH surge?" The provider inputs the answer into Caregiver UI 175 which sends the information to Storage 155. Rules-Based Logic 135 then sends the next directive or diagnostic step to Caregiver UI 175 depending on the previous answer.

If the answer at 4236 is yes, then the information will be sent to and recorded in Storage 155 and Rules-Based Logic 135 will send relevant information with explanations to Patient UI 183 along with the next directive to Caregiver UI 175 at 4237, "Increase caloric intake and decrease exercise regimen if excessive. Resume protocol once BMI 20." The provider will instruct the patient as to this directive and then inputs the confirmation into Caregiver UI 175. Rules-Based Logic 135 will encounter a hard stop until BMI is >17. Resumption of protocol will be at 4006.

If the answer at 4236 is no, then the information will be sent to and recorded in Storage 155 and Rules-Based Logic 135 will send relevant information with explanations to Patient UI 183 along with the next directive to Caregiver UI 175 at 4238, "Prescribe Provera 10 mg/day×12 days." The provider will instruct the patient as to this directive, prescribe the medication and then inputs the confirmation into Caregiver UI 175. Rules-Based Logic 135 will send the next diagnostic step to Caregiver UI 175 at 4239, "Withdrawal bleed within 3 days of stopping Provera?" The provider inputs the answer into Caregiver 175 which sends the information to Storage 155. Rules-Based Logic 135 then sends the next directive or diagnostic step to Caregiver UI 175 depending on the previous answer.

If the answer at 4239 is yes, then the information will be sent to and recorded in Storage 155 and Rules-Based Logic 135 will send relevant information with explanations to Patient UI 183 along with the next directive to Caregiver UI 175 at 4235, "Prescribe letrozole 2.5 mg PO TID×5 days, starting Day 3 of cycle" The provider will instruct the patient as to this directive, order the medication and then enter confirmation into Caregiver UI 175. Rules-Based Logic 135 will send the next directive to Caregiver UI 175 at 4234, "Ovulatory prediction kit for 12 days, beginning 3 days after last dose of letrozole." The provider will instruct the patient as to the directive and enter confirmation into Caregiver UI 175. Rules Based Logic 135 will send relevant information with explanations to Patient UI 183 along with the diagnostic step to Caregiver UI 175 at 4194, "Was there a robust LH surge?" The provider inputs the answer into Caregiver UI 175 which sends the information to Storage 155. Rules-Based Logic 135 then sends the next directive or diagnostic step to Caregiver UI 175 depending on the previous answer.

If the answer at 4239 is no, then the information will be sent to and recorded in Storage 155 and Rules-Based Logic 135 will send relevant information with explanations to Patient UI 183 along with the next directive to Caregiver UI 175 at 4028, "Order blood tests: estradiol, progesterone, and hCG (or uCG)" The provider will instruct the patient as to this directive, order the blood tests, enter the results, and register a confirmation in Caregiver UI 175. Rules-Based Logic 135 will send the next diagnostic step to Caregiver UI 175 at 4029, "is hCG≥5 mIU/mL or uCG positive?" The provider inputs the answer into Caregiver UI 175 which sends the information to Storage 155. Rules-Based Logic 135 then sends the next directive or diagnostic step to Caregiver UI 175 depending on the previous answer.

Several embodiments are specifically illustrated and/or described herein. However, it will be appreciated that modifications and variations are covered by the above teachings and within the scope of the appended claims without departing from the spirit and intended scope thereof. For example, the systems and methods discussed herein may be applied to other medical treatments and/or conditions.

The embodiments discussed herein are illustrative of the present invention. As these embodiments of the present invention are described with reference to illustrations, various modifications or adaptations of the methods and or specific structures described may become apparent to those skilled in the art. All such modifications, adaptations, or variations that rely upon the teachings of the present invention, and through which these teachings have advanced the art, are considered to be within the spirit and scope of the present invention. Hence, these descriptions and drawings should not be considered in a limiting sense, as it is understood that the present invention is in no way limited to only the embodiments illustrated.

Computing systems and/or logic referred to herein can comprise an integrated circuit, a microprocessor, a personal computer, a server, a distributed computing system, a communication device, a network device, or the like, and various combinations of the same. A computing system or logic may also comprise volatile and/or non-volatile memory such as random access memory (RAM), dynamic random access memory (DRAM), static random access memory (SRAM), magnetic media, optical media, nano-media, a hard drive, a compact disk, a digital versatile disc (DVD), optical circuits, and/or other devices configured for storing analog or digital information, such as in a database. A computer-readable medium, as used herein, expressly excludes paper. Computer-implemented steps of the methods noted herein can comprise a set of instructions stored on a computer-readable medium that when executed cause the computing system to perform the steps. A computing system programmed to perform particular functions pursuant to instructions from program software is a special purpose computing system for performing those particular functions. Data that is manipulated by a special purpose computing system while performing those particular functions is at least electronically saved in buffers of the computing system, physically changing the special purpose computing system from one state to the next with each change to the stored data.

The "logic" discussed herein is explicitly defined to include hardware, firmware or software stored on a non-transient computer readable medium, or any combinations thereof. This logic may be implemented in an electronic and/or digital device (e.g., a circuit) to produce a special purpose computing system. Any of the systems discussed herein optionally include a microprocessor, including electronic and/or optical circuits, configured to execute any combination of the logic discussed herein. The methods discussed herein optionally include execution of the logic by said microprocessor.

The invention claimed is:

1. A communication system for the treatment of infertility, the communication system comprising:

an expert system embodied in one or more computing devices, wherein the expert system includes:

a rule-based logic database storing selections for infertility treatments, the rule-based logic database including a plurality of rules stored in association with clinical data and the infertility treatments, wherein the rule-based logic database is configured to apply the plurality of rules to provide selections of one or more infertility treatments from among the one or more of the alternative treatments, a reinforcement logic database storing quality scores in association with respective rules of the plurality of rules, the scores being based on at least clinical success of the selections, a knowledge graph storing a patient's accrued data in association with a plurality of nodes, wherein each node is associated with one or more of the selections, a library database storing information regarding the infertility treatments and the clinical data regarding the first patient, a content distribution logic configured to automatically provide content from the library of information to the first patient, a microprocessor operatively coupled to the rule-based logic database, the reinforcement logic database and the knowledge graph, wherein the microprocessor is configured to execute the plurality of rules stored in the rule-based logic database and the content distribution logic, wherein members of the plurality of rules are associated with an initial score, the initial score being based on a perceived quality of data on which the respective rule is based, and the scores are based on both the initial score associated with a particular member and the clinical success of the selections and wherein a machine learning system is configured to supplement the selections provided by the rule-based logic database, wherein the machine learning system is trained based on clinical success of the selections from among the infertility treatments to thereby provide a preference among the selections provided by the rule-based logic database and wherein the training logic is configured to train the machine learning system based on clinical success provided by the caregiver and the clinical data;

a caregiver application embodied in a caregiver computing device, wherein the caregiver application includes:

a clinical input element configured to receive the clinical data, a caregiver user interface elements configured for a caregiver to receive the selections from among the infertility treatments, and status logic configured to track treatment status of the patient, the treatment including the selections of the infertility treatments; and one or more patient applications, each embodied in a patient computing device, wherein the patient applications include:

a patient user interface element configured to display the content from the library to the first patient.

2. The system of claim 1, further comprising a couple logic configured to treat a pair of patients as a reproductive unit and to coordinate the selections provided to both members of the reproductive unit.

3. The system of claim 1, further comprising the clinical input configured to receive the clinical data, the clinical input being included on the caregiver computing device or the patient computing device.

4. The system of claim 1, further comprising a sensor connected to the patient computing device, the sensor being configured to collect at least part of the clinical data.

5. The system of claim 1, wherein the clinical data includes at least one of:

patient age, patient race, patient weight, patient H1c, patient birth history.

6. The system of claim 1, wherein the library of information includes content selected to answer patient questions, and wherein the content distribution logic is optimized to minimize a number of questions asked a caregiver.

7. The system of claim 1, wherein the caregiver user interface is configured for a caregiver to approve the selections, to forward the selections to the patient, to approve the content from the library of information, to forward the content from the library of information to the patient, to answer questions received from the patient, to require that the caregiver provide the clinical data, and/or to enter the clinical data.

8. The system of claim 1, wherein the patient user interface is further configured for the patient to enter the clinical data, to send questions to the caregiver, to require that the patient provide clinical data, and/or to display data generated by the sensor.

9. The system of claim 1, wherein the machine learning system is further configured to provide a preference among the selections provided by the rule-based logic database.

10. The system of claim 2, wherein the reproductive unit includes a male patient and a female patient, and the selections are based on clinical data regarding both the male patient and the female patient.

11. The system of claim 3, wherein the clinical input is configured to receive the clinical data from a medical records system or a sensor.

12. The system of claim 3, wherein the sensor is configured to be worn by the first patient.

13. The system of claim 3, wherein the sensor is a temperature sensor, a sleep sensor, a blood glucose sensor, a motion sensor, or a hormone sensor.

14. A method for the treatment of infertility, the method comprising:

storing, in a rule-based logic database, selections for infertility treatments, the rule-based logic database including a plurality of rules stored in association with clinical data and the infertility treatments, wherein the rule-based logic database is configured to apply the plurality of rules to provide selections of one or more infertility treatments from among the one or more of the alternative treatments wherein members of the plurality of rules are associated with an initial score, the initial score being based on a perceived quality of data on which the respective rule is based, and the scores are based on both the initial score associated with a particular member and the clinical success of the selections;

storing, in a reinforcement logic database, quality scores in association with respective rules of the plurality of rules, the scores being based on at least clinical success of the selections;

storing, in a knowledge graph, a patient's accrued data in association with a plurality of nodes, wherein each node is associated with one or more of the selections, a library database storing information regarding the infertility treatments and the clinical data regarding the first patient, automatically providing content, based on a content distribution logic, from the library of information to the first patient; and supplementing the selections provided by the rule-based logic database with a machine learning system, wherein the machine learning system is trained based on clinical success of the selections from among the infertility treatments to thereby provide a preference among the selections provided by the rule-based logic database and wherein the training logic is configured to train the machine learning system based on clinical success provided by the caregiver and clinical data.

15. The method of claim 14, further comprising treating a pair of patients as a reproductive unit and to coordinate the selections provided to both members of the reproductive unit.

16. The method of claim 14 further comprising collecting at least a part of the clinical data with a sensor connected to a patient computing device.

17. The method of claim 14, wherein the clinical data includes at least one of: patient age, patient race, patient weight, patient H1c, patient birth history.

18. The method of claim 14, wherein the library of information includes content selected to answer patient questions, and wherein the content distribution logic is optimized to minimize a number of questions asked a caregiver.

19. The method of claim 14, wherein a caregiver user interface is configured for a caregiver to approve the selections, to forward the selections to the patient, to approve the content from the library of information, to forward the content from the library of information to the patient, to answer questions received from the patient, to require that the caregiver provide the clinical data, and/or to enter the clinical data.

20. The method of claim 14, wherein a patient user interface is further configured for the patient to enter the clinical data, to send questions to the caregiver, to require that the patient provide clinical data, and/or to display data generated by the sensor.

21. The system of claim 14, wherein the machine learning system is further configured to provide a preference among selections provided by the rule-based logic database.

22. The method of claim 15, wherein the reproductive unit includes a male patient and a female patient, and the selections are based on clinical data regarding both the male patient and the female patient.

23. The method of claim 16, wherein the clinical input is configured to receive the clinical data from a medical records system or a sensor.

24. The method of claim 16, wherein the sensor is configured to be worn by the first patient.

25. The method of claim 16, wherein the sensor is a temperature sensor, a sleep sensor, a blood glucose sensor, a motion sensor, or a hormone sensor.

\*    \*    \*    \*    \*